US012799213B2

(12) United States Patent
Daly et al.

(10) Patent No.: US 12,799,213 B2
(45) Date of Patent: Nov. 17, 2026

(54) HUMAN ANTIBODIES THAT BIND RET AND METHODS OF USE THEREOF

(71) Applicant: Regeneron Pharmaceuticals, Inc., Tarrytown, NY (US)

(72) Inventors: Christopher Daly, New York, NY (US); Gavin Thurston, Briacliff Manor, NY (US); Nicholas Papadopoulos, Woodlands, TX (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1441 days.

(21) Appl. No.: 17/602,562

(22) PCT Filed: Apr. 9, 2020

(86) PCT No.: PCT/US2020/027554

§ 371 (c)(1),
(2) Date: Oct. 8, 2021

(87) PCT Pub. No.: WO2020/210551

PCT Pub. Date: Oct. 15, 2020

(65) Prior Publication Data

US 2022/0185900 A1 Jun. 16, 2022

Related U.S. Application Data

(60) Provisional application No. 62/832,218, filed on Apr. 10, 2019.

(51) Int. Cl.

| | |
|---|---|
| ***C07K 16/28*** | (2006.01) |
| ***A61K 39/00*** | (2006.01) |
| ***A61K 39/395*** | (2006.01) |
| ***A61K 45/06*** | (2006.01) |
| ***A61P 25/00*** | (2006.01) |
| ***A61P 25/04*** | (2006.01) |
| ***A61P 29/00*** | (2006.01) |
| ***A61P 35/00*** | (2006.01) |
| ***A61P 35/02*** | (2006.01) |

(52) U.S. Cl.

CPC ...... *C07K 16/2863* (2013.01); *A61K 39/3955* (2013.01); *A61K 45/06* (2013.01); *A61P 25/00* (2018.01); *A61P 25/04* (2018.01); *A61P 29/00* (2018.01); *A61P 35/00* (2018.01); *A61P 35/02* (2018.01); *A61K 2039/505* (2013.01); *C07K 2317/21* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/74* (2013.01); *C07K 2317/76* (2013.01); *C07K 2317/92* (2013.01)

(58) Field of Classification Search

CPC ............ C07K 16/2863; C07K 2317/21; C07K 2317/565; C07K 2317/74; C07K 2317/76; C07K 2317/92; C07K 2317/24; C07K 2317/51; C07K 2317/515; C07K 2317/56; A61K 39/3955; A61K 45/06; A61K 2039/505; A61P 35/00; A61P 25/04; A61P 25/00; A61P 29/00; A61P 35/02

See application file for complete search history.

(56) References Cited

U.S. PATENT DOCUMENTS

| | | | |
|---|---|---|---|
| 6,596,541 | B2 | 7/2003 | Murphy et al. |
| 6,861,509 | B1 | 3/2005 | Sanicola-Nadel et al. |
| 2004/0101920 | A1 | 5/2004 | Radziejewski et al. |
| 2007/0280945 | A1 | 12/2007 | Stevens et al. |
| 2009/0136502 | A1 | 5/2009 | Arai et al. |
| 2010/0331527 | A1 | 12/2010 | Davis et al. |
| 2011/0195454 | A1 | 8/2011 | McWhirter et al. |

(Continued)

FOREIGN PATENT DOCUMENTS

| | | | |
|---|---|---|---|
| EP | 1941909 | A1 | 7/2008 |
| WO | WO 2005/103081 | | 11/2005 |

(Continued)

OTHER PUBLICATIONS

Jiang et al. "A Novel Peptide Isolated from a Phage Display Peptide Library with Trastuzumab Can Mimic Antigen Epitope of HER-2". J. Biol. Chem. Feb. 11, 2005; 280 (6): 4656-4662 (Year: 2005).*

Riemer et al. "Matching of trastuzumab (Herceptin®) epitope mimics onto the surface of Her-2/neu—a new method of epitope definition". Mol. Immunol. 2005; 42: 1121-1124); see entire document, particularly col. 1 of p. 1123. (Year: 2005).*

Al-Lazikani, et al. (1997) "Standard Conformations for the Canonical Structures of Immunoglobulins", J. Mol. Biol., 273:927-948.

Allen (1999) "The Art, Science and Technology of Pharmaceutical Compounding" Fifth Edition, American Pharmacists Association, Washington, D.C.

Altschul, et al. (1997) "Gapped BLAST and PSI-BLAST: A New Generation of Protein Database Search Programs", Nucleic Acids Res., 25:3389-3402.

(Continued)

*Primary Examiner* — Mark Halvorson
*Assistant Examiner* — Lea S O'Brien
(74) *Attorney, Agent, or Firm* — Schwabe, Williamson & Wyatt, PC; Kajal Chowdhury

(57) ABSTRACT

The present invention provides fully human antibodies that bind to the RET receptor tyrosine kinase, compositions comprising the antibodies and methods of use. The antibodies of the invention are useful for treating diseases, disorders, or conditions associated with expression, activation, or signaling of the RET receptor tyrosine kinase gene, or a rearranged form thereof, including cancerous conditions and the pain associated with the cancer, or for alleviating the pain associated with other conditions attributed to, at least in part, by expression, activation or signaling of RET. The antibodies specific for RET may be useful for slowing tumor cell growth or tumor cell proliferation and also for alleviating the pain associated with the cancer and other conditions. The antibodies may also be useful for diagnosis of a disease, disorder or condition associated with RET activation or signaling.

28 Claims, 1 Drawing Sheet

Specification includes a Sequence Listing.

(56) References Cited

U.S. PATENT DOCUMENTS

| | | | |
|---|---|---|---|
| 2011/0311515 | A1 | 12/2011 | Bouche et al. |
| 2012/0128669 | A1 | 5/2012 | Depla et al. |

FOREIGN PATENT DOCUMENTS

| | | | |
|---|---|---|---|
| WO | 2007/049624 | A1 | 5/2007 |
| WO | WO 2014/031712 | A1 | 2/2014 |

OTHER PUBLICATIONS

Altschul, et al. (1990) "Basic Local Alignment Search Tool", J. Mol. Biol., 215: 403-410.

Arighi, et al. (2005) "RET Tyrosine Kinase Signaling in Development and Cancer", Cytokine Growth Factor Rev, 16:441-467.

Ballerini, et al, (2012) "RET Fusion Genes are Associated with Chronic Myelomonocytic Leukemia and Enhance Monocytic Differentiation", Leukemia, 26:2384-2389.

Baloh, et al. (2000) "The GDNF Family Ligands and Receptors-Implications for Neural Development", Curr Opin Neurobiol, 10:103-110.

Bitonti and Dumont (2006) "Pulmonary Administration of Therapeutic Proteins Using an Immunoglobulin Transport Pathway", Adv. Drug Deliv. Rev, 58:1106-1118.

Borrello, et al (2013) "RET Inhibition: Implications in Cancer Therapy", Expert Opin. Ther. Targets, 17(4):403-419.

Carter, et al. (2001), "Conversation of RET Proto-Oncogen Splicing Variants and Implications for RET Isoform Function", Cytogenet Cell Genet, 95:169-176.

Chow, et al., (2007) "Sunitinib: From Rational Design to Clinical Efficacy", J. Clin. Oncol., 25:884-896.

Coulpier, et al (2002) "Coordinated Activation of Autophosphorylation Sites in the RET Receptor Tyrosine Kinase", J Biol Chem, 277:1991-1999.

Cuccuru, et al. (2004) "Cellular Effects and Antitumor Activity of RET Inhibitor RPI-1 on MEN2A-Associated Medullary Thyroid Carcinoma", J Natl Cancer Inst, 96(13):1006-1014.

De Groot et al. (2006) "RET as a Diagnostic and Therapeutic Target in Sporadic and Hereditary Endocrine Tumors", Endocrine Reviews, 27(5):535-560.

Drillon et al. (2017) "Targeting RET-driven Cancers: Lessons from Evolving Preclinical and Clinical Landscapes", Nature Reviews Clinical Oncology, 15(3):151-167.

Ehring (1999) "Hydrogen Exchange/Electrospray Ionization Mass Spectrometry Studies of Structural Features of Proteins and Protein/Protein Interactions", Analytical Biochemistry, 267(2):252-259.

Engen and Smith (2001) "The Basic of Ion Chromatography", Anal. Chem., 73:256A-265A.

Fischer, et al. (1998) "Papillary Thyroid Carcinoma Oncogene (RET/PTC) Alters the Nuclear Envelope and Chromatin Structure", Am J Pathol., 153:1443-1450.

Fusco, et al. (1987) "A New Oncogene in Human Thyroid Papillary Carcinomas and their Lymph-nodal Metastases", Nature, 328:170-172.

GenBank accession No. AF040962 Nucleotide [Internet]. Bethesda (MD): National Library of Medicine (US), National Center for Biotechnology Information; [1998]—Accession No. AF040962, "*Homo sapiens* Persephin mRNA, Complete CDS", cited on Mar. 6, 1998, [online], [retrieved on Dec. 27, 2021]. Retrieved from: https://www.ncbi.nlm.nihm.gov/nuccore/AF040962, 1 page.

GenBank accession No. NM_001495.4 Nucleotide [Internet]. Bethesda (MD): National Library of Medicine (US), National Center for Biotechnology Information; [2018]—Accession No. NM_001495.4, "*Homo sapiens* GDNF Family Receptor Alpha 2 (GFRA2), Transcript Variant 1, mRNA", cited on Jun. 23, 2018, [online], [retrieved on Dec. 27, 2021]. Retrieved from: https://www.ncbi.nlm.nihm.gov/nuccore/NM_001495.4, 5 pages.

GenBank accession No. NM_004558 Nucleotide [Internet]. Bethesda (MD): National Library of Medicine (US), National Center for Biotechnology Information; [2021]—Accession No. NM_004558, "*Homo sapiens* Neurturin (NRTN), mRNA", cited on Jun. 30, 2021, [online], [retrieved on Dec. 27, 2021]. Retrieved from: https://www.ncbi.nlm.nihm.gov/nuccore/NM_004558, 4 pages.

GenBank accession No. NM_022139 Nucleotide [Internet]. Bethesda (MD): National Library of Medicine (US), National Center for Biotechnology Information; [2021]—Accession No. NM_022139, "*Homo sapiens* GDNF Family Receptor Alpha 4 (GFRA4), Transcript Variant 1, mRNA", cited on Aug. 2, 2021, [online], [retrieved on Dec. 27, 2021]. Retrieved from: https://www.ncbi.nlm.nihm.gov/nuccore/NM_022139, 4 pages.

GenBank accession No. NM_145762.2 Nucleotide [Internet]. Bethesda (MD): National Library of Medicine (US), National Center for Biotechnology Information; [2019]—Accession No. NM_145762.2, "*Homo sapiens* GDNF Family Receptor Alpha 4 (GFRA4), Transcript Variant 2, mRNA", cited on Dec. 26, 2019, [online], [retrieved on Dec. 27, 2021]. Retrieved from: https://www.ncbi.nlm.nihm.gov/nuccore/NM_145762.2, 4 pages.

GenBank accession No. NP_000505.1 Protein [Internet]. Bethesda (MD): National Library of Medicine (US), National Center for Biotechnology Information; [2021]—Accession No. NP_000505.1 "Glial Cell Line-Derived Neurotrophic Factor Isoform 1 Preproprotein [*Homo sapiens*]", cited on Dec. 20, 2021, [online], [retrieved on Dec. 27, 2021]. Retrieved from: https://www.ncbi.nlm.nihm.gov/protein/NP_000505.1, 4 pages.

GenBank accession No. NP_001487.2 Protein [Internet]. Bethesda (MD): National Library of Medicine (US), National Center for Biotechnology Information; [2021]—Accession No. NP_001487.2, "GDNF Family Receptor Alpha-3 Preproprotein [*Homo sapiens*]", cited on Feb. 16, 2021, [online], [retrieved on Dec. 27, 2021]. Retrieved from: https://www.ncbi.nlm.nihm.gov/protein/NP_001487.2, 4 pages.

GenBank accession No. NP_005255.1 Protein [Internet]. Bethesda (MD): National Library of Medicine (US), National Center for Biotechnology Information; [2021]—Accession No. NP_005255.1, "GDNF Family Receptor Alpha-1 Isoform a Preproprotein [*Homo sapiens*]", cited on Oct. 31, 2021, [online], [retrieved on Dec. 27, 2021]. Retrieved from: https://www.ncbi.nlm.nihm.gov/protein/NP_005255.1, 4 pages.

GenBank as accession No. NM_020630.4 Nucleotide [Internet]. Bethesda (MD): National Library of Medicine (US), National Center for Biotechnology Information; [2017]—Accession No. NM_020630.4, "*Homo sapiens* RET Proto-Oncogene (RET), Transcript Variant 4, mRNA", cited on Sep. 11, 2017, [online], [retrieved on Dec. 27, 2021]. Retrieved from: https://www.ncbi.nlm.nihm.gov/nuccore/NM_020630.4, 6 pages.

GenBank as accession number NM_020975.4 Nucleotide [Internet]. Bethesda (MD): National Library of Medicine (US), National Center for Biotechnology Information; [2017]—Accession No. NM_020975.4, "*Homo sapiens* RET Proto-Oncogene (RET), Transcript Variant 2, mRNA", cited on Sep. 11, 2017, [online], [retrieved on Dec. 27, 2021]. Retrieved from: https://www.ncbi.nlm.nihm.gov/nuccore/NM_020975.4, 7 pages.

GenBank as accession number NP_065681.1 Protein [Internet]. Bethesda (MD): National Library of Medicine (US), National Center for Biotechnology Information; [2021]—Accession No. NP_065681.1, "Proto-Oncogene Tyrosine-Protein Kinase Receptor RET Isoform C Precursor [*Homo sapiens*]", cited on Dec. 20, 2021, [online], [retrieved on Dec. 27, 2021]. Retrieved from: https://www.ncbi.nlm.nihm.gov/protein/NP_065681.1, 5 pages.

GenBank as accession number NP_066124.1 Protein [Internet]. Bethesda (MD): National Library of Medicine (US), National Center for Biotechnology Information; [2021]—Accession No. NP_006124.1, "Proto-Oncogene Tyrosine-Protein Kinase Receptor RET Isoform a Precursor [*Homo sapiens*]", cited on Dec. 20, 2021, [online], [retrieved on Dec. 27, 2021]. Retrieved from: https://www.ncbi.nlm.nihm.gov/protein/NP_066124.1, 6 pages.

Golden, et al. (1998) "Expression of Neurturin, GDNF, and their Receptors in the Adult Mouse CNS", J. Comp. Neurol., 398:139-150.

Golden, et al. (1999) "Expression of Neurturin, GDNF, and GDNF Family-Receptor mRNA in the Developing and Mature Mouse", Exp. Neurol., 158:504-528.

(56) References Cited

OTHER PUBLICATIONS

Gonnet, et al. (1992) "Exhaustive Matching of the Entire Protein Sequence Database", Science, 256: 1443-1445.
Grieco, et al. (1990) "PTC is a Novel Rearranged Form of the RET Proto-Oncogene and is Frequently Detected in Vivo in Human Thyroid Papillary Carcinomas", Cell, 60:557-563.
Harlow and Lane (2014) "Antibodies: A Laboratory Manual" Second Edition, Cold Spring Harbor Press, Cold Spring Harb., NY.
International Search Report and Written Opinion for PCT/US2020/027554, mailed Oct. 6, 2020, 17 pages.
Junghans, et al. (1990) "Anti-Tac-H, a Humanized Antibody to the Interleukin 2 Receptor with New Features for Immunotherapy in Malignant and Immune Disorders", Cancer Res., 50:1495-1502.
Kabat, et al. (1991) "Sequences of Proteins of Immunological Interest," National Institutes of Health, Bethesda, Md.
Kufer, et al. (2004) "A Revival of Bispecific Antibodies", Trends Biotechnol., 22:238-244.
Langer (1990) "New Methods of Drug Delivery", Science, 249:1527-1533.
Leboulleux, et al. (2012) "Vandetanib in Locally Advanced or Metastatic Differentiated Thyroid Cancer: A Randomised, Double-Blind, Phase 2 Trial", Lancet Oncol, 13:897-905.
Maeda, et al. (2004) "Biochemical and Biological Responses Induced by Coupling of Gab1 to Phosphatidylinositol 3-Kinase in RET-Expressing Cells", Biochem Biophys Res Communi., 323(1): 345-354.
Maillet, et al. (2008) "Aerodynamical, Immunological and Pharmacological Properties of the Anticancer Antibody Cetuximab Following Nebulization", Pharmaceutical Research, 25(6):1318-1326.
Martin, et al. (1989) "Modeling Antibody Hypervariable Loops: A Combined Algorithm", Proc. Natl. Acad. Sci. USA, 86:9268-9272.
Mulligan, et al., (1994) "Specific Mutations of the RET Proto-Oncogene are Related to Disease Phenotype in MEN2A and FMTC", Nat. Genet., 6:70-74.
Narita, et al., (2009) "Functional RET G691S Polymorphism in Cutaneous Malignant Melanoma", Oncogene, 28:3058-3068.
Nguyen et al. (2015) "Preclinical Efficacy and Safety Assessment of an Antibody-Drug Conjugate Targeting the c-RET Proto-Oncogene for Breast Carcinoma", Clinical Cancer Research, 21(24):5552-5562.
Padlan, et al. (1995) "Identification of Specificity-Determining Residues in Antibodies", FASEB J., 9:133-139.
Pearson (1994) "Using the FASTA Program to Search Protein and DNA Sequence Databases", Methods Mol. Biol., 24: 307-331.
Pearson (2000) "Flexible Sequence Similarity Searching with the FASTA3 Program Package", Methods in Molecular Biology, 132:185-219.
Powell, et al. (1998) "Compendium of Excipients for Parenteral Formulations", PDA J Pharm Sci Technol, 52:238-311.
Reddy, et al. (2000) "Elimination of Fc Receptor-Dependent Effector Functions of a Modified IgG4 Monoclonal Antibody to Human CD4", J. Immunol., 164:1925-1933.
Reineke (2004) "Antibody Epitope Mapping Using Arrays of Synthetic Peptides", Methods Mol Biol, 248:443-463.
Rossel, et al. (1997) "Distinct Biological Properties of Two RET Isoforms Activated by MEN 2A and MEN 2B Mutations", Oncogene, 14:265-275.
Salvatore et al. (2002) "Generation and Characterization of Novel Monoclonal Antibodies to the Ret Receptor Tyrosine Kinase", Biochemical and Biophysical Research Communications, Elsevier, 294(4):813-817.
Santoro, et al., (1994) "An Epidermal Growth Factor Receptor/RET Chimera Generates Mitogenic and Transforming Signals: Evidence for a RET-Specific Signaling Pathway", Mol. Cell Biol., 14(1):663-675.
Sawai, et al. (2005) "The G691S Ret Polymorphism Increases Glial Cell Line-Derived Neurotrophic Factor-Induced Pancreatic Cancer Cell Invasion by Amplifying Mitogen-Activated Protein Kinase Signaling", Cancer Res., 65(24):11536-11544.
Segouffin-Cariou, et al. (2000) "Transforming Ability of MEN2A-RET Requires Activation of the Phosphatidylinositol 3-Kinase/AKT Signaling Pathway", 275(5):3568-3576.
Serra et al. (2005) "Ret, GFRalpha-1, GFRalpha-2 and GFRalpha-3 Receptors in the Human Hippocampus and Fascia Dentata", International Journal of Developmental Neuroscience, 23:425-438.
Shield, et al. (2002) "Lack of Fucose on Human IgG1 N-Linked Oligosaccharide Improves Binding to Human FcyRIII and Antibody-Dependent Cellular Toxicity", JBC, 277:26733-26740.
Stine, et al. (2011) "Steroid Hormone Modulations of RET Through Two Estrogen Responsive Enhancers in Breast Cancer", Human Molecular Genetics, 20(19):3746-3756.
Takahashi, et al. (1985) "Activation of a Novel Human Transforming Gene, RET, by DNA Rearrangement", Cell, 42(2):581-588.
Tomer (2000) "Characterization of a Discontinuous Epitope of the Human Immunodeficiency Virus (HIV) Core Protein P24 by Epitope Excision and Differential Chemical Modification Followed by Mass Spectrometric Peptide Mapping Analysis", Protein Science 9: 487-496.
Trupp, et al., (1999) "RET-Dependent and -Independent Mechanisms of Glial Cell Line-Derived Neurotrophic Factor Signaling in Neuronal Cells", J Biol. Chem., 274:20885-20894.
Tutt et al. (1991) "Trispecific F(ab')3 Derivatives that Use Cooperative Signaling Via the TCR/CD3 Complex and CD2 to Activate and Redirect Resting Cytotoxic T Cells", J. Immunol., 147:60-69.
Vajdos, et al. (2002) "Comprehensive Functional Maps of the Antigen-binding Site of an Anti-ErbB2 Antibody Obtained with Shotgun Scanning Mutagenesis", J Mol Biol, 320:415-428.
Van Weering, (1997) "Glial Cell Line-Derived Neurotrophic Factor Induces RET-Mediated Lamellipodia Formation", J Biol Chem, 272(1):249-254.
Wang, et al. (2012) "The Rearranged During Transfection/Papillary Thyroid Carcinoma Tyrosine Kinase is an Estrogen-Dependent Gene Required for the Growth of Estrogen Receptor Positive Breast Cancer Cells", Breast Cancer Res Treat, 133(2):487-500.
Wells, et al. (2012) Vandetanib in Patients with Locally Advanced or Metastatic Medullary Thyroid Cancer: A Randomized, Double-Blind Phase III Trial, J Clin Oncol, 30:134-141.
Wilhelm, et al. (2006) "Discovery and Development of Sorafenib: A Multikinase Inhibitor for Treating Cancer", Nat Rev Drug Discov, 5:835-844.
Worby, et al. (1996) "Glial Cell Line-Derived Neurotrophic Factor Signals Through the RET Receptor and Activates Mitogen-Activated Protein Kinase", J Biol Chem, 271:23619-23622.
Wu, et al. (1987) "Receptor-Mediated in Vitro Gene Transformation by a Soluble DNA Carrier System", J. Biol. Chem., 262:4429-4432.
Zhang, et al., (2010) "XL-184, a MET, VEGFR-2 and RET Kinase Inhibitor for the Treatment of Thyroid Cancer, Glioblastoma Mulitforme and NSCLC", IDrugs, 13:112-121.
Van Weering, et al. (1995) "RET Receptor Tyrosine Kinase Activates Extracellular Signal-Regulated Kinase 2 in SK-N-MC Cells", Oncogene, 11(11):2207-2214.
Viglietto, et al. (1995) "RET/PTC Oncogene Activation is an Early Event in Thyroid Carcinogenesis", Oncogene, 11:1207-1210.

* cited by examiner

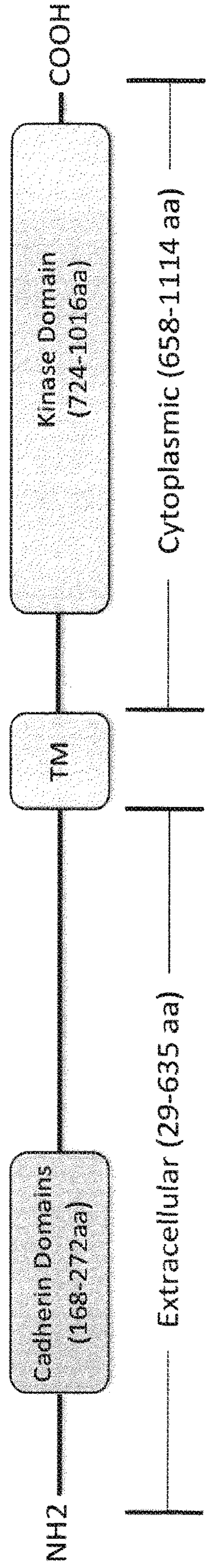
Schematic representation of the Human Ret receptor, annotated according to UniProt entry P07949.

SEQUENCE LISTING

```
<160> NUMBER OF SEQ ID NOS: 313

<210> SEQ ID NO 1
<211> LENGTH: 345
<212> TYPE: DNA
<213> ORGANISM: Artificial Sequence
<220> FEATURE:
<223> OTHER INFORMATION: Synthetic

<400> SEQUENCE: 1

caggtgcagc tggtggagtc tgggggaggc gtggtccagc ctgggaggtc cctgagactc     60

tcctgtgtag tgtctggatt caccttcagt aactatggca tgcactgggt ccgccagggt    120

ccaggcaggg gcctggagtg gttggcactt atatggtatg atggaagtga taaatactat    180

gcagagtccg tgaggggccg attcaccatc tccagagaca attccaagaa cacggtgtat    240

ctgcaaatga acagcctgag agccgaggac acggctatgt attactgtac gagagatcgg    300

atttttgact actggggcca gggaaccctg gtcaccgtct cctca                    345


<210> SEQ ID NO 2
<211> LENGTH: 115
<212> TYPE: PRT
<213> ORGANISM: Artificial Sequence
<220> FEATURE:
<223> OTHER INFORMATION: Synthetic
```

<400> SEQUENCE: 2

Gln Val Gln Leu Val Glu Ser Gly Gly Gly Val Val Gln Pro Gly Arg
1 5 10 15

Ser Leu Arg Leu Ser Cys Val Val Ser Gly Phe Thr Phe Ser Asn Tyr
20 25 30

Gly Met His Trp Val Arg Gln Gly Pro Gly Arg Gly Leu Glu Trp Leu
35 40 45

Ala Leu Ile Trp Tyr Asp Gly Ser Asp Lys Tyr Tyr Ala Glu Ser Val
50 55 60

Arg Gly Arg Phe Thr Ile Ser Arg Asp Asn Ser Lys Asn Thr Val Tyr
65 70 75 80

Leu Gln Met Asn Ser Leu Arg Ala Glu Asp Thr Ala Met Tyr Tyr Cys
85 90 95

Thr Arg Asp Arg Ile Phe Asp Tyr Trp Gly Gln Gly Thr Leu Val Thr
100 105 110

Val Ser Ser
115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagtaacta tggc 24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Asn Tyr Gly
1 5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatggtatg atggaagtga taaa 24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Trp Tyr Asp Gly Ser Asp Lys
1 5

<210> SEQ ID NO 7

<211> LENGTH: 24
<212> TYPE: DNA
<213> ORGANISM: Artificial Sequence
<220> FEATURE:
<223> OTHER INFORMATION: Synthetic

<400> SEQUENCE: 7
acgagagatc ggatttttga ctac 24

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Thr Arg Asp Arg Ile Phe Asp Tyr
1 5

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9
gccatccaga tgacccagtc tccatcctcc ctgtctgcat ctgtcggaga cagagtcacc 60
atcacttgcc gggcaagtca ggacattaga aatgatttag gctggtatca gcataatcca 120
gggaaagccc ctaacctcct aatctatgct gcgtccactt tacaaattgg ggtcccatca 180
aggttccgcg gcagtggatc tggcacagat ttcactctca ccatcagcag cctgcagcct 240
gaagattttg caacttatta ctgtctacaa gattttgatt acccgctctc tttcggcgga 300
gggaccaagg tggagatcag a 321

<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Ala Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Arg Asn Asp
20 25 30

Leu Gly Trp Tyr Gln His Asn Pro Gly Lys Ala Pro Asn Leu Leu Ile
35 40 45

Tyr Ala Ala Ser Thr Leu Gln Ile Gly Val Pro Ser Arg Phe Arg Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Phe Asp Tyr Pro Leu
85 90 95

Ser Phe Gly Gly Gly Thr Lys Val Glu Ile Arg
100 105

<210> SEQ ID NO 11
<211> LENGTH: 18

<212> TYPE: DNA
<213> ORGANISM: Artificial Sequence
<220> FEATURE:
<223> OTHER INFORMATION: Synthetic

<400> SEQUENCE: 11
caggacatta gaaatgat 18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Asp Ile Arg Asn Asp
1 5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcgtcc 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
ctacaagatt ttgattaccc gctctct 27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Leu Gln Asp Phe Asp Tyr Pro Leu Ser
1 5

<210> SEQ ID NO 17
<211> LENGTH: 384
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tgggggaggc gtggtccagc ctgggaggtc cctgagactc 60
tcctgtgcag cgtctggatt caccttcagt ggctctggca tgcactgggt ccgccaggct 120
ccaggcaagg ggctggagtg ggtggcagtt atatgggaag atggaagtaa taaatactac 180
gcagactccg tgaggggccg attcaccatc tccagagaca atttcaagaa cacgctgtat 240
ctgcaaatga acagcctgag agccgaggac acggctgtgt attactgtgc gagacagact 300
atggttcggg gagttatccg cttttactac tactactacg gtatggacgt ctggggccaa 360
gggaccacgg tcaccgtctc ctca 384

<210> SEQ ID NO 18
<211> LENGTH: 128
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Gly Ser
20 25 30

Gly Met His Trp Val Arg Gln Ala Pro Gly Lys Gly Leu Glu Trp Val
35 40 45

Ala Val Ile Trp Glu Asp Gly Ser Asn Lys Tyr Tyr Ala Asp Ser Val
50 55 60

Arg Gly Arg Phe Thr Ile Ser Arg Asp Asn Phe Lys Asn Thr Leu Tyr
65 70 75 80

Leu Gln Met Asn Ser Leu Arg Ala Glu Asp Thr Ala Val Tyr Tyr Cys
85 90 95

Ala Arg Gln Thr Met Val Arg Gly Val Ile Arg Phe Tyr Tyr Tyr Tyr
100 105 110

Tyr Gly Met Asp Val Trp Gly Gln Gly Thr Thr Val Thr Val Ser Ser
115 120 125

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagtggctc tggc 24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Gly Ser Gly
1 5

<210> SEQ ID NO 21
<211> LENGTH: 24

<212> TYPE: DNA
<213> ORGANISM: Artificial Sequence
<220> FEATURE:
<223> OTHER INFORMATION: Synthetic

<400> SEQUENCE: 21
atatgggaag atggaagtaa taaa 24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Trp Glu Asp Gly Ser Asn Lys
1 5

<210> SEQ ID NO 23
<211> LENGTH: 63
<212> TYPE: DNA
<213> ORGANISM: Artificial Sequence
<220> FEATURE:
<223> OTHER INFORMATION: Synthetic

<400> SEQUENCE: 23
gcgagacaga ctatggttcg gggagttatc cgcttttact actactacta cggtatggac 60
gtc 63

<210> SEQ ID NO 24
<211> LENGTH: 21
<212> TYPE: PRT
<213> ORGANISM: Artificial Sequence
<220> FEATURE:
<223> OTHER INFORMATION: Synthetic

<400> SEQUENCE: 24

Ala Arg Gln Thr Met Val Arg Gly Val Ile Arg Phe Tyr Tyr Tyr Tyr
1 5 10 15

Tyr Gly Met Asp Val
20

<210> SEQ ID NO 25
<211> LENGTH: 336
<212> TYPE: DNA
<213> ORGANISM: Artificial Sequence
<220> FEATURE:
<223> OTHER INFORMATION: Synthetic

<400> SEQUENCE: 25
gatattgtga tgactcagtc tccactctcc ctgcccgtca cccctggaga gccggcctcc 60
atctcctgca ggtctagtca gagcctcctg tatagtaatg gatacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttgggttt tattactgca tgcaggctct acaaactcct 300
ccgacgttcg gccaagggac caaggtggag atcaaa 336

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu Tyr Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Phe Tyr Tyr Cys Met Gln Ala
85 90 95

Leu Gln Thr Pro Pro Thr Phe Gly Gln Gly Thr Lys Val Glu Ile Lys
100 105 110

<210> SEQ ID NO 27
<211> LENGTH: 33
<212> TYPE: DNA
<213> ORGANISM: Artificial Sequence
<220> FEATURE:
<223> OTHER INFORMATION: Synthetic

<400> SEQUENCE: 27
cagagcctcc tgtatagtaa tggatacaac tat 33

<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Gln Ser Leu Leu Tyr Ser Asn Gly Tyr Asn Tyr
1 5 10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 ttgggttct 9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Leu Gly Ser
1

<210> SEQ ID NO 31
<211> LENGTH: 27

<212> TYPE: DNA
<213> ORGANISM: Artificial Sequence
<220> FEATURE:
<223> OTHER INFORMATION: Synthetic

<400> SEQUENCE: 31
atgcaggctc tacaaactcc tccgacg 27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Met Gln Ala Leu Gln Thr Pro Pro Thr
1 5

<210> SEQ ID NO 33
<211> LENGTH: 354
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggagcc ttggttcagc ctggggggtc cctgagactc 60
tcctgtgcag cctctggatt cacctttagc aactatgcca tgacctgggt ccgccaggct 120
ccagggatgg gactggagtg ggtctcaggt attagtagta gtggtgctag cactttctac 180
gcagactccg tgaagggccg gttcaccatt tccagagaca attccaagaa cacgctgtat 240
ctacaaatga acagcctgag agccgaggac acggccgtat attattgtgc gaaagaagac 300
tattggggat ggtttgacta ctggggccag ggaaccctgg tcaccgtctc ctca 354

<210> SEQ ID NO 34
<211> LENGTH: 118
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Ala Leu Val Gln Pro Gly Gly
1 5 10 15

Ser Leu Arg Leu Ser Cys Ala Ala Ser Gly Phe Thr Phe Ser Asn Tyr
20 25 30

Ala Met Thr Trp Val Arg Gln Ala Pro Gly Met Gly Leu Glu Trp Val
35 40 45

Ser Gly Ile Ser Ser Ser Gly Ala Ser Thr Phe Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Asp Tyr Trp Gly Trp Phe Asp Tyr Trp Gly Gln Gly Thr
100 105 110

Leu Val Thr Val Ser Ser
115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct ttagcaacta tgcc 24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Asn Tyr Ala
1 5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
attagtagta gtggtgctag cact 24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Ser Ser Gly Ala Ser Thr
1 5

<210> SEQ ID NO 39
<211> LENGTH: 33
<212> TYPE: DNA
<213> ORGANISM: Artificial Sequence
<220> FEATURE:
<223> OTHER INFORMATION: Synthetic

<400> SEQUENCE: 39
gcgaaagaag actattgggg atggtttgac tac 33

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Ala Lys Glu Asp Tyr Trp Gly Trp Phe Asp Tyr
1 5 10

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccagt tgacccagtc tccatccttc ctgtctgcat ctgtaggaga cagagtcacc 60
atcacttgct gggccagtca ggacgttagc agttatttag cctggtatca gcaagaacca 120
gggaaagccc ctaaggtcct gatctatgat gcatccactt tgcaaagtgg ggtcccatca 180
aggttcagcg gcagtggatc tgggacagaa ttcactctca caatcagcag cctgcagcct 240
gaagattttg caccttatta ctgtcaacag cttaatagtt acccgtacac ttttggccag 300
gggaccaagc tggagatcaa a 321

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Asp Val Ser Ser Tyr
20 25 30

Leu Ala Trp Tyr Gln Gln Glu Pro Gly Lys Ala Pro Lys Val Leu Ile
35 40 45

Tyr Asp Ala Ser Thr Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Pro Tyr Tyr Cys Gln Gln Leu Asn Ser Tyr Pro Tyr
85 90 95

Thr Phe Gly Gln Gly Thr Lys Leu Glu Ile Lys
100 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
caggacgtta gcagttat 18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Asp Val Ser Ser Tyr
1 5

<210> SEQ ID NO 45
<211> LENGTH: 9
<212> TYPE: DNA
<213> ORGANISM: Artificial Sequence
<220> FEATURE:

<223> OTHER INFORMATION: Synthetic

<400> SEQUENCE: 45 gatgcatcc 9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Asp Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
caacagctta atagttaccc gtacact 27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Leu Asn Ser Tyr Pro Tyr Thr
1 5

<210> SEQ ID NO 49
<211> LENGTH: 363
<212> TYPE: DNA
<213> ORGANISM: Artificial Sequence
<220> FEATURE:
<223> OTHER INFORMATION: Synthetic

<400> SEQUENCE: 49
caggttcagc tggtgcagtc tagagatgag gtgaagaagc ctggggcctc agtgaaggtc 60
tcctgcaagg cttctggtta cacctttacc acctatggaa tcagctgggt gcgacaggcc 120
cctggacaag ggcttgagtg gatgggatgg atcaacactt acaatggtga cacaaactat 180
gcacagaagg tccaggacag agtcatcatg accacagaca catccacgag cacagcctac 240
atggagctga ggagcctgag atctgacgac acggccgtat atttttgtgc gggggcaaga 300
ccactaggtg gacggagggc ttttgatatc tggggccaag ggacaatggt caccgtctct 360
tca 363

<210> SEQ ID NO 50
<211> LENGTH: 121
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Gln Ser Arg Asp Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Asn Thr Tyr Asn Gly Asp Thr Asn Tyr Ala Gln Lys Val
    50                  55                  60

Gln Asp Arg Val Ile Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Gly Ala Arg Pro Leu Gly Gly Arg Arg Ala Phe Asp Ile Trp Gly
            100                 105                 110

Gln Gly Thr Met Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggttacacct ttaccaccta tgga 24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Tyr Thr Phe Thr Thr Tyr Gly
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atcaacactt acaatggtga caca 24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Asn Thr Tyr Asn Gly Asp Thr
1               5

<210> SEQ ID NO 55

<211> LENGTH: 42
<212> TYPE: DNA
<213> ORGANISM: Artificial Sequence
<220> FEATURE:
<223> OTHER INFORMATION: Synthetic

<400> SEQUENCE: 55
gcgggggcaa gaccactagg tggacggagg gcttttgata tc 42

<210> SEQ ID NO 56
<211> LENGTH: 14
<212> TYPE: PRT
<213> ORGANISM: Artificial Sequence
<220> FEATURE:
<223> OTHER INFORMATION: Synthetic

<400> SEQUENCE: 56

Ala Gly Ala Arg Pro Leu Gly Gly Arg Arg Ala Phe Asp Ile
1 5 10

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctcc ctgtctgcat ctgtaggaga cagagtcacc 60
atcacttgcc gggcgagtca gggcattagc cattatttag cctggtatca gcagaaacca 120
gggaaagttc ctaaactcct aatctatgct gcatccactt tacaatcagg ggtcccatct 180
cggttcagtg gcagtggatc tgggacagat ttcactctca ccatcagcag cctgcagcct 240
gaagatgttg caacttatta ctgtcaaaag tataacagtg tcccgtggac gttcggccaa 300
gggaccaagg tggaaatcaa a 321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser His Tyr
20 25 30

Leu Ala Trp Tyr Gln Gln Lys Pro Gly Lys Val Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Lys Tyr Asn Ser Val Pro Trp
85 90 95

Thr Phe Gly Gln Gly Thr Lys Val Glu Ile Lys
100 105

<210> SEQ ID NO 59
<211> LENGTH: 18

<212> TYPE: DNA
<213> ORGANISM: Artificial Sequence
<220> FEATURE:
<223> OTHER INFORMATION: Synthetic

<400> SEQUENCE: 59
cagggcatta gccattat 18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Ile Ser His Tyr
1 5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc 9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caaaagtata acagtgtccc gtggacg 27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Lys Tyr Asn Ser Val Pro Trp Thr
1 5

<210> SEQ ID NO 65
<211> LENGTH: 357
<212> TYPE: DNA
<213> ORGANISM: Artificial Sequence
<220> FEATURE:
<223> OTHER INFORMATION: Synthetic

<400> SEQUENCE: 65
caggtgcagc tggtggagtc tgggggaggc gtggtccagc ctgggaggtc cctgagactc 60
tcctgtgcag cgtctggatt caccttcagt aattatggca tggtctgggt ccgccaggct 120
ccaggcaagg ggctggagtg ggtggcattt atatggtatg atggaagtga taaatactat 180
gtagacgccg tgaagggccg attcaccatc tccagagaca attccaagaa cacgctgtat 240
ctgcaaatga acagcctgag agccgaggac acggctgtgt atttctgtgc gagaagcggc 300
ccgtccagac atgtttttga tatctggggc caagggacaa tggtcaccgt ctcttca 357

<210> SEQ ID NO 66
<211> LENGTH: 119
<212> TYPE: PRT
<213> ORGANISM: Artificial Sequence
<220> FEATURE:
<223> OTHER INFORMATION: Synthetic

<400> SEQUENCE: 66

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Gly Met Val Trp Val Arg Gln Ala Pro Gly Lys Gly Leu Glu Trp Val
35 40 45

Ala Phe Ile Trp Tyr Asp Gly Ser Asp Lys Tyr Tyr Val Asp Ala Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Phe Cys
85 90 95

Ala Arg Ser Gly Pro Ser Arg His Val Phe Asp Ile Trp Gly Gln Gly
100 105 110

Thr Met Val Thr Val Ser Ser
115

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacct tcagtaatta tggc 24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Asn Tyr Gly
1 5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
atatggtatg atggaagtga taaa 24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Trp Tyr Asp Gly Ser Asp Lys
1 5

<210> SEQ ID NO 71
<211> LENGTH: 36
<212> TYPE: DNA
<213> ORGANISM: Artificial Sequence
<220> FEATURE:
<223> OTHER INFORMATION: Synthetic

<400> SEQUENCE: 71
gcgagaagcg gcccgtccag acatgttttt gatatc 36

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72

Ala Arg Ser Gly Pro Ser Arg His Val Phe Asp Ile
1 5 10

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccttccacc ctgtctgcat ctgtaggaga cagagtcacc 60
atcacttgcc gggccagtca gagtattagt agttggttgg cctggtatca gcagaaacca 120
gggaaagccc ctaaactcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt attcgtacac ttttggccag 300
gggaccaagc tggagatcaa a 321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Ser Tyr
85 90 95

Thr Phe Gly Gln Gly Thr Lys Leu Glu Ile Lys
100 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagagtatta gtagttgg 18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Ser Ile Ser Ser Trp
1 5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 aaggcgtct 9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Lys Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacagtata atagttattc gtacact 27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Asn Ser Tyr Ser Tyr Thr
1 5

<210> SEQ ID NO 81
<211> LENGTH: 360
<212> TYPE: DNA
<213> ORGANISM: Artificial Sequence
<220> FEATURE:
<223> OTHER INFORMATION: Synthetic

<400> SEQUENCE: 81
caggtgcagc tggtggagtc tgggggaggc gtggtccagc ctgggaggtc cctgagactc 60
tcctgtgcag cgtctggatt caccttcaga aactatggca tgcactgggt ccgccaggct 120
ccaggcaagg ggctggagtg ggtggcagtt aaacggtatg atggaagtga tgaatatttt 180
gtagactccg tgaagggccg attcaccatc tccagagaca attccaagaa cacgcttttt 240
ctgcaaatga acagcctgag agtcgacgac acggctgtat attattgtgc gagagaaact 300
cctataactg gaactacgct tgactactgg ggccagggaa ccctggtcac cgtctcctca 360

<210> SEQ ID NO 82
<211> LENGTH: 120
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Arg Asn Tyr
20 25 30

Gly Met His Trp Val Arg Gln Ala Pro Gly Lys Gly Leu Glu Trp Val
35 40 45

Ala Val Lys Arg Tyr Asp Gly Ser Asp Glu Tyr Phe Val Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Val Asp Asp Thr Ala Val Tyr Tyr Cys
85 90 95

Ala Arg Glu Thr Pro Ile Thr Gly Thr Thr Leu Asp Tyr Trp Gly Gln
100 105 110

Gly Thr Leu Val Thr Val Ser Ser
115 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacct tcagaaacta tggc 24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Arg Asn Tyr Gly
1 5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
aaacggtatg atggaagtga tgaa 24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Lys Arg Tyr Asp Gly Ser Asp Glu
1 5

<210> SEQ ID NO 87
<211> LENGTH: 39
<212> TYPE: DNA
<213> ORGANISM: Artificial Sequence
<220> FEATURE:
<223> OTHER INFORMATION: Synthetic

<400> SEQUENCE: 87
gcgagagaaa ctcctataac tggaactacg cttgactac 39

<210> SEQ ID NO 88
<211> LENGTH: 13
<212> TYPE: PRT
<213> ORGANISM: Artificial Sequence
<220> FEATURE:
<223> OTHER INFORMATION: Synthetic

<400> SEQUENCE: 88

Ala Arg Glu Thr Pro Ile Thr Gly Thr Thr Leu Asp Tyr
1 5 10

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89

```
gacatccaga tgacccagtc tccatcctcc ctgtctgcat ctgtaggaga cagagtcacc     60
atcacttgcc ggacaagtca gagcattacc aactatttaa attggtatca acagaaacca    120
gggaaagccc ctaagctcct gatctatgct gcatccaggt cacaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa a                                              321
```

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Thr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Ser Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91

```
cagagcatta ccaactat                                                   18
```

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

```
Gln Ser Ile Thr Asn Tyr
1               5
```

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc 9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacagagtt acagtacccc gctcact 27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ser Thr Pro Leu Thr
1 5

<210> SEQ ID NO 97
<211> LENGTH: 360
<212> TYPE: DNA
<213> ORGANISM: Artificial Sequence
<220> FEATURE:
<223> OTHER INFORMATION: Synthetic

<400> SEQUENCE: 97
caggtgcagc tggtggagtc tgggggaggc gtgggccagc ctgggaggtc cctgagactc 60
tcctgtgtag cgtctggatt caccttcaga aactatggca tgcactgggt ccgccaggct 120
ccaggcaagg ggctggactg ggtggcaatt ataggatatg atggaagtaa agaatacaat 180
gtagactccg tgaagggccg ttttaccatc tccagagaca attccaagaa cacgctgtat 240
ctgcaaatga acagtctggg agccgaggac acggctatat attactgtgc gagagaaagt 300
cctataactg gaactacgtt tgactactgg ggccagggaa ccctggtcac cgtctcctca 360

<210> SEQ ID NO 98
<211> LENGTH: 120
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Glu Ser Gly Gly Gly Val Gly Gln Pro Gly Arg
1 5 10 15

Ser Leu Arg Leu Ser Cys Val Ala Ser Gly Phe Thr Phe Arg Asn Tyr
20 25 30

```
Gly Met His Trp Val Arg Gln Ala Pro Gly Lys Gly Leu Asp Trp Val
        35                  40                  45

Ala Ile Ile Gly Tyr Asp Gly Ser Lys Glu Tyr Asn Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Ile Tyr Tyr Cys
                85                  90                  95

Ala Arg Glu Ser Pro Ile Thr Gly Thr Thr Phe Asp Tyr Trp Gly Gln
            100                 105                 110

Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcacct tcagaaacta tggc                                             24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Arg Asn Tyr Gly
1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101

```
ataggatatg atggaagtaa agaa                                             24
```

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

```
Ile Gly Tyr Asp Gly Ser Lys Glu
1               5
```

<210> SEQ ID NO 103
<211> LENGTH: 39
<212> TYPE: DNA
<213> ORGANISM: Artificial Sequence
<220> FEATURE:
<223> OTHER INFORMATION: Synthetic

<400> SEQUENCE: 103
gcgagagaaa gtcctataac tggaactacg tttgactac 39

<210> SEQ ID NO 104
<211> LENGTH: 13
<212> TYPE: PRT
<213> ORGANISM: Artificial Sequence
<220> FEATURE:
<223> OTHER INFORMATION: Synthetic

<400> SEQUENCE: 104

Ala Arg Glu Ser Pro Ile Thr Gly Thr Thr Phe Asp Tyr
1 5 10

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccaccctcc ctgtctgcat ctgtaggaga cagagtcacc 60
atcacttgcc gggcaagtca gagcattggc aattatttaa attggtatca gcagaaacca 120
ggaaaagccc ctaagatcct gatctatgct gcatcccgtt tgcaaagtgg ggtcccatca 180
aggttcagtg gcagtggatc tgggacagat ttcactctca ccatcagtag tctgcaacct 240
gaagattttg caacttacta ctgtcaacag agttacagta ccccgctcac tttcggcgga 300
gggaccaagg tggagatcaa a 321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Pro Ser Leu Ser Ala Ser Val Gly
1 5 10 15

Asp Arg Val Thr Ile Thr Cys Arg Ala Ser Gln Ser Ile Gly Asn Tyr
20 25 30

Leu Asn Trp Tyr Gln Gln Lys Pro Gly Lys Ala Pro Lys Ile Leu Ile
35 40 45

Tyr Ala Ala Ser Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Leu
85 90 95

Thr Phe Gly Gly Gly Thr Lys Val Glu Ile Lys
100 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagagcattg gcaattat 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Gly Asn Tyr
1 5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc 9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacagagtt acagtacccc gctcact 27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Ser Tyr Ser Thr Pro Leu Thr
1 5

<210> SEQ ID NO 113
<211> LENGTH: 375
<212> TYPE: DNA
<213> ORGANISM: Artificial Sequence
<220> FEATURE:
<223> OTHER INFORMATION: Synthetic

<400> SEQUENCE: 113
caggtcacct tgaaggagtc tggtcctgtg ctggtgaaac ccacagagac cctcacgctg 60
acctgcaccg tctctgggtt ctcactcagc agtgctagaa tgggtgtgag ttggatccgt 120
cagcccccag ggaaggccct ggagtggctt gcacacattt tttcgactga cgaaaaatcc 180
tacagcacat ctctgaagag caggctctcc atctccaagg acacctccct aagccaggtg 240
gtccttatta tgaccaacat ggaccctgta gacacagcca catattactg tgcacggcgt 300
acaactatgg ccccttacta ttactactac ggtatggacg tctggggcca cgggaccacg 360
gtcaccgtct cctca 375

<210> SEQ ID NO 114
<211> LENGTH: 125
<212> TYPE: PRT
<213> ORGANISM: Artificial Sequence
<220> FEATURE:
<223> OTHER INFORMATION: Synthetic

<400> SEQUENCE: 114

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Ser Ser Ala
20 25 30

Arg Met Gly Val Ser Trp Ile Arg Gln Pro Pro Gly Lys Ala Leu Glu
35 40 45

Trp Leu Ala His Ile Phe Ser Thr Asp Glu Lys Ser Tyr Ser Thr Ser
50 55 60

Leu Lys Ser Arg Leu Ser Ile Ser Lys Asp Thr Ser Leu Ser Gln Val
65 70 75 80

Val Leu Ile Met Thr Asn Met Asp Pro Val Asp Thr Ala Thr Tyr Tyr
85 90 95

Cys Ala Arg Arg Thr Thr Met Ala Pro Tyr Tyr Tyr Tyr Tyr Gly Met
100 105 110

Asp Val Trp Gly His Gly Thr Thr Val Thr Val Ser Ser
115 120 125

<210> SEQ ID NO 115
<211> LENGTH: 30
<212> TYPE: DNA
<213> ORGANISM: Artificial Sequence
<220> FEATURE:
<223> OTHER INFORMATION: Synthetic

<400> SEQUENCE: 115
gggttctcac tcagcagtgc tagaatgggt 30

<210> SEQ ID NO 116
<211> LENGTH: 10
<212> TYPE: PRT
<213> ORGANISM: Artificial Sequence
<220> FEATURE:
<223> OTHER INFORMATION: Synthetic

<400> SEQUENCE: 116

Gly Phe Ser Leu Ser Ser Ala Arg Met Gly
1 5 10

<210> SEQ ID NO 117
<211> LENGTH: 21

<212> TYPE: DNA
<213> ORGANISM: Artificial Sequence
<220> FEATURE:
<223> OTHER INFORMATION: Synthetic

<400> SEQUENCE: 117 atttttcga ctgacgaaaa a 21

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

Ile Phe Ser Thr Asp Glu Lys
1 5

<210> SEQ ID NO 119
<211> LENGTH: 51
<212> TYPE: DNA
<213> ORGANISM: Artificial Sequence
<220> FEATURE:
<223> OTHER INFORMATION: Synthetic

<400> SEQUENCE: 119
gcacggcgta caactatggc cccttactat tactactacg gtatggacgt c 51

<210> SEQ ID NO 120
<211> LENGTH: 17
<212> TYPE: PRT
<213> ORGANISM: Artificial Sequence
<220> FEATURE:
<223> OTHER INFORMATION: Synthetic

<400> SEQUENCE: 120

Ala Arg Arg Thr Thr Met Ala Pro Tyr Tyr Tyr Tyr Tyr Gly Met Asp
1 5 10 15

Val

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gccatccaga tgacccagtc tccagcctcc ctgtctgcat ctgtaggaga cagagtcacc 60
atcacttgcc gggcaagtca gggcattaga aatgatttag gttggtatca gcagaaacca 120
gggaaagccc ctaagctcct gatctctgct gcatccagtt tgcaaagtgg ggtcccatca 180
aggttcagcg gcagtggatc tggcacagat ttcactctca ccatcagcag cctgcagcct 240
gaagattttg caacttatta ctgtctacaa gattacaagt atccgtggac gttcggccaa 300
gggaccaagg tggaaatcaa a 321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Ala Ile Gln Met Thr Gln Ser Pro Ala Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Lys Tyr Pro Trp
                85                  90                  95

Thr Phe Gly Gln Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagggcatta gaaatgat 18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Gly Ile Arg Asn Asp
1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 gctgcatcc 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Ala Ala Ser
1

<210> SEQ ID NO 127
<211> LENGTH: 27
<212> TYPE: DNA
<213> ORGANISM: Artificial Sequence
<220> FEATURE:

<223> OTHER INFORMATION: Synthetic

<400> SEQUENCE: 127
ctacaagatt acaagtatcc gtggacg 27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Leu Gln Asp Tyr Lys Tyr Pro Trp Thr
1 5

<210> SEQ ID NO 129
<211> LENGTH: 363
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc tgggggaggc ttggtacagc ctggggggtc cctgagactc 60
tcctgttcag tctctggatt catctttaaa aactatgcca tgaggtgggt ccgccaggct 120
ccagggaagg ggctggagtg ggtctcagga attagcggca gtggtggtat cacatactac 180
gccgactccg tgaggggccg ggtcaccatt tccagagaca attccaagaa caccctagat 240
cttcaaatga ccaacctgag agccgaggac acggccgttt attactgtgc gaaagctgaa 300
tatagcagct cgggtgccta ctttgactac tggggccagg gaaccctggt cactgtctcc 360
tca 363

<210> SEQ ID NO 130
<211> LENGTH: 121
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Val Gln Pro Gly Gly
1 5 10 15

Ser Leu Arg Leu Ser Cys Ser Val Ser Gly Phe Ile Phe Lys Asn Tyr
20 25 30

Ala Met Arg Trp Val Arg Gln Ala Pro Gly Lys Gly Leu Glu Trp Val
35 40 45

Ser Gly Ile Ser Gly Ser Gly Gly Ile Thr Tyr Tyr Ala Asp Ser Val
50 55 60

Arg Gly Arg Val Thr Ile Ser Arg Asp Asn Ser Lys Asn Thr Leu Asp
65 70 75 80

Leu Gln Met Thr Asn Leu Arg Ala Glu Asp Thr Ala Val Tyr Tyr Cys
85 90 95

Ala Lys Ala Glu Tyr Ser Ser Ser Gly Ala Tyr Phe Asp Tyr Trp Gly
100 105 110

Gln Gly Thr Leu Val Thr Val Ser Ser
115 120

<210> SEQ ID NO 131

<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcatct ttaaaaacta tgcc 24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Ile Phe Lys Asn Tyr Ala
1 5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attagcggca gtggtggtat caca 24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Gly Ser Gly Gly Ile Thr
1 5

<210> SEQ ID NO 135
<211> LENGTH: 42
<212> TYPE: DNA
<213> ORGANISM: Artificial Sequence
<220> FEATURE:
<223> OTHER INFORMATION: Synthetic

<400> SEQUENCE: 135
gcgaaagctg aatatagcag ctcgggtgcc tactttgact ac 42

<210> SEQ ID NO 136
<211> LENGTH: 14
<212> TYPE: PRT
<213> ORGANISM: Artificial Sequence
<220> FEATURE:
<223> OTHER INFORMATION: Synthetic

<400> SEQUENCE: 136

Ala Lys Ala Glu Tyr Ser Ser Ser Gly Ala Tyr Phe Asp Tyr
1 5 10

<210> SEQ ID NO 137
<211> LENGTH: 321
<212> TYPE: DNA
<213> ORGANISM: Artificial Sequence
<220> FEATURE:

<223> OTHER INFORMATION: Synthetic

<400> SEQUENCE: 137

```
gacatccaga tgacccagtc tccatcctcc ctgtctgcat ctgtaggaga cagagtcacc      60

atcacttgcc gggcaagtca gagcattcac aactatttaa attggtatct gcagagacca     120

gggaaagccc ctaagctcct ggtctatgct gcatccagtt tgcaaagtgg ggtcccgtca     180

aggttcagtg gccgtggatc tgggacagat ttcactctca ccatcagcag tctgcaacct     240

gaagattttg caacttacta ctgtcaacag agttacagtg ccccgtacag ttttggccag     300

gggaccaagc tggagatcaa a                                               321
```

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Asn Tyr
            20                  25                  30

Leu Asn Trp Tyr Leu Gln Arg Pro Gly Lys Ala Pro Lys Leu Leu Val
        35                  40                  45

Tyr Ala Ala Ser Ser Leu Gln Ser Gly Val Pro Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Tyr
                85                  90                  95

Ser Phe Gly Gln Gly Thr Lys Leu Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139

```
cagagcattc acaactat                                                    18
```

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

```
Gln Ser Ile His Asn Tyr
1               5
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacagagtt acagtgcccc gtacagt 27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Ser Tyr Ser Ala Pro Tyr Ser
1 5

<210> SEQ ID NO 145
<211> LENGTH: 354
<212> TYPE: DNA
<213> ORGANISM: Artificial Sequence
<220> FEATURE:
<223> OTHER INFORMATION: Synthetic

<400> SEQUENCE: 145
gaggtgcagc tggtggagtc tgggggaggc ttggtacagc cggggggtc cctgagactc 60 tcctgtgaag cctctggatt cacctttagc agatatgcca tgacctgggt ccgccaggct 120
ccagggaagg ggctggagtg ggtctcaggt attagtggta gtggtggtag cacattctac 180
gtagactccc tgcagggccg gttcaccctc tccagagaca attccaagca cacgctgttt 240
ctgcaaatga acagcctgag agccgaggac acggccatat attactgtgc gaaagagaac 300
acctatggtc actttgacta ctggggccag ggaaccctgg tcaccgtctc ctca 354

<210> SEQ ID NO 146
<211> LENGTH: 118
<212> TYPE: PRT
<213> ORGANISM: Artificial Sequence
<220> FEATURE:
<223> OTHER INFORMATION: Synthetic

<400> SEQUENCE: 146

Glu Val Gln Leu Val Glu Ser Gly Gly Gly Leu Val Gln Pro Gly Gly
1 5 10 15

```
Ser Leu Arg Leu Ser Cys Glu Ala Ser Gly Phe Thr Phe Ser Arg Tyr
            20                  25                  30

Ala Met Thr Trp Val Arg Gln Ala Pro Gly Lys Gly Leu Glu Trp Val
        35                  40                  45

Ser Gly Ile Ser Gly Ser Gly Gly Ser Thr Phe Tyr Val Asp Ser Leu
    50                  55                  60

Gln Gly Arg Phe Thr Leu Ser Arg Asp Asn Ser Lys His Thr Leu Phe
65                  70                  75                  80

Leu Gln Met Asn Ser Leu Arg Ala Glu Asp Thr Ala Ile Tyr Tyr Cys
                85                  90                  95

Ala Lys Glu Asn Thr Tyr Gly His Phe Asp Tyr Trp Gly Gln Gly Thr
            100                 105                 110

Leu Val Thr Val Ser Ser
        115


<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147

ggattcacct ttagcagata tgcc                                            24


<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Arg Tyr Ala
1               5


<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149

attagtggta gtggtggtag caca                                            24


<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Gly Ser Gly Gly Ser Thr
1               5


<210> SEQ ID NO 151
<211> LENGTH: 33
<212> TYPE: DNA
<213> ORGANISM: Artificial Sequence
<220> FEATURE:
<223> OTHER INFORMATION: Synthetic
```

<400> SEQUENCE: 151
gcgaaagaga acacctatgg tcactttgac tac 33

<210> SEQ ID NO 152
<211> LENGTH: 11
<212> TYPE: PRT
<213> ORGANISM: Artificial Sequence
<220> FEATURE:
<223> OTHER INFORMATION: Synthetic

<400> SEQUENCE: 152

Ala Lys Glu Asn Thr Tyr Gly His Phe Asp Tyr
1 5 10

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccagt tgacccagtc tccatccttc ctgtctgcat ctgtaggaga cagagtcacc 60
atcacttgct gggccagtca ggacattagc acttatttag cctggtatca gcaaaaacca 120
gggaaagccc ctcaggtcct gatctatgct gcttcctctt tgcaatatgg ggtcccatct 180
aggttcagcg gcagtggatc tgggacagaa ttcactctca caatcaccag cctgcagcct 240
gaagattttg caacttatta ctgtcaacaa cttattggtt acccgtacat ttttggccag 300
gggaccaagc tggagatcaa a 321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Asp Ile Ser Thr Tyr
20 25 30

Leu Ala Trp Tyr Gln Gln Lys Pro Gly Lys Ala Pro Gln Val Leu Ile
35 40 45

Tyr Ala Ala Ser Ser Leu Gln Tyr Gly Val Pro Ser Arg Phe Ser Gly
50 55 60

Ser Gly Ser Gly Thr Glu Phe Thr Leu Thr Ile Thr Ser Leu Gln Pro
65 70 75 80

Glu Asp Phe Ala Thr Tyr Tyr Cys Gln Gln Leu Ile Gly Tyr Pro Tyr
85 90 95

Ile Phe Gly Gln Gly Thr Lys Leu Glu Ile Lys
100 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
caggacatta gcacttat 18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Asp Ile Ser Thr Tyr
1 5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gctgcttcc 9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacaactta ttggttaccc gtacatt 27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Leu Ile Gly Tyr Pro Tyr Ile
1 5

<210> SEQ ID NO 161
<211> LENGTH: 345
<212> TYPE: DNA
<213> ORGANISM: Artificial Sequence
<220> FEATURE:
<223> OTHER INFORMATION: Synthetic

<400> SEQUENCE: 161

```
caggtgcagc tggtggagtc tgggggaggc gtggtccagc ctgggaggtc cctgagactc      60

tcctgtgtag cgtctggatt taccttcagt aactatggca tgcactgggt ccgccaggct     120

ccaggcaagg gactggagtg ggtggcactt atatggtatg atggaagtaa taaatacttt     180

gcagactccg tgaagggccg attcaccatc tccagagaca attccaagag aatgatgttt     240

ctggaaatga acagcctgag agccgaggac acggctatat attactgtac gcgggatcga     300

ttgtttgact tctggggcca gggaaccctg gtcactgtct cctca                    345
```

<210> SEQ ID NO 162
<211> LENGTH: 115
<212> TYPE: PRT
<213> ORGANISM: Artificial Sequence
<220> FEATURE:
<223> OTHER INFORMATION: Synthetic

<400> SEQUENCE: 162

```
Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Ser Asn Lys Tyr Phe Ala Asp Ser Val
    50                  55                  60

Lys Gly Arg Phe Thr Ile Ser Arg Asp Asn Ser Lys Arg Met Met Phe
65                  70                  75                  80

Leu Glu Met Asn Ser Leu Arg Ala Glu Asp Thr Ala Ile Tyr Tyr Cys
                85                  90                  95

Thr Arg Asp Arg Leu Phe Asp Phe Trp Gly Gln Gly Thr Leu Val Thr
            100                 105                 110

Val Ser Ser
        115
```

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163

```
ggatttacct tcagtaacta tggc                                             24
```

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

```
Gly Phe Thr Phe Ser Asn Tyr Gly
1               5
```

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
atatggtatg atggaagtaa taaa 24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Trp Tyr Asp Gly Ser Asn Lys
1 5

<210> SEQ ID NO 167
<211> LENGTH: 24
<212> TYPE: DNA
<213> ORGANISM: Artificial Sequence
<220> FEATURE:
<223> OTHER INFORMATION: Synthetic

<400> SEQUENCE: 167
acgcgggatc gattgtttga cttc 24

<210> SEQ ID NO 168
<211> LENGTH: 8
<212> TYPE: PRT
<213> ORGANISM: Artificial Sequence
<220> FEATURE:
<223> OTHER INFORMATION: Synthetic

<400> SEQUENCE: 168

Thr Arg Asp Arg Leu Phe Asp Phe
1 5

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169
gccatccaga tgacccagtc tccatcctcc ctgtctgcat ctgtgggaga cagagtcagc 60
atcacttgcc gggcaagtca ggacattaga catgatctag gttggtttca tcagaaacca 120
gggaaagccc ctaaactcct gatctatgct gcatccactt tacaaagtgg ggtcccatca 180
aggtttggcg gcagtggatc tggcacagat ttcactctca ccatcaccag cctgcagcct 240
gaggattttg gaacttatta ctgtctacaa gattacaatt atccggccac cttcggccaa 300
gggacacgac tggagattaa a 321

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Ala Ile Gln Met Thr Gln Ser Pro Ser Ser Leu Ser Ala Ser Val Gly
1 5 10 15

```
Asp Arg Val Ser Ile Thr Cys Arg Ala Ser Gln Asp Ile Arg His Asp
            20                  25                  30

Leu Gly Trp Phe His Gln Lys Pro Gly Lys Ala Pro Lys Leu Leu Ile
        35                  40                  45

Tyr Ala Ala Ser Thr Leu Gln Ser Gly Val Pro Ser Arg Phe Gly Gly
    50                  55                  60

Ser Gly Ser Gly Thr Asp Phe Thr Leu Thr Ile Thr Ser Leu Gln Pro
65                  70                  75                  80

Glu Asp Phe Gly Thr Tyr Tyr Cys Leu Gln Asp Tyr Asn Tyr Pro Ala
                85                  90                  95

Thr Phe Gly Gln Gly Thr Arg Leu Glu Ile Lys
            100                 105


<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

caggacatta gacatgat                                                  18


<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Asp Ile Arg His Asp
1               5


<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

gctgcatcc                                                             9


<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1


<210> SEQ ID NO 175
<211> LENGTH: 27
<212> TYPE: DNA
<213> ORGANISM: Artificial Sequence
<220> FEATURE:
<223> OTHER INFORMATION: Synthetic
```

<400> SEQUENCE: 175
ctacaagatt acaattatcc ggccacc 27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Leu Gln Asp Tyr Asn Tyr Pro Ala Thr
1 5

<210> SEQ ID NO 177
<211> LENGTH: 354
<212> TYPE: DNA
<213> ORGANISM: Artificial Sequence
<220> FEATURE:
<223> OTHER INFORMATION: Synthetic

<400> SEQUENCE: 177
gaggtgcagc tggtggagtc tgggggaggc ttggttcagc ctggggggtc cctaagactc 60
tcctgtgcag cctctggatt cacctttacc acatatttca tgagttgggt ccgccaggct 120
ccagggaagg gactggagtg ggtctcaggt attagtggta gtgggactag tacattctat 180
gtagactcca tgaagggccg gttcaccatc tccagagaca attccaagaa tacgctatat 240
ctgcaaatga acagtctgag agtcgaggac acggccgtat atttctgtgc gaaagagaac 300
acctatggtc attttgactt ctggggccag ggaaccctgg tcactgtctc ctca 354

<210> SEQ ID NO 178
<211> LENGTH: 118
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Thr Tyr
20 25 30

Phe Met Ser Trp Val Arg Gln Ala Pro Gly Lys Gly Leu Glu Trp Val
35 40 45

Ser Gly Ile Ser Gly Ser Gly Thr Ser Thr Phe Tyr Val Asp Ser Met
50 55 60

Lys Gly Arg Phe Thr Ile Ser Arg Asp Asn Ser Lys Asn Thr Leu Tyr
65 70 75 80

Leu Gln Met Asn Ser Leu Arg Val Glu Asp Thr Ala Val Tyr Phe Cys
85 90 95

Ala Lys Glu Asn Thr Tyr Gly His Phe Asp Phe Trp Gly Gln Gly Thr
100 105 110

Leu Val Thr Val Ser Ser
115

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct ttaccacata tttc 24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Thr Thr Tyr Phe
1 5

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
attagtggta gtgggactag taca 24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Gly Ser Gly Thr Ser Thr
1 5

<210> SEQ ID NO 183
<211> LENGTH: 33
<212> TYPE: DNA
<213> ORGANISM: Artificial Sequence
<220> FEATURE:
<223> OTHER INFORMATION: Synthetic

<400> SEQUENCE: 183
gcgaaagaga acacctatgg tcattttgac ttc 33

<210> SEQ ID NO 184
<211> LENGTH: 11
<212> TYPE: PRT
<213> ORGANISM: Artificial Sequence
<220> FEATURE:
<223> OTHER INFORMATION: Synthetic

<400> SEQUENCE: 184

Ala Lys Glu Asn Thr Tyr Gly His Phe Asp Phe
1 5 10

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185
gacatccagt tgacccagtc tccatccttc ctgtctgcat ctgtaggaga cagagtcacc 60
atcacttgct gggccagtca ggacattagc agtcatttag cctggtatca gcaaaaacca 120
gggaaagccc ctaaggtcct gatctatgat gcatccactt tgcaaagtgg ggtcccatca 180
aggatcagcg gcagtggatc tgggacagaa ttcactctca caatcagcag cctgcagcct 240
gaagattttg cagcttatta ctgtcaacag cttgatggtt acccgtacac ttttggccag 300
gggaccaagc tggagatcaa a 321

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Asp Ile Ser Ser His
20 25 30

Leu Ala Trp Tyr Gln Gln Lys Pro Gly Lys Ala Pro Lys Val Leu Ile
35 40 45

Tyr Asp Ala Ser Thr Leu Gln Ser Gly Val Pro Ser Arg Ile Ser Gly
50 55 60

Ser Gly Ser Gly Thr Glu Phe Thr Leu Thr Ile Ser Ser Leu Gln Pro
65 70 75 80

Glu Asp Phe Ala Ala Tyr Tyr Cys Gln Gln Leu Asp Gly Tyr Pro Tyr
85 90 95

Thr Phe Gly Gln Gly Thr Lys Leu Glu Ile Lys
100 105

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
caggacatta gcagtcat 18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Asp Ile Ser Ser His
1 5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gatgcatcc 9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Asp Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacagcttg atggttaccc gtacact 27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Leu Asp Gly Tyr Pro Tyr Thr
1 5

<210> SEQ ID NO 193
<211> LENGTH: 369
<212> TYPE: DNA
<213> ORGANISM: Artificial Sequence
<220> FEATURE:
<223> OTHER INFORMATION: Synthetic

<400> SEQUENCE: 193
caggtacagc tgcagcagtc aggtccagga ctggtgaagc cctcgcagac cctctcactc 60
acctgtgcca tctccgggga cagtgtctct agcaacagtg ttgcttggaa ctggatcagg 120
cagtccccat cgagaggcct tgagtggctg ggaaggactt actacaggtc caactggtat 180
aatacttatg cagtatctgt gaaaagtcga ataaccatcg acccagacac atccaagaac 240
cagttctccc tgcagctgaa ctctgtgact cccgaggaca cggctctgta ttactgtgca 300
agagggcacc ggtatagtgg gagctacttt gactactggg gccagggaac cctggtcacc 360
gtctcctca 369

<210> SEQ ID NO 194
<211> LENGTH: 123
<212> TYPE: PRT
<213> ORGANISM: Artificial Sequence
<220> FEATURE:
<223> OTHER INFORMATION: Synthetic

<400> SEQUENCE: 194

Gln Val Gln Leu Gln Gln Ser Gly Pro Gly Leu Val Lys Pro Ser Gln
1 5 10 15

```
Thr Leu Ser Leu Thr Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Asn Trp Tyr Asn Thr Tyr Ala
    50                  55                  60

Val Ser Val Lys Ser Arg Ile Thr Ile Asp Pro Asp Thr Ser Lys Asn
65                  70                  75                  80

Gln Phe Ser Leu Gln Leu Asn Ser Val Thr Pro Glu Asp Thr Ala Leu
                85                  90                  95

Tyr Tyr Cys Ala Arg Gly His Arg Tyr Ser Gly Ser Tyr Phe Asp Tyr
            100                 105                 110

Trp Gly Gln Gly Thr Leu Val Thr Val Ser Ser
        115                 120


<210> SEQ ID NO 195
<211> LENGTH: 30
<212> TYPE: DNA
<213> ORGANISM: Artificial Sequence
<220> FEATURE:
<223> OTHER INFORMATION: Synthetic

<400> SEQUENCE: 195

ggggacagtg tctctagcaa cagtgttgct                                      30


<210> SEQ ID NO 196
<211> LENGTH: 10
<212> TYPE: PRT
<213> ORGANISM: Artificial Sequence
<220> FEATURE:
<223> OTHER INFORMATION: Synthetic

<400> SEQUENCE: 196

Gly Asp Ser Val Ser Ser Asn Ser Val Ala
1               5                   10


<210> SEQ ID NO 197
<211> LENGTH: 27
<212> TYPE: DNA
<213> ORGANISM: Artificial Sequence
<220> FEATURE:
<223> OTHER INFORMATION: Synthetic

<400> SEQUENCE: 197

acttactaca ggtccaactg gtataat                                         27


<210> SEQ ID NO 198
<211> LENGTH: 9
<212> TYPE: PRT
<213> ORGANISM: Artificial Sequence
<220> FEATURE:
<223> OTHER INFORMATION: Synthetic

<400> SEQUENCE: 198

Thr Tyr Tyr Arg Ser Asn Trp Tyr Asn
1               5


<210> SEQ ID NO 199
<211> LENGTH: 39
<212> TYPE: DNA
<213> ORGANISM: Artificial Sequence
<220> FEATURE:
<223> OTHER INFORMATION: Synthetic
```

<400> SEQUENCE: 199
gcaagagggc accggtatag tgggagctac tttgactac 39

<210> SEQ ID NO 200
<211> LENGTH: 13
<212> TYPE: PRT
<213> ORGANISM: Artificial Sequence
<220> FEATURE:
<223> OTHER INFORMATION: Synthetic

<400> SEQUENCE: 200

Ala Arg Gly His Arg Tyr Ser Gly Ser Tyr Phe Asp Tyr
1 5 10

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccatcctcc ctgtctgcat ctgtagggga cagagtcacc 60
atcacttgcc gggcaagtca gaacattaac agctatttca attggtatca gcagaaacca 120
gggaaagccc ctaagctcct gatctatgct gcatccagtt tgcaaagtgg ggtcccatca 180
aggttcagtg gcggtggatc tgggacagat ttcactctca ccatcagcag tctgcaacct 240
gaagattttg caacttacta ctgtcaacag acttacacta tcccgtggac gttcggccaa 300
gggaccaagg tggaaatcaa a 321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Asn Ser Tyr
20 25 30

Phe Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Gly Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Thr Ile Pro Trp
85 90 95

Thr Phe Gly Gln Gly Thr Lys Val Glu Ile Lys
100 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagaacatta acagctat 18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Asn Ile Asn Ser Tyr
1 5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gctgcatcc 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagactt acactatccc gtggacg 27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Thr Tyr Thr Ile Pro Trp Thr
1 5

<210> SEQ ID NO 209
<211> LENGTH: 363
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ttggtaaagc ctggggggtc ccttagactc 60
tcctgtgcag cctctggatt cactttcagt aacgcctgga tgagttgggt ccgccaggct 120
ccagggaagg gactggagtg ggttggccgt attaaaagca aaactgatgg tgggacatca 180
gaatacgctg cacccgtgaa aggcagattc accatctcaa gagacgattc aaaaaacacg 240
ctgtttctgc aaatgaatag cctgaaaagc gaggacgcgg ccgtgtatta ctgcaccaca 300
ggacgcagct ggtctgacta ctttgacttc tggggccagg gaaccctggt caccgtctcc 360
tca 363

<210> SEQ ID NO 210
<211> LENGTH: 121
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asn Ala
20 25 30

Trp Met Ser Trp Val Arg Gln Ala Pro Gly Lys Gly Leu Glu Trp Val
35 40 45

Gly Arg Ile Lys Ser Lys Thr Asp Gly Gly Thr Ser Glu Tyr Ala Ala
50 55 60

Pro Val Lys Gly Arg Phe Thr Ile Ser Arg Asp Asp Ser Lys Asn Thr
65 70 75 80

Leu Phe Leu Gln Met Asn Ser Leu Lys Ser Glu Asp Ala Ala Val Tyr
85 90 95

Tyr Cys Thr Thr Gly Arg Ser Trp Ser Asp Tyr Phe Asp Phe Trp Gly
100 105 110

Gln Gly Thr Leu Val Thr Val Ser Ser
115 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcactt tcagtaacgc ctgg 24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Asn Ala Trp
1 5

<210> SEQ ID NO 213
<211> LENGTH: 30

<212> TYPE: DNA
<213> ORGANISM: Artificial Sequence
<220> FEATURE:
<223> OTHER INFORMATION: Synthetic

<400> SEQUENCE: 213
attaaaagca aaactgatgg tgggacatca 30

<210> SEQ ID NO 214
<211> LENGTH: 10
<212> TYPE: PRT
<213> ORGANISM: Artificial Sequence
<220> FEATURE:
<223> OTHER INFORMATION: Synthetic

<400> SEQUENCE: 214

Ile Lys Ser Lys Thr Asp Gly Gly Thr Ser
1 5 10

<210> SEQ ID NO 215
<211> LENGTH: 36
<212> TYPE: DNA
<213> ORGANISM: Artificial Sequence
<220> FEATURE:
<223> OTHER INFORMATION: Synthetic

<400> SEQUENCE: 215
accacaggac gcagctggtc tgactacttt gacttc 36

<210> SEQ ID NO 216
<211> LENGTH: 12
<212> TYPE: PRT
<213> ORGANISM: Artificial Sequence
<220> FEATURE:
<223> OTHER INFORMATION: Synthetic

<400> SEQUENCE: 216

Thr Thr Gly Arg Ser Trp Ser Asp Tyr Phe Asp Phe
1 5 10

<210> SEQ ID NO 217
<211> LENGTH: 321
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccatcctcc ctgtctgcat ctgtaggaga cagagtcacc 60
atcacttgcc aggcgagtca ggacattagc aactatttaa attggtatca gcagaaacca 120
gggaaagccc ctaagctcct gatctacgat gcatccaact tggaaacagg ggtcccatca 180
aggttcagtg gaagtggatt tgcgacagat tttactttca ccatcagcag cctgcagcct 240
gaagatattg caacatatta ctgtcaacac tatgatgatc tcccattcac tttcggccct 300
gggaccaaag tggatatcaa a 321

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Phe Ala Thr Asp Phe Thr Phe Thr Ile Ser Ser Leu Gln Pro
65                  70                  75                  80

Glu Asp Ile Ala Thr Tyr Tyr Cys Gln His Tyr Asp Asp Leu Pro Phe
                85                  90                  95

Thr Phe Gly Pro Gly Thr Lys Val Asp Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
caggacatta gcaactat 18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

```
Gln Asp Ile Ser Asn Tyr
1               5
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 gatgcatcc 9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

```
Asp Ala Ser
1
```

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacactatg atgatctccc attcact 27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln His Tyr Asp Asp Leu Pro Phe Thr
1 5

<210> SEQ ID NO 225
<211> LENGTH: 366
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtacagt ctgggggggtc cctgagactc 60 tcttgtgtag cctctggatt cacctttagc acctatgcca tgacctgggt ccgccaggct 120
ccagggaggg ggctggagtg ggtctcagct attagtggta gtggtgctag cacatactac 180
gcagactcct tgaagggccg gttcaccgtc tccagagaca attccaagaa cacgctgtat 240
ctgcaaatga acagcctgag agccgaggac acggccgtat attactgttc gaaagatcac 300
cggaactacg actccgacta cgacatggac gtctggggcc aaggaaccac ggtcaccgtc 360
tcctca 366

<210> SEQ ID NO 226
<211> LENGTH: 122
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Ser Gly Gly
1 5 10 15

Ser Leu Arg Leu Ser Cys Val Ala Ser Gly Phe Thr Phe Ser Thr Tyr
20 25 30

Ala Met Thr Trp Val Arg Gln Ala Pro Gly Arg Gly Leu Glu Trp Val
35 40 45

Ser Ala Ile Ser Gly Ser Gly Ala Ser Thr Tyr Tyr Ala Asp Ser Leu
50 55 60

Lys Gly Arg Phe Thr Val Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ser Lys Asp His Arg Asn Tyr Asp Ser Asp Tyr Asp Met Asp Val Trp
100 105 110

Gly Gln Gly Thr Thr Val Thr Val Ser Ser
115 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct ttagcaccta tgcc 24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Phe Ser Thr Tyr Ala
1 5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtggta gtggtgctag caca 24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Gly Ser Gly Ala Ser Thr
1 5

<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231
tcgaaagatc accggaacta cgactccgac tacgacatgg acgtc 45

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Ser Lys Asp His Arg Asn Tyr Asp Ser Asp Tyr Asp Met Asp Val
1 5 10 15

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233
gacatccaga tgacccagtc tccatcctcc ctgtctgctt ctgtaggaga cagagtcacc 60
atcacttgcc gggcaagtca gggcattaga aattatttag gctggtatca gcagaaacca 120
gggaaagccc ctaagcgcct gatctatact gcatccagtt tgcagagtgg ggtcccatca 180
agattccgcg gcagtggatc tgggacagaa ttcactctca caatcagcag cctgcagcct 240
gaagattttg caacttatta ctgtctacaa cataatagtt acccgtacac ttttggccag 300
gggaccaagc tggagatcaa a 321

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Tyr
20 25 30

Leu Gly Trp Tyr Gln Gln Lys Pro Gly Lys Ala Pro Lys Arg Leu Ile
35 40 45

Tyr Thr Ala Ser Ser Leu Gln Ser Gly Val Pro Ser Arg Phe Arg Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln His Asn Ser Tyr Pro Tyr
85 90 95

Thr Phe Gly Gln Gly Thr Lys Leu Glu Ile Lys
100 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagggcatta gaaattat 18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Gly Ile Arg Asn Tyr
1 5

<210> SEQ ID NO 237
<211> LENGTH: 9
<212> TYPE: DNA
<213> ORGANISM: Artificial Sequence
<220> FEATURE:

<223> OTHER INFORMATION: Synthetic

<400> SEQUENCE: 237 actgcatcc 9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Thr Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
ctacaacata atagttaccc gtacact 27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Leu Gln His Asn Ser Tyr Pro Tyr Thr
1 5

<210> SEQ ID NO 241
<211> LENGTH: 372
<212> TYPE: DNA
<213> ORGANISM: Artificial Sequence
<220> FEATURE:
<223> OTHER INFORMATION: Synthetic

<400> SEQUENCE: 241
caggtgcagc tggtggagtc tgggggaggc gtggtccagc ctgggaggtc cctgagactc 60
tcctgtgcag cgtctggatt caccttcaat aactatgtta tgcactgggt ccgccaggct 120
ccaggcaagg ggctggagtg ggtggcactt atatggtatg atggaagtaa taaatactat 180
gcagactccg tgaagggccg attcaccatc tccagagaca attccaagaa cgcgctgaat 240
ctgcaaatga acagcctgag agccgaggac acggctgtgt atttttgtgc gagagtctct 300
atagcagctc gaaactacta ctacggcggt ttggacgtct ggggccaagg aaccacggtc 360
accgtctcct ca 372

<210> SEQ ID NO 242
<211> LENGTH: 124
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Val Met His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Ala Leu Asn
65                  70                  75                  80

Leu Gln Met Asn Ser Leu Arg Ala Glu Asp Thr Ala Val Tyr Phe Cys
                85                  90                  95

Ala Arg Val Ser Ile Ala Ala Arg Asn Tyr Tyr Tyr Gly Gly Leu Asp
            100                 105                 110

Val Trp Gly Gln Gly Thr Thr Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcaataacta tgtt 24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Asn Asn Tyr Val
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatggtatg atggaagtaa taaa 24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Trp Tyr Asp Gly Ser Asn Lys
1               5

<210> SEQ ID NO 247

<211> LENGTH: 51
<212> TYPE: DNA
<213> ORGANISM: Artificial Sequence
<220> FEATURE:
<223> OTHER INFORMATION: Synthetic

<400> SEQUENCE: 247
gcgagagtct ctatagcagc tcgaaactac tactacggcg gtttggacgt c 51

<210> SEQ ID NO 248
<211> LENGTH: 17
<212> TYPE: PRT
<213> ORGANISM: Artificial Sequence
<220> FEATURE:
<223> OTHER INFORMATION: Synthetic

<400> SEQUENCE: 248

Ala Arg Val Ser Ile Ala Ala Arg Asn Tyr Tyr Tyr Gly Gly Leu Asp
1 5 10 15

Val

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249
gaaatagtgt tgacacagtc tccaggcacc ctgtctttgt ctccagggga aagagccacc 60
ctctcctgca gggccagtca gagtgttagc agcacctact tagcctggta ccaacagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cattatggtg gctcaccgct cactttcggc 300
ggagggacca aggtggagat caaa 324

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Thr
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln His Tyr Gly Gly Ser Pro
85 90 95

Leu Thr Phe Gly Gly Gly Thr Lys Val Glu Ile Lys
100 105

<210> SEQ ID NO 251
<211> LENGTH: 21
<212> TYPE: DNA
<213> ORGANISM: Artificial Sequence
<220> FEATURE:
<223> OTHER INFORMATION: Synthetic

<400> SEQUENCE: 251
cagagtgtta gcagcaccta c 21

<210> SEQ ID NO 252
<211> LENGTH: 7
<212> TYPE: PRT
<213> ORGANISM: Artificial Sequence
<220> FEATURE:
<223> OTHER INFORMATION: Synthetic

<400> SEQUENCE: 252

Gln Ser Val Ser Ser Thr Tyr
1 5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ggtgcatcc 9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Gly Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
cagcattatg gtggctcacc gctcact 27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln His Tyr Gly Gly Ser Pro Leu Thr
1 5

<210> SEQ ID NO 257
<211> LENGTH: 357
<212> TYPE: DNA
<213> ORGANISM: Artificial Sequence
<220> FEATURE:
<223> OTHER INFORMATION: Synthetic

<400> SEQUENCE: 257
caggtgcagc tggtggagtc tgggggaggc gtggtccagc ctgggaggtc cctgagactc 60
tcctgtgaag cgtctggatt caccttccgt aactatggca tgcactgggt ccgccaggct 120
ccaggcaagg ggctggactg ggtgtcaact atttactatg atggaagtga tgaatactat 180
tcagactccg tgaagggccg attcaccatc tccagagaca attccaagaa cacgctgtat 240
ttgcaaatga acagcctgag agccgaggac acggctgtgt attactgtgc gagagatccc 300
cctagttttc ggtactttga ctactggggc cagggaaccc tggtcaccgt ctcctca 357

<210> SEQ ID NO 258
<211> LENGTH: 119
<212> TYPE: PRT
<213> ORGANISM: Artificial Sequence
<220> FEATURE:
<223> OTHER INFORMATION: Synthetic

<400> SEQUENCE: 258

Gln Val Gln Leu Val Glu Ser Gly Gly Gly Val Val Gln Pro Gly Arg
1 5 10 15

Ser Leu Arg Leu Ser Cys Glu Ala Ser Gly Phe Thr Phe Arg Asn Tyr
20 25 30

Gly Met His Trp Val Arg Gln Ala Pro Gly Lys Gly Leu Asp Trp Val
35 40 45

Ser Thr Ile Tyr Tyr Asp Gly Ser Asp Glu Tyr Tyr Ser Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Pro Pro Ser Phe Arg Tyr Phe Asp Tyr Trp Gly Gln Gly
100 105 110

Thr Leu Val Thr Val Ser Ser
115

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcacct tccgtaacta tggc 24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Arg Asn Tyr Gly
1 5

<210> SEQ ID NO 261
<211> LENGTH: 24

<212> TYPE: DNA
<213> ORGANISM: Artificial Sequence
<220> FEATURE:
<223> OTHER INFORMATION: Synthetic

<400> SEQUENCE: 261
atttactatg atggaagtga tgaa 24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Tyr Tyr Asp Gly Ser Asp Glu
1 5

<210> SEQ ID NO 263
<211> LENGTH: 36
<212> TYPE: DNA
<213> ORGANISM: Artificial Sequence
<220> FEATURE:
<223> OTHER INFORMATION: Synthetic

<400> SEQUENCE: 263
gcgagagatc cccctagttt tcggtacttt gactac 36

<210> SEQ ID NO 264
<211> LENGTH: 12
<212> TYPE: PRT
<213> ORGANISM: Artificial Sequence
<220> FEATURE:
<223> OTHER INFORMATION: Synthetic

<400> SEQUENCE: 264

Ala Arg Asp Pro Pro Ser Phe Arg Tyr Phe Asp Tyr
1 5 10

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccttccacc ctgtctgcat ctgtaggaga cagagtcacc 60
atcacttgcc gggccagtca gagcattcgt agctggttga cctggtatca gcagaaacca 120
gggaaagccc ctaaggtcct gatctataag gcgtctactt tagaacgtgg ggtcccatca 180
aggttcagtg gcagtggatc tgggacagaa ttcactctca ccatcagcag cctgcagcct 240
gaggattttg caacttatta ctgccatcag tacagtagtt attcgtacac ttttggccag 300
gggaccaagc tggagatcaa a 321

<210> SEQ ID NO 266
<211> LENGTH: 107
<212> TYPE: PRT
<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Arg Ser Trp
            20                  25                  30

Leu Thr Trp Tyr Gln Gln Lys Pro Gly Lys Ala Pro Lys Val Leu Ile
        35                  40                  45

Tyr Lys Ala Ser Thr Leu Glu Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys His Gln Tyr Ser Ser Tyr Ser Tyr
                85                  90                  95

Thr Phe Gly Gln Gly Thr Lys Leu Glu Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
cagagcattc gtagctgg 18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

Gln Ser Ile Arg Ser Trp
1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 aaggcgtct 9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Lys Ala Ser
1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
catcagtaca gtagttattc gtacact 27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

His Gln Tyr Ser Ser Tyr Ser Tyr Thr
1 5

<210> SEQ ID NO 273
<211> LENGTH: 369
<212> TYPE: DNA
<213> ORGANISM: Artificial Sequence
<220> FEATURE:
<223> OTHER INFORMATION: Synthetic

<400> SEQUENCE: 273
caggtgcagc tggtggagtc tgggggaggc gtggtccagc ctgggaggtc cctgagactc 60
tcctgtacag cctctggatt caccttcgat aactatggca tgcactgggt ccgccaggct 120
ccaggcaaag gcctggagtg ggtggcagtt atttcatatg atggaagtaa tacattctat 180
gcagactccg tgaagggccg attcaccatc tccagagaca attccaagaa cgcgctgtat 240
ctgcaaatga acagcctgag agctgaggac acggctgttt attactgtgc gaaagatctt 300
gaattcgata ttttgattgg ttatcccttt gactcctggg gccggggaac cctggtcact 360
gtctcctca 369

<210> SEQ ID NO 274
<211> LENGTH: 123
<212> TYPE: PRT
<213> ORGANISM: Artificial Sequence
<220> FEATURE:
<223> OTHER INFORMATION: Synthetic

<400> SEQUENCE: 274

Gln Val Gln Leu Val Glu Ser Gly Gly Gly Val Val Gln Pro Gly Arg
1 5 10 15

Ser Leu Arg Leu Ser Cys Thr Ala Ser Gly Phe Thr Phe Asp Asn Tyr
20 25 30

Gly Met His Trp Val Arg Gln Ala Pro Gly Lys Gly Leu Glu Trp Val
35 40 45

Ala Val Ile Ser Tyr Asp Gly Ser Asn Thr Phe Tyr Ala Asp Ser Val
50 55 60

Lys Gly Arg Phe Thr Ile Ser Arg Asp Asn Ser Lys Asn Ala Leu Tyr
65 70 75 80

Leu Gln Met Asn Ser Leu Arg Ala Glu Asp Thr Ala Val Tyr Tyr Cys
85 90 95

Ala Lys Asp Leu Glu Phe Asp Ile Leu Ile Gly Tyr Pro Phe Asp Ser
100 105 110

Trp Gly Arg Gly Thr Leu Val Thr Val Ser Ser
115 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcacct tcgataacta tggc 24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Asp Asn Tyr Gly
1 5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
atttcatatg atggaagtaa taca 24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Ser Tyr Asp Gly Ser Asn Thr
1 5

<210> SEQ ID NO 279
<211> LENGTH: 48
<212> TYPE: DNA
<213> ORGANISM: Artificial Sequence
<220> FEATURE:
<223> OTHER INFORMATION: Synthetic

<400> SEQUENCE: 279
gcgaaagatc ttgaattcga tattttgatt ggttatccct ttgactcc 48

<210> SEQ ID NO 280
<211> LENGTH: 16
<212> TYPE: PRT
<213> ORGANISM: Artificial Sequence
<220> FEATURE:
<223> OTHER INFORMATION: Synthetic

<400> SEQUENCE: 280

Ala Lys Asp Leu Glu Phe Asp Ile Leu Ile Gly Tyr Pro Phe Asp Ser
1 5 10 15

<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281
gacatccagt tgacccagtc tccatccttc ctgtctgcat ctgtaggaga cagagtcacc 60
atcacttgct gggccagtca ggacattagt cgttatttag cctggtatca gcaaaaacca 120
gggaaagccc ctaacctcct gatctatgct gcatccactt tgcaaagtgg ggtcccatca 180
aggttcagcg gcagtggatc tgggacagaa ttcactctca caatcaacag cctgcagcct 240
gaagattttg caacttatta ctgtcaacag ctttttagtt accctcggac gttcggccaa 300
gggaccaagg tggaaatcaa a 321

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Asp Ile Gln Leu Thr Gln Ser Pro Ser Phe Leu Ser Ala Ser Val Gly
1 5 10 15

Asp Arg Val Thr Ile Thr Cys Trp Ala Ser Gln Asp Ile Ser Arg Tyr
20 25 30

Leu Ala Trp Tyr Gln Gln Lys Pro Gly Lys Ala Pro Asn Leu Leu Ile
35 40 45

Tyr Ala Ala Ser Thr Leu Gln Ser Gly Val Pro Ser Arg Phe Ser Gly
50 55 60

Ser Gly Ser Gly Thr Glu Phe Thr Leu Thr Ile Asn Ser Leu Gln Pro
65 70 75 80

Glu Asp Phe Ala Thr Tyr Tyr Cys Gln Gln Leu Phe Ser Tyr Pro Arg
85 90 95

Thr Phe Gly Gln Gly Thr Lys Val Glu Ile Lys
100 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
caggacatta gtcgttat 18

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Asp Ile Ser Arg Tyr
1 5

<210> SEQ ID NO 285
<211> LENGTH: 9
<212> TYPE: DNA
<213> ORGANISM: Artificial Sequence
<220> FEATURE:

<223> OTHER INFORMATION: Synthetic

<400> SEQUENCE: 285 gctgcatcc 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Ala Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacagcttt ttagttaccc tcggacg 27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Leu Phe Ser Tyr Pro Arg Thr
1 5

<210> SEQ ID NO 289
<211> LENGTH: 366
<212> TYPE: DNA
<213> ORGANISM: Artificial Sequence
<220> FEATURE:
<223> OTHER INFORMATION: Synthetic

<400> SEQUENCE: 289
caggtgcagc tggtggagtc tgggggaggc gtggtccagc ctgggaggtc cctgagactc 60
tcctgtgcag cgtctggatt cagtttcagt agttatggca tgcactgggt ccgccaggct 120
ccaggcaagg ggctggagtg ggtggcagtg atgtggtatg atggaagtaa tgaatattat 180
gcagactccg tgaagggtcg attcatcatc tccagagaca attccaagag tacgctgtat 240
ctggaaatga acagcctgag agccgaggac acggctctgt attactgtgc gagagaggac 300
tgggacgagg gctactatta cggtatggac gtctggggcc aagggaccac ggtcaccgtc 360
tcctca 366

<210> SEQ ID NO 290
<211> LENGTH: 122
<212> TYPE: PRT
<213> ORGANISM: Artificial Sequence
<220> FEATURE:
<223> OTHER INFORMATION: Synthetic

<400> SEQUENCE: 290

Gln Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Ser Tyr
20 25 30

Gly Met His Trp Val Arg Gln Ala Pro Gly Lys Gly Leu Glu Trp Val
35 40 45

Ala Val Met Trp Tyr Asp Gly Ser Asn Glu Tyr Tyr Ala Asp Ser Val
50 55 60

Lys Gly Arg Phe Ile Ile Ser Arg Asp Asn Ser Lys Ser Thr Leu Tyr
65 70 75 80

Leu Glu Met Asn Ser Leu Arg Ala Glu Asp Thr Ala Leu Tyr Tyr Cys
85 90 95

Ala Arg Glu Asp Trp Asp Glu Gly Tyr Tyr Tyr Gly Met Asp Val Trp
100 105 110

Gly Gln Gly Thr Thr Val Thr Val Ser Ser
115 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcagtt tcagtagtta tggc 24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Ser Phe Ser Ser Tyr Gly
1 5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atgtggtatg atggaagtaa tgaa 24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Met Trp Tyr Asp Gly Ser Asn Glu
1 5

<210> SEQ ID NO 295

<211> LENGTH: 45
<212> TYPE: DNA
<213> ORGANISM: Artificial Sequence
<220> FEATURE:
<223> OTHER INFORMATION: Synthetic

<400> SEQUENCE: 295
gcgagagagg actgggacga gggctactat tacggtatgg acgtc 45

<210> SEQ ID NO 296
<211> LENGTH: 15
<212> TYPE: PRT
<213> ORGANISM: Artificial Sequence
<220> FEATURE:
<223> OTHER INFORMATION: Synthetic

<400> SEQUENCE: 296

Ala Arg Glu Asp Trp Asp Glu Gly Tyr Tyr Tyr Gly Met Asp Val
1 5 10 15

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcctcc ctgtttgcat ctgtaggaga cagagtcacc 60
atcacttgcc gggcaagtca ggacattaga tatgatttag gctggtatca gcagaaacca 120
gggaaagccc ctaagcgcct gatatatgct tcatccattt tggaaagtgg ggtcccatca 180
aggttcagcg gcagtggatc tgggacagaa tacactctca caatcagcac cctgcagtct 240
gaagattttg caatttatta ctgtctacag cataatagtt tcccgtggac gttcggccaa 300
gggaccaagg tggaaatcaa a 321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Leu Phe Ala Ser Val Gly
1 5 10 15

Asp Arg Val Thr Ile Thr Cys Arg Ala Ser Gln Asp Ile Arg Tyr Asp
20 25 30

Leu Gly Trp Tyr Gln Gln Lys Pro Gly Lys Ala Pro Lys Arg Leu Ile
35 40 45

Tyr Ala Ser Ser Ile Leu Glu Ser Gly Val Pro Ser Arg Phe Ser Gly
50 55 60

Ser Gly Ser Gly Thr Glu Tyr Thr Leu Thr Ile Ser Thr Leu Gln Ser
65 70 75 80

Glu Asp Phe Ala Ile Tyr Tyr Cys Leu Gln His Asn Ser Phe Pro Trp
85 90 95

Thr Phe Gly Gln Gly Thr Lys Val Glu Ile Lys
100 105

<210> SEQ ID NO 299
<211> LENGTH: 18

<212> TYPE: DNA
<213> ORGANISM: Artificial Sequence
<220> FEATURE:
<223> OTHER INFORMATION: Synthetic

<400> SEQUENCE: 299
caggacatta gatatgat 18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Asp Ile Arg Tyr Asp
1 5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gcttcatcc 9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ser Ser
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
ctacagcata atagtttccc gtggacg 27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Leu Gln His Asn Ser Phe Pro Trp Thr
1 5

<210> SEQ ID NO 305
<211> LENGTH: 664
<212> TYPE: PRT
<213> ORGANISM: Artificial Sequence
<220> FEATURE:
<223> OTHER INFORMATION: mROR1(M1-A29)-hRET(L29-R635)-mycmychis6

<400> SEQUENCE: 305

Met His Arg Pro Arg Arg Arg Gly Thr Arg Pro Pro Pro Leu Ala Leu
1               5                   10                  15

Leu Ala Ala Leu Leu Leu Ala Ala Arg Gly Ala Asp Ala Leu Tyr Phe
            20                  25                  30

Ser Arg Asp Ala Tyr Trp Glu Lys Leu Tyr Val Asp Gln Ala Ala Gly
        35                  40                  45

Thr Pro Leu Leu Tyr Val His Ala Leu Arg Asp Ala Pro Glu Glu Val
    50                  55                  60

Pro Ser Phe Arg Leu Gly Gln His Leu Tyr Gly Thr Tyr Arg Thr Arg
65                  70                  75                  80

Leu His Glu Asn Asn Trp Ile Cys Ile Gln Glu Asp Thr Gly Leu Leu
                85                  90                  95

Tyr Leu Asn Arg Ser Leu Asp His Ser Ser Trp Glu Lys Leu Ser Val
            100                 105                 110

Arg Asn Arg Gly Phe Pro Leu Leu Thr Val Tyr Leu Lys Val Phe Leu
        115                 120                 125

Ser Pro Thr Ser Leu Arg Glu Gly Glu Cys Gln Trp Pro Gly Cys Ala
    130                 135                 140

Arg Val Tyr Phe Ser Phe Phe Asn Thr Ser Phe Pro Ala Cys Ser Ser
145                 150                 155                 160

Leu Lys Pro Arg Glu Leu Cys Phe Pro Glu Thr Arg Pro Ser Phe Arg
                165                 170                 175

Ile Arg Glu Asn Arg Pro Pro Gly Thr Phe His Gln Phe Arg Leu Leu
            180                 185                 190

Pro Val Gln Phe Leu Cys Pro Asn Ile Ser Val Ala Tyr Arg Leu Leu
        195                 200                 205

Glu Gly Glu Gly Leu Pro Phe Arg Cys Ala Pro Asp Ser Leu Glu Val
    210                 215                 220

Ser Thr Arg Trp Ala Leu Asp Arg Glu Gln Arg Glu Lys Tyr Glu Leu
225                 230                 235                 240

Val Ala Val Cys Thr Val His Ala Gly Ala Arg Glu Glu Val Val Met
                245                 250                 255

Val Pro Phe Pro Val Thr Val Tyr Asp Glu Asp Asp Ser Ala Pro Thr
            260                 265                 270

Phe Pro Ala Gly Val Asp Thr Ala Ser Ala Val Val Glu Phe Lys Arg
        275                 280                 285

Lys Glu Asp Thr Val Val Ala Thr Leu Arg Val Phe Asp Ala Asp Val
    290                 295                 300

Val Pro Ala Ser Gly Glu Leu Val Arg Arg Tyr Thr Ser Thr Leu Leu
305                 310                 315                 320

Pro Gly Asp Thr Trp Ala Gln Gln Thr Phe Arg Val Glu His Trp Pro
                325                 330                 335

Asn Glu Thr Ser Val Gln Ala Asn Gly Ser Phe Val Arg Ala Thr Val
            340                 345                 350

His Asp Tyr Arg Leu Val Leu Asn Arg Asn Leu Ser Ile Ser Glu Asn
        355                 360                 365

Arg Thr Met Gln Leu Ala Val Leu Val Asn Asp Ser Asp Phe Gln Gly
    370                 375                 380

Pro Gly Ala Gly Val Leu Leu Leu His Phe Asn Val Ser Val Leu Pro
385                 390                 395                 400

Val Ser Leu His Leu Pro Ser Thr Tyr Ser Leu Ser Val Ser Arg Arg
405 410 415

Ala Arg Arg Phe Ala Gln Ile Gly Lys Val Cys Val Glu Asn Cys Gln
420 425 430

Ala Phe Ser Gly Ile Asn Val Gln Tyr Lys Leu His Ser Ser Gly Ala
435 440 445

Asn Cys Ser Thr Leu Gly Val Val Thr Ser Ala Glu Asp Thr Ser Gly
450 455 460

Ile Leu Phe Val Asn Asp Thr Lys Ala Leu Arg Arg Pro Lys Cys Ala
465 470 475 480

Glu Leu His Tyr Met Val Val Ala Thr Asp Gln Gln Thr Ser Arg Gln
485 490 495

Ala Gln Ala Gln Leu Leu Val Thr Val Glu Gly Ser Tyr Val Ala Glu
500 505 510

Glu Ala Gly Cys Pro Leu Ser Cys Ala Val Ser Lys Arg Arg Leu Glu
515 520 525

Cys Glu Glu Cys Gly Gly Leu Gly Ser Pro Thr Gly Arg Cys Glu Trp
530 535 540

Arg Gln Gly Asp Gly Lys Gly Ile Thr Arg Asn Phe Ser Thr Cys Ser
545 550 555 560

Pro Ser Thr Lys Thr Cys Pro Asp Gly His Cys Asp Val Val Glu Thr
565 570 575

Gln Asp Ile Asn Ile Cys Pro Gln Asp Cys Leu Arg Gly Ser Ile Val
580 585 590

Gly Gly His Glu Pro Gly Glu Pro Arg Gly Ile Lys Ala Gly Tyr Gly
595 600 605

Thr Cys Asn Cys Phe Pro Glu Glu Glu Lys Cys Phe Cys Glu Pro Glu
610 615 620

Asp Ile Gln Asp Pro Leu Cys Asp Glu Leu Cys Arg Glu Gln Lys Leu
625 630 635 640

Ile Ser Glu Glu Asp Leu Gly Gly Glu Gln Lys Leu Ile Ser Glu Glu
645 650 655

Asp Leu His His His His His His
660

<210> SEQ ID NO 306
<211> LENGTH: 664
<212> TYPE: PRT
<213> ORGANISM: Artificial Sequence
<220> FEATURE:
<223> OTHER INFORMATION: mROR1(M1-A29)-MfRET(L30-R636)-mycmychis6

<400> SEQUENCE: 306

Met His Arg Pro Arg Arg Arg Gly Thr Arg Pro Pro Pro Leu Ala Leu
1 5 10 15

Leu Ala Ala Leu Leu Leu Ala Ala Arg Gly Ala Asp Ala Leu Tyr Phe
20 25 30

Ser Arg Asp Ala Tyr Trp Glu Lys Leu Tyr Val Asp Gln Pro Ala Gly
35 40 45

Thr Pro Leu Leu Tyr Val His Ala Leu Arg Asp Ala Pro Glu Glu Val
50 55 60

Pro Ser Phe Arg Leu Gly Gln His Leu Tyr Gly Thr Tyr Arg Thr Arg
65 70 75 80

Leu His Glu Asn Asn Trp Ile Cys Ile Gln Glu Asp Thr Gly Leu Leu
85 90 95

```
Tyr Leu Asn Arg Ser Leu Asp Arg Ser Ser Trp Glu Lys Leu Ser Gly
            100                 105                 110

Arg Asn Arg Gly Phe Pro Leu Leu Thr Val Tyr Leu Lys Val Phe Leu
        115                 120                 125

Ser Pro Thr Ser Leu Arg Glu Gly Glu Cys Gln Trp Pro Gly Cys Ala
    130                 135                 140

Arg Val Tyr Phe Ser Phe Phe Asn Thr Ser Phe Pro Ala Cys Thr Ser
145                 150                 155                 160

Leu Lys Pro Arg Glu Leu Cys Phe Pro Glu Thr Arg Pro Ser Phe Arg
                165                 170                 175

Ile Arg Glu Asn Arg Pro Pro Gly Thr Phe His Gln Phe Arg Leu Leu
            180                 185                 190

Pro Val Gln Phe Leu Cys Pro Asn Ile Ser Val Ala Tyr Arg Leu Leu
        195                 200                 205

Glu Gly Glu Gly Leu Pro Phe Arg Cys Ala Pro Asp Ser Leu Glu Val
    210                 215                 220

Ser Thr Arg Trp Ala Leu Asp Arg Glu Gln Arg Glu Lys Tyr Glu Leu
225                 230                 235                 240

Val Ala Val Cys Thr Val His Ala Gly Ala Arg Glu Glu Val Val Met
                245                 250                 255

Val Pro Phe Pro Val Thr Val Tyr Asp Glu Asp Asp Ser Ala Pro Thr
            260                 265                 270

Phe Pro Ala Gly Val Asp Thr Ala Ser Ala Val Val Glu Phe Lys Arg
        275                 280                 285

Lys Glu Asp Thr Val Val Ala Thr Leu Arg Val Phe Asp Ala Asp Val
    290                 295                 300

Val Pro Ala Ser Gly Glu Leu Val Arg Arg Tyr Thr Ser Thr Leu Leu
305                 310                 315                 320

Pro Gly Asp Thr Trp Thr Gln Gln Thr Phe Arg Val Glu His Trp Pro
                325                 330                 335

Asn Glu Thr Ser Val Gln Ala Asn Gly Ser Phe Val Arg Ala Thr Val
            340                 345                 350

His Asp Tyr Arg Leu Val Leu Asn Arg Asn Leu Ser Ile Ser Glu Asn
        355                 360                 365

Arg Thr Met Gln Leu Ala Val Leu Val Asn Asp Ser Asp Phe Gln Gly
    370                 375                 380

Pro Gly Ala Gly Val Leu Leu Leu His Phe Asn Val Ser Val Leu Pro
385                 390                 395                 400

Val Ser Leu His Leu Pro Ser Ser Tyr Ser Leu Ser Val Ser Arg Arg
                405                 410                 415

Ala Arg Arg Phe Ala Gln Ile Gly Lys Val Cys Val Glu Asn Cys Gln
            420                 425                 430

Ala Phe Ser Gly Ile Asn Val Gln Tyr Glu Leu His Ser Ser Gly Ala
        435                 440                 445

Asn Cys Ser Thr Leu Gly Val Val Thr Ser Ala Glu Asp Thr Ser Gly
    450                 455                 460

Ile Leu Phe Val Asn Asp Thr Lys Ala Leu Arg Arg Pro Lys Cys Ala
465                 470                 475                 480

Glu Leu His Tyr Met Val Val Ala Thr Asn His Gln Thr Ser Arg Gln
                485                 490                 495

Ala Gln Ala Gln Leu Leu Val Thr Val Glu Gly Leu Tyr Val Ala Glu
            500                 505                 510
```

```
Glu Ala Gly Cys Pro Leu Ser Cys Ala Val Ser Lys Arg Arg Pro Glu
        515                 520                 525

Cys Glu Glu Cys Gly Gly Leu Gly Ser Pro Thr Gly Arg Cys Glu Trp
    530                 535                 540

Arg Gln Gly Asp Gly Lys Gly Ile Thr Arg Asn Phe Ser Thr Cys Ser
545                 550                 555                 560

Pro Ser Thr Lys Thr Cys Pro Asp Gly His Cys Asp Val Val Glu Thr
                565                 570                 575

Gln Asp Ile Asn Ile Cys Pro Gln Asp Cys Leu Arg Gly Ser Ile Val
            580                 585                 590

Gly Gly His Glu Pro Gly Glu Pro Arg Gly Ile Lys Ala Gly Tyr Gly
        595                 600                 605

Thr Cys Asn Cys Phe Pro Glu Glu Glu Lys Cys Phe Cys Glu Pro Glu
    610                 615                 620

Asp Ile Gln Asp Pro Leu Cys Asp Glu Leu Cys Arg Glu Gln Lys Leu
625                 630                 635                 640

Ile Ser Glu Glu Asp Leu Gly Gly Glu Gln Lys Leu Ile Ser Glu Glu
                645                 650                 655

Asp Leu His His His His His His
            660


<210> SEQ ID NO 307
<211> LENGTH: 869
<212> TYPE: PRT
<213> ORGANISM: Artificial Sequence
<220> FEATURE:
<223> OTHER INFORMATION: mROR1(M1-A29)-hRET(L29-R635)-mIgG2aFc

<400> SEQUENCE: 307

Met His Arg Pro Arg Arg Arg Gly Thr Arg Pro Pro Pro Leu Ala Leu
1               5                   10                  15

Leu Ala Ala Leu Leu Leu Ala Ala Arg Gly Ala Asp Ala Leu Tyr Phe
            20                  25                  30

Ser Arg Asp Ala Tyr Trp Glu Lys Leu Tyr Val Asp Gln Ala Ala Gly
        35                  40                  45

Thr Pro Leu Leu Tyr Val His Ala Leu Arg Asp Ala Pro Glu Glu Val
    50                  55                  60

Pro Ser Phe Arg Leu Gly Gln His Leu Tyr Gly Thr Tyr Arg Thr Arg
65                  70                  75                  80

Leu His Glu Asn Asn Trp Ile Cys Ile Gln Glu Asp Thr Gly Leu Leu
                85                  90                  95

Tyr Leu Asn Arg Ser Leu Asp His Ser Ser Trp Glu Lys Leu Ser Val
            100                 105                 110

Arg Asn Arg Gly Phe Pro Leu Leu Thr Val Tyr Leu Lys Val Phe Leu
        115                 120                 125

Ser Pro Thr Ser Leu Arg Glu Gly Glu Cys Gln Trp Pro Gly Cys Ala
    130                 135                 140

Arg Val Tyr Phe Ser Phe Phe Asn Thr Ser Phe Pro Ala Cys Ser Ser
145                 150                 155                 160

Leu Lys Pro Arg Glu Leu Cys Phe Pro Glu Thr Arg Pro Ser Phe Arg
                165                 170                 175

Ile Arg Glu Asn Arg Pro Pro Gly Thr Phe His Gln Phe Arg Leu Leu
            180                 185                 190

Pro Val Gln Phe Leu Cys Pro Asn Ile Ser Val Ala Tyr Arg Leu Leu
        195                 200                 205
```

```
Glu Gly Glu Gly Leu Pro Phe Arg Cys Ala Pro Asp Ser Leu Glu Val
    210                 215                 220

Ser Thr Arg Trp Ala Leu Asp Arg Glu Gln Arg Glu Lys Tyr Glu Leu
225                 230                 235                 240

Val Ala Val Cys Thr Val His Ala Gly Ala Arg Glu Glu Val Val Met
                245                 250                 255

Val Pro Phe Pro Val Thr Val Tyr Asp Glu Asp Asp Ser Ala Pro Thr
            260                 265                 270

Phe Pro Ala Gly Val Asp Thr Ala Ser Ala Val Val Glu Phe Lys Arg
        275                 280                 285

Lys Glu Asp Thr Val Val Ala Thr Leu Arg Val Phe Asp Ala Asp Val
    290                 295                 300

Val Pro Ala Ser Gly Glu Leu Val Arg Arg Tyr Thr Ser Thr Leu Leu
305                 310                 315                 320

Pro Gly Asp Thr Trp Ala Gln Gln Thr Phe Arg Val Glu His Trp Pro
                325                 330                 335

Asn Glu Thr Ser Val Gln Ala Asn Gly Ser Phe Val Arg Ala Thr Val
            340                 345                 350

His Asp Tyr Arg Leu Val Leu Asn Arg Asn Leu Ser Ile Ser Glu Asn
        355                 360                 365

Arg Thr Met Gln Leu Ala Val Leu Val Asn Asp Ser Asp Phe Gln Gly
    370                 375                 380

Pro Gly Ala Gly Val Leu Leu Leu His Phe Asn Val Ser Val Leu Pro
385                 390                 395                 400

Val Ser Leu His Leu Pro Ser Thr Tyr Ser Leu Ser Val Ser Arg Arg
                405                 410                 415

Ala Arg Arg Phe Ala Gln Ile Gly Lys Val Cys Val Glu Asn Cys Gln
            420                 425                 430

Ala Phe Ser Gly Ile Asn Val Gln Tyr Lys Leu His Ser Ser Gly Ala
        435                 440                 445

Asn Cys Ser Thr Leu Gly Val Val Thr Ser Ala Glu Asp Thr Ser Gly
    450                 455                 460

Ile Leu Phe Val Asn Asp Thr Lys Ala Leu Arg Arg Pro Lys Cys Ala
465                 470                 475                 480

Glu Leu His Tyr Met Val Val Ala Thr Asp Gln Gln Thr Ser Arg Gln
                485                 490                 495

Ala Gln Ala Gln Leu Leu Val Thr Val Glu Gly Ser Tyr Val Ala Glu
            500                 505                 510

Glu Ala Gly Cys Pro Leu Ser Cys Ala Val Ser Lys Arg Arg Leu Glu
        515                 520                 525

Cys Glu Glu Cys Gly Gly Leu Gly Ser Pro Thr Gly Arg Cys Glu Trp
    530                 535                 540

Arg Gln Gly Asp Gly Lys Gly Ile Thr Arg Asn Phe Ser Thr Cys Ser
545                 550                 555                 560

Pro Ser Thr Lys Thr Cys Pro Asp Gly His Cys Asp Val Val Glu Thr
                565                 570                 575

Gln Asp Ile Asn Ile Cys Pro Gln Asp Cys Leu Arg Gly Ser Ile Val
            580                 585                 590

Gly Gly His Glu Pro Gly Glu Pro Arg Gly Ile Lys Ala Gly Tyr Gly
        595                 600                 605

Thr Cys Asn Cys Phe Pro Glu Glu Glu Lys Cys Phe Cys Glu Pro Glu
    610                 615                 620
```

Asp Ile Gln Asp Pro Leu Cys Asp Glu Leu Cys Arg Glu Pro Arg Gly
625 630 635 640

Pro Thr Ile Lys Pro Cys Pro Pro Cys Lys Cys Pro Ala Pro Asn Leu
645 650 655

Leu Gly Gly Pro Ser Val Phe Ile Phe Pro Pro Lys Ile Lys Asp Val
660 665 670

Leu Met Ile Ser Leu Ser Pro Ile Val Thr Cys Val Val Val Asp Val
675 680 685

Ser Glu Asp Asp Pro Asp Val Gln Ile Ser Trp Phe Val Asn Asn Val
690 695 700

Glu Val His Thr Ala Gln Thr Gln Thr His Arg Glu Asp Tyr Asn Ser
705 710 715 720

Thr Leu Arg Val Val Ser Ala Leu Pro Ile Gln His Gln Asp Trp Met
725 730 735

Ser Gly Lys Glu Phe Lys Cys Lys Val Asn Asn Lys Asp Leu Pro Ala
740 745 750

Pro Ile Glu Arg Thr Ile Ser Lys Pro Lys Gly Ser Val Arg Ala Pro
755 760 765

Gln Val Tyr Val Leu Pro Pro Pro Glu Glu Glu Met Thr Lys Lys Gln
770 775 780

Val Thr Leu Thr Cys Met Val Thr Asp Phe Met Pro Glu Asp Ile Tyr
785 790 795 800

Val Glu Trp Thr Asn Asn Gly Lys Thr Glu Leu Asn Tyr Lys Asn Thr
805 810 815

Glu Pro Val Leu Asp Ser Asp Gly Ser Tyr Phe Met Tyr Ser Lys Leu
820 825 830

Arg Val Glu Lys Lys Asn Trp Val Glu Arg Asn Ser Tyr Ser Cys Ser
835 840 845

Val Val His Glu Gly Leu His Asn His His Thr Thr Lys Ser Phe Ser
850 855 860

Arg Thr Pro Gly Lys
865

<210> SEQ ID NO 308
<211> LENGTH: 667
<212> TYPE: PRT
<213> ORGANISM: Artificial Sequence
<220> FEATURE:
<223> OTHER INFORMATION: mROR1(M1-A29)-hGFRalpha1(D25-S429)-mIgG2aFc

<400> SEQUENCE: 308

Met His Arg Pro Arg Arg Arg Gly Thr Arg Pro Pro Pro Leu Ala Leu
1 5 10 15

Leu Ala Ala Leu Leu Leu Ala Ala Arg Gly Ala Asp Ala Asp Arg Leu
20 25 30

Asp Cys Val Lys Ala Ser Asp Gln Cys Leu Lys Glu Gln Ser Cys Ser
35 40 45

Thr Lys Tyr Arg Thr Leu Arg Gln Cys Val Ala Gly Lys Glu Thr Asn
50 55 60

Phe Ser Leu Ala Ser Gly Leu Glu Ala Lys Asp Glu Cys Arg Ser Ala
65 70 75 80

Met Glu Ala Leu Lys Gln Lys Ser Leu Tyr Asn Cys Arg Cys Lys Arg
85 90 95

Gly Met Lys Lys Glu Lys Asn Cys Leu Arg Ile Tyr Trp Ser Met Tyr
100 105 110

```
Gln Ser Leu Gln Gly Asn Asp Leu Leu Glu Asp Ser Pro Tyr Glu Pro
        115                 120                 125

Val Asn Ser Arg Leu Ser Asp Ile Phe Arg Val Val Pro Phe Ile Ser
    130                 135                 140

Asp Val Phe Gln Gln Val Glu His Ile Pro Lys Gly Asn Asn Cys Leu
145                 150                 155                 160

Asp Ala Ala Lys Ala Cys Asn Leu Asp Asp Ile Cys Lys Lys Tyr Arg
                165                 170                 175

Ser Ala Tyr Ile Thr Pro Cys Thr Thr Ser Val Ser Asn Asp Val Cys
            180                 185                 190

Asn Arg Arg Lys Cys His Lys Ala Leu Arg Gln Phe Phe Asp Lys Val
        195                 200                 205

Pro Ala Lys His Ser Tyr Gly Met Leu Phe Cys Ser Cys Arg Asp Ile
    210                 215                 220

Ala Cys Thr Glu Arg Arg Arg Gln Thr Ile Val Pro Val Cys Ser Tyr
225                 230                 235                 240

Glu Glu Arg Glu Lys Pro Asn Cys Leu Asn Leu Gln Asp Ser Cys Lys
                245                 250                 255

Thr Asn Tyr Ile Cys Arg Ser Arg Leu Ala Asp Phe Phe Thr Asn Cys
            260                 265                 270

Gln Pro Glu Ser Arg Ser Val Ser Ser Cys Leu Lys Glu Asn Tyr Ala
        275                 280                 285

Asp Cys Leu Leu Ala Tyr Ser Gly Leu Ile Gly Thr Val Met Thr Pro
    290                 295                 300

Asn Tyr Ile Asp Ser Ser Ser Leu Ser Val Ala Pro Trp Cys Asp Cys
305                 310                 315                 320

Ser Asn Ser Gly Asn Asp Leu Glu Glu Cys Leu Lys Phe Leu Asn Phe
                325                 330                 335

Phe Lys Asp Asn Thr Cys Leu Lys Asn Ala Ile Gln Ala Phe Gly Asn
            340                 345                 350

Gly Ser Asp Val Thr Val Trp Gln Pro Ala Phe Pro Val Gln Thr Thr
        355                 360                 365

Thr Ala Thr Thr Thr Thr Ala Leu Arg Val Lys Asn Lys Pro Leu Gly
    370                 375                 380

Pro Ala Gly Ser Glu Asn Glu Ile Pro Thr His Val Leu Pro Pro Cys
385                 390                 395                 400

Ala Asn Leu Gln Ala Gln Lys Leu Lys Ser Asn Val Ser Gly Asn Thr
                405                 410                 415

His Leu Cys Ile Ser Asn Gly Asn Tyr Glu Lys Glu Gly Leu Gly Ala
            420                 425                 430

Ser Ser Glu Pro Arg Gly Pro Thr Ile Lys Pro Cys Pro Pro Cys Lys
        435                 440                 445

Cys Pro Ala Pro Asn Leu Leu Gly Gly Pro Ser Val Phe Ile Phe Pro
    450                 455                 460

Pro Lys Ile Lys Asp Val Leu Met Ile Ser Leu Ser Pro Ile Val Thr
465                 470                 475                 480

Cys Val Val Val Asp Val Ser Glu Asp Asp Pro Asp Val Gln Ile Ser
                485                 490                 495

Trp Phe Val Asn Asn Val Glu Val His Thr Ala Gln Thr Gln Thr His
            500                 505                 510

Arg Glu Asp Tyr Asn Ser Thr Leu Arg Val Val Ser Ala Leu Pro Ile
        515                 520                 525
```

```
Gln His Gln Asp Trp Met Ser Gly Lys Glu Phe Lys Cys Lys Val Asn
    530                 535                 540

Asn Lys Asp Leu Pro Ala Pro Ile Glu Arg Thr Ile Ser Lys Pro Lys
545                 550                 555                 560

Gly Ser Val Arg Ala Pro Gln Val Tyr Val Leu Pro Pro Pro Glu Glu
                565                 570                 575

Glu Met Thr Lys Lys Gln Val Thr Leu Thr Cys Met Val Thr Asp Phe
            580                 585                 590

Met Pro Glu Asp Ile Tyr Val Glu Trp Thr Asn Asn Gly Lys Thr Glu
        595                 600                 605

Leu Asn Tyr Lys Asn Thr Glu Pro Val Leu Asp Ser Asp Gly Ser Tyr
    610                 615                 620

Phe Met Tyr Ser Lys Leu Arg Val Glu Lys Lys Asn Trp Val Glu Arg
625                 630                 635                 640

Asn Ser Tyr Ser Cys Ser Val Val His Glu Gly Leu His Asn His His
                645                 650                 655

Thr Thr Lys Ser Phe Ser Arg Thr Pro Gly Lys
            660                 665
```

<210> SEQ ID NO 309
<211> LENGTH: 5629
<212> TYPE: DNA
<213> ORGANISM: Artificial Sequence
<220> FEATURE:
<223> OTHER INFORMATION: Based on Homo sapiens sequence - hRET cDNA, isoform a (RET51), NM_020975.4

<400> SEQUENCE: 309

```
agtcccgcga ccgaagcagg gcgcgcagca gcgctgagtg ccccggaacg tgcgtcgcgc     60

ccccagtgtc cgtcgcgtcc gccgcgcccc gggcggggat ggggcggcca gactgagcgc    120

cgcacccgcc atccagaccc gccggcccta gccgcagtcc ctccagccgt ggccccagcg    180

cgcacgggcg atggcgaagg cgacgtccgg tgccgcgggg ctgcgtctgc tgttgctgct    240

gctgctgccg ctgctaggca aagtggcatt gggcctctac ttctcgaggg atgcttactg    300

ggagaagctg tatgtggacc aggcggccgg cacgcccttg ctgtacgtcc atgccctgcg    360

ggacgcccct gaggaggtgc ccagcttccg cctgggccag catctctacg gcacgtaccg    420

cacacggctg catgagaaca actggatctg catccaggag gacaccggcc tcctctacct    480

taaccggagc ctggaccata gctcctggga gaagctcagt gtccgcaacc gcggctttcc    540

cctgctcacc gtctacctca aggtcttcct gtcacccaca tcccttcgtg agggcgagtg    600

ccagtggcca ggctgtgccc gcgtatactt ctccttcttc aacacctcct ttccagcctg    660

cagctccctc aagccccggg agctctgctt cccagagaca aggccctcct tccgcattcg    720

ggagaaccga cccccaggca ccttccacca gttccgcctg ctgcctgtgc agttcttgtg    780

ccccaacatc agcgtggcct acaggctcct ggagggtgag ggtctgccct tccgctgcgc    840

cccggacagc ctggaggtga gcacgcgctg ggccctggac cgcgagcagc gggagaagta    900

cgagctggtg gccgtgtgca ccgtgcacgc cggcgcgcgc gaggaggtgg tgatggtgcc    960

cttcccggtg accgtgtacg acgaggacga ctcggcgccc accttccccg cgggcgtcga   1020

caccgccagc gccgtggtgg agttcaagcg gaaggaggac accgtggtgg ccacgctgcg   1080

tgtcttcgat gcagacgtgg tacctgcatc aggggagctg gtgaggcggt acacaagcac   1140

gctgctcccc ggggacacct gggcccagca gaccttccgg gtggaacact ggcccaacga   1200

gacctcggtc caggccaacg gcagcttcgt gcgggcgacc gtacatgact ataggctggt   1260
```

```
tctcaaccgg aacctctcca tctcggagaa ccgcaccatg cagctggcgg tgctggtcaa   1320
tgactcagac ttccagggcc caggagcggg cgtcctcttg ctccacttca acgtgtcggt   1380
gctgccggtc agcctgcacc tgcccagtac ctactccctc tccgtgagca ggagggctcg   1440
ccgatttgcc cagatcggga aagtctgtgt ggaaaactgc caggcattca gtggcatcaa   1500
cgtccagtac aagctgcatt cctctggtgc caactgcagc acgctagggg tggtcacctc   1560
agccgaggac acctcgggga tcctgtttgt gaatgacacc aaggccctgc ggcggcccaa   1620
gtgtgccgaa cttcactaca tggtggtggc caccgaccag cagacctcta ggcaggccca   1680
ggcccagctg cttgtaacag tggaggggtc atatgtggcc gaggaggcgg gctgcccccct   1740
gtcctgtgca gtcagcaaga gacggctgga gtgtgaggag tgtggcggcc tgggctcccc   1800
aacaggcagg tgtgagtgga ggcaaggaga tggcaaaggg atcaccagga acttctccac   1860
ctgctctccc agcaccaaga cctgccccga cggccactgc gatgttgtgg agacccaaga   1920
catcaacatt tgccctcagg actgcctccg ggcagcatt gttgggggac acgagcctgg   1980
ggagccccgg gggattaaag ctggctatgg cacctgcaac tgcttccctg aggaggagaa   2040
gtgcttctgc gagcccgaag acatccagga tccactgtgc gacgagctgt gccgcacggt   2100
gatcgcagcc gctgtcctct tctccttcat cgtctcggtg ctgctgtctg ccttctgcat   2160
ccactgctac cacaagtttg cccacaagcc acccatctcc tcagctgaga tgaccttccg   2220
gaggcccgcc caggccttcc cggtcagcta ctcctcttcc ggtgcccgcc ggccctcgct   2280
ggactccatg gagaaccagg tctccgtgga tgccttcaag atcctggagg atccaaagtg   2340
ggaattccct cggaagaact tggttcttgg aaaaactcta ggagaaggcg aatttggaaa   2400
agtggtcaag gcaacggcct tccatctgaa aggcagagca gggtacacca cggtggccgt   2460
gaagatgctg aaagagaacg cctccccgag tgagcttcga gacctgctgt cagagttcaa   2520
cgtcctgaag caggtcaacc acccacatgt catcaaattg tatggggcct gcagccagga   2580
tggcccgctc ctcctcatcg tggagtacgc caaatacggc tccctgcggg gcttcctccg   2640
cgagagccgc aaagtggggc ctggctacct gggcagtgga ggcagccgca actccagctc   2700
cctggaccac ccggatgagc gggccctcac catgggcgac ctcatctcat ttgcctggca   2760
gatctcacag gggatgcagt atctggccga gatgaagctc gttcatcggg acttggcagc   2820
cagaaacatc ctggtagctg aggggcggaa gatgaagatt tcggatttcg gcttgtcccg   2880
agatgtttat gaagaggatt cctacgtgaa gaggagccag ggtcggattc cagttaaatg   2940
gatggcaatt gaatcccttt ttgatcatat ctacaccacg caaagtgatg tatggtcttt   3000
tggtgtcctg ctgtgggaga tcgtgaccct agggggaaac ccctatcctg ggattcctcc   3060
tgagcggctc ttcaaccttc tgaagaccgg ccaccggatg gagaggccag acaactgcag   3120
cgaggagatg taccgcctga tgctgcaatg ctggaagcag gagccggaca aaaggccggt   3180
gtttgcggac atcagcaaag acctggagaa gatgatggtt aagaggagag actacttgga   3240
ccttgcggcg tccactccat ctgactccct gatttatgac gacggcctct cagaggagga   3300
gacaccgctg gtggactgta ataatgcccc cctccctcga gccctccctt ccacatggat   3360
tgaaaacaaa ctctatggca tgtcagaccc gaactggcct ggagagagtc ctgtaccact   3420
cacgagagct gatggcacta acactgggtt tccaagatat ccaaatgata gtgtatatgc   3480
taactggatg ctttcaccct cagcggcaaa attaatggac acgtttgata gttaacattt   3540
ctttgtgaaa ggtaatggac tcacaagggg aagaaacatg ctgagaatgg aaagtctacc   3600
```

```
ggccctttct ttgtgaacgt cacattggcc gagccgtgtt cagttcccag gtggcagact   3660
cgtttttggt agtttgtttt aacttccaag gtggttttac ttctgatagc cggtgatttt   3720
ccctcctagc agacatgcca caccgggtaa gagctctgag tcttagtggt taagcattcc   3780
tttctcttca gtgcccagca gcacccagtg ttggtctgtg tccatcagtg accaccaaca   3840
ttctgtgttc acatgtgtgg gtccaacact tactacctgg tgtatgaaat tggacctgaa   3900
ctgttggatt tttctagttg ccgccaaaca aggcaaaaaa atttaaacat gaagcacaca   3960
cacaaaaaag gcagtaggaa aaatgctggc cctgatgacc tgtccttatt cagaatgaga   4020
gactgcgggg ggggcctggg ggtagtgtca atgcccctcc agggctggag ggggaagaggg  4080
gccccgagga tgggcctggg ctcagcattc gagatcttga gaatgatttt tttttaatca   4140
tgcaaccttt ccttaggaag acatttggtt ttcatcatga ttaagatgat tcctagattt   4200
agcacaatgg agagattcca tgccatcttt actatgtgga tggtggtatc agggaagagg   4260
gctcacaaga cacatttgtc ccccgggccc accacatcat cctcacgtgt tcggtactga   4320
gcagccacta cccctgatga gaacagtatg aagaaagggg gctgttggag tcccagaatt   4380
gctgacagca gaggctttgc tgctgtgaat cccacctgcc accagcctgc agcacacccc   4440
acagccaagt agaggcgaaa gcagtggctc atcctacctg ttaggagcag gtagggcttg   4500
tactcacttt aatttgaatc ttatcaactt actcataaag ggacaggcta gctagctgtg   4560
ttagaagtag caatgacaat gaccaaggac tgctacacct ctgattacaa ttctgatgtg   4620
aaaaagatgg tgtttggctc ttatagagcc tgtgtgaaag gcccatggat cagctcttcc   4680
tgtgtttgta atttaatgct gctacaagat gtttctgttt cttagattct gaccatgact   4740
cataagcttc ttgtcattct tcattgcttg tttgtggtca cagatgcaca acactcctcc   4800
agtcttgtgg gggcagcttt tgggaagtct cagcagctct tctggctgtg ttgtcagcac   4860
tgtaacttcg cagaaaagag tcggattacc aaaacactgc ctgctcttca gacttaaagc   4920
actgatagga cttaaaatag tctcattcaa atactgtatt ttatataggc atttcacaaa   4980
aacagcaaaa ttgtggcatt ttgtgaggcc aaggcttgga tgcgtgtgta atagagcctt   5040
gtggtgtgtg cgcacacacc cagagggaga gtttgaaaaa tgcttattgg acacgtaacc   5100
tggctctaat ttgggctgtt tttcagatac actgtgataa gttcttttac aaatatctat   5160
agacatggta aacttttggt tttcagatat gcttaatgat agtcttacta aatgcagaaa   5220
taagaataaa ctttctcaaa ttattaaaaa tgcctacaca gtaagtgtga attgctgcaa   5280
caggtttgtt ctcaggaggg taagaactcc aggtctaaac agctgaccca gtgatgggga   5340
atttatcctt gaccaattta tccttgacca ataacctaat tgtctattcc tgagttataa   5400
aagtccccat ccttattagc tctactggaa ttttcataca cgtaaatgca gaagttacta   5460
agtattaagt attactgagt attaagtagt aatctgtcag ttattaaaat ttgtaaaatc   5520
tatttatgaa aggtcattaa accagatcat gttccttttt ttgtaatcaa ggtgactaag   5580
aaaatcagtt gtgtaaataa aatcatgtat cataaaaaaa aaaaaaaaa              5629
```

<210> SEQ ID NO 310
<211> LENGTH: 1114
<212> TYPE: PRT
<213> ORGANISM: Artificial Sequence
<220> FEATURE:
<223> OTHER INFORMATION: Based on Homo sapiens sequence - hRET isoform
a (RET51), NP_066124.1

<400> SEQUENCE: 310

Met Ala Lys Ala Thr Ser Gly Ala Ala Gly Leu Arg Leu Leu Leu Leu
1 5 10 15

Leu Leu Leu Pro Leu Leu Gly Lys Val Ala Leu Gly Leu Tyr Phe Ser
20 25 30

Arg Asp Ala Tyr Trp Glu Lys Leu Tyr Val Asp Gln Ala Ala Gly Thr
35 40 45

Pro Leu Leu Tyr Val His Ala Leu Arg Asp Ala Pro Glu Glu Val Pro
50 55 60

Ser Phe Arg Leu Gly Gln His Leu Tyr Gly Thr Tyr Arg Thr Arg Leu
65 70 75 80

His Glu Asn Asn Trp Ile Cys Ile Gln Glu Asp Thr Gly Leu Leu Tyr
85 90 95

Leu Asn Arg Ser Leu Asp His Ser Ser Trp Glu Lys Leu Ser Val Arg
100 105 110

Asn Arg Gly Phe Pro Leu Leu Thr Val Tyr Leu Lys Val Phe Leu Ser
115 120 125

Pro Thr Ser Leu Arg Glu Gly Glu Cys Gln Trp Pro Gly Cys Ala Arg
130 135 140

Val Tyr Phe Ser Phe Phe Asn Thr Ser Phe Pro Ala Cys Ser Ser Leu
145 150 155 160

Lys Pro Arg Glu Leu Cys Phe Pro Glu Thr Arg Pro Ser Phe Arg Ile
165 170 175

Arg Glu Asn Arg Pro Pro Gly Thr Phe His Gln Phe Arg Leu Leu Pro
180 185 190

Val Gln Phe Leu Cys Pro Asn Ile Ser Val Ala Tyr Arg Leu Leu Glu
195 200 205

Gly Glu Gly Leu Pro Phe Arg Cys Ala Pro Asp Ser Leu Glu Val Ser
210 215 220

Thr Arg Trp Ala Leu Asp Arg Glu Gln Arg Glu Lys Tyr Glu Leu Val
225 230 235 240

Ala Val Cys Thr Val His Ala Gly Ala Arg Glu Glu Val Val Met Val
245 250 255

Pro Phe Pro Val Thr Val Tyr Asp Glu Asp Asp Ser Ala Pro Thr Phe
260 265 270

Pro Ala Gly Val Asp Thr Ala Ser Ala Val Val Glu Phe Lys Arg Lys
275 280 285

Glu Asp Thr Val Val Ala Thr Leu Arg Val Phe Asp Ala Asp Val Val
290 295 300

Pro Ala Ser Gly Glu Leu Val Arg Arg Tyr Thr Ser Thr Leu Leu Pro
305 310 315 320

Gly Asp Thr Trp Ala Gln Gln Thr Phe Arg Val Glu His Trp Pro Asn
325 330 335

Glu Thr Ser Val Gln Ala Asn Gly Ser Phe Val Arg Ala Thr Val His
340 345 350

Asp Tyr Arg Leu Val Leu Asn Arg Asn Leu Ser Ile Ser Glu Asn Arg
355 360 365

Thr Met Gln Leu Ala Val Leu Val Asn Asp Ser Asp Phe Gln Gly Pro
370 375 380

Gly Ala Gly Val Leu Leu Leu His Phe Asn Val Ser Val Leu Pro Val
385 390 395 400

```
Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815
```

```
Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035

Pro Leu  Val Asp Cys Asn Asn  Ala Pro Leu Pro Arg  Ala Leu Pro
    1040                1045                1050

Ser Thr  Trp Ile Glu Asn Lys  Leu Tyr Gly Met Ser  Asp Pro Asn
    1055                1060                1065

Trp Pro  Gly Glu Ser Pro Val  Pro Leu Thr Arg Ala  Asp Gly Thr
    1070                1075                1080

Asn Thr  Gly Phe Pro Arg Tyr  Pro Asn Asp Ser Val  Tyr Ala Asn
    1085                1090                1095

Trp Met  Leu Ser Pro Ser Ala  Ala Lys Leu Met Asp  Thr Phe Asp
    1100                1105                1110

Ser
```

<210> SEQ ID NO 311
<211> LENGTH: 4174
<212> TYPE: DNA
<213> ORGANISM: Artificial Sequence
<220> FEATURE:
<223> OTHER INFORMATION: Based on Homo sapiens sequence - hRET cDNA, isoform c (RET9), NM_020630.4

<400> SEQUENCE: 311

```
agtcccgcga ccgaagcagg gcgcgcagca gcgctgagtg ccccggaacg tgcgtcgcgc      60

ccccagtgtc cgtcgcgtcc gccgcgcccc gggcggggat ggggcggcca gactgagcgc     120

cgcacccgcc atccagaccc gccggcccta gccgcagtcc ctccagccgt ggccccagcg     180

cgcacgggcg atggcgaagg cgacgtccgg tgccgcgggg ctgcgtctgc tgttgctgct     240

gctgctgccg ctgctaggca aagtggcatt gggcctctac ttctcgaggg atgcttactg     300
```

```
ggagaagctg tatgtggacc aggcggccgg cacgcccttg ctgtacgtcc atgccctgcg    360
ggacgcccct gaggaggtgc ccagcttccg cctgggccag catctctacg gcacgtaccg    420
cacacggctg catgagaaca actggatctg catccaggag gacaccggcc tcctctacct    480
taaccggagc ctggaccata gctcctggga gaagctcagt gtccgcaacc gcggctttcc    540
cctgctcacc gtctacctca aggtcttcct gtcacccaca tcccttcgtg agggcgagtg    600
ccagtggcca ggctgtgccc gcgtatactt ctccttcttc aacacctcct ttccagcctg    660
cagctccctc aagccccggg agctctgctt cccagagaca aggccctcct tccgcattcg    720
ggagaaccga cccccaggca ccttccacca gttccgcctg ctgcctgtgc agttcttgtg    780
ccccaacatc agcgtggcct acaggctcct ggagggtgag ggtctgccct tccgctgcgc    840
ccggacagc ctggaggtga gcacgcgctg ggccctggac cgcgagcagc gggagaagta    900
cgagctggtg gccgtgtgca ccgtgcacgc cggcgcgcgc gaggaggtgg tgatggtgcc    960
cttcccggtg accgtgtacg acgaggacga ctcggcgccc accttccccg cgggcgtcga   1020
caccgccagc gccgtggtgg agttcaagcg gaaggaggac accgtggtgg ccacgctgcg   1080
tgtcttcgat gcagacgtgg tacctgcatc aggggagctg gtgaggcggt acacaagcac   1140
gctgctcccc ggggacacct gggcccagca gaccttccgg gtggaacact ggcccaacga   1200
gacctcggtc caggccaacg gcagcttcgt gcgggcgacc gtacatgact ataggctggt   1260
tctcaaccgg aacctctcca tctcggagaa ccgcaccatg cagctggcgg tgctggtcaa   1320
tgactcagac ttccagggcc caggagcggg cgtcctcttg ctccacttca acgtgtcggt   1380
gctgccggtc agcctgcacc tgcccagtac ctactccctc tccgtgagca ggagggctcg   1440
ccgatttgcc cagatcggga aagtctgtgt ggaaaactgc caggcattca gtggcatcaa   1500
cgtccagtac aagctgcatt cctctggtgc caactgcagc acgctagggg tggtcacctc   1560
agccgaggac acctcgggga tcctgtttgt gaatgacacc aaggccctgc ggcggcccaa   1620
gtgtgccgaa cttcactaca tggtggtggc caccgaccag cagacctcta ggcaggccca   1680
ggcccagctg cttgtaacag tggaggggtc atatgtggcc gaggaggcgg gctgcccccct   1740
gtcctgtgca gtcagcaaga gacggctgga gtgtgaggag tgtggcggcc tgggctcccc   1800
aacaggcagg tgtgagtgga ggcaaggaga tggcaaaggg atcaccagga acttctccac   1860
ctgctctccc agcaccaaga cctgccccga cggccactgc gatgttgtgg agacccaaga   1920
catcaacatt tgccctcagg actgcctccg gggcagcatt gttgggggac acgagcctgg   1980
ggagccccgg gggattaaag ctggctatgg cacctgcaac tgcttccctg aggaggagaa   2040
gtgcttctgc gagcccgaag acatccagga tccactgtgc gacgagctgt gccgcacggt   2100
gatcgcagcc gctgtcctct tctccttcat cgtctcggtg ctgctgtctg ccttctgcat   2160
ccactgctac cacaagtttg cccacaagcc acccatctcc tcagctgaga tgaccttccg   2220
gaggcccgcc caggccttcc cggtcagcta ctcctcttcc ggtgcccgcc ggccctcgct   2280
ggactccatg gagaaccagg tctccgtgga tgccttcaag atcctggagg atccaaagtg   2340
ggaattccct cggaagaact tggttcttgg aaaaactcta ggagaaggcg aatttggaaa   2400
agtggtcaag gcaacggcct tccatctgaa aggcagagca gggtacacca cggtggccgt   2460
gaagatgctg aaagagaacg cctccccgag tgagcttcga gacctgctgt cagagttcaa   2520
cgtcctgaag caggtcaacc acccacatgt catcaaattg tatggggcct gcagccagga   2580
tggcccgctc ctcctcatcg tggagtacgc caaatacggc tccctgcggg gcttcctccg   2640
```

```
cgagagccgc aaagtggggc ctggctacct gggcagtgga ggcagccgca actccagctc   2700
cctggaccac ccggatgagc gggccctcac catgggcgac ctcatctcat ttgcctggca   2760
gatctcacag ggatgcagt atctggccga gatgaagctc gttcatcggg acttggcagc   2820
cagaaacatc ctggtagctg aggggcggaa gatgaagatt tcggatttcg gcttgtcccg   2880
agatgtttat gaagaggatt cctacgtgaa gaggagccag ggtcggattc cagttaaatg   2940
gatggcaatt gaatcccttt ttgatcatat ctacaccacg caaagtgatg tatggtcttt   3000
tggtgtcctg ctgtgggaga tcgtgaccct agggggaaac ccctatcctg ggattcctcc   3060
tgagcggctc ttcaaccttc tgaagaccgg ccaccggatg gagaggccag acaactgcag   3120
cgaggagatg taccgcctga tgctgcaatg ctggaagcag gagccggaca aaaggccggt   3180
gtttgcggac atcagcaaag acctggagaa gatgatggtt aagaggagag actacttgga   3240
ccttgcggcg tccactccat ctgactccct gatttatgac gacggcctct cagaggagga   3300
gacaccgctg gtggactgta ataatgcccc cctccctcga gccctccctt ccacatggat   3360
tgaaaacaaa ctctatggta gaatttccca tgcatttact agattctagc accgctgtcc   3420
cctctgcact atccttcctc tctgtgatgc tttttaaaaa tgtttctggt ctgaacaaaa   3480
ccaaagtctg ctctgaacct ttttatttgt aaatgtctga ctttgcatcc agtttacatt   3540
taggcattat tgcaactatg tttttctaaa aggaagtgaa aataagtgta attaccacat   3600
tgcccagcaa cttaggatgg tagaggaaaa aacagatcag ggcggaactc tcaggggaga   3660
ccaagaacag gttgaataag gcgcttctgg ggtgggaatc aagtcatagt acttctactt   3720
taactaagtg gataaatata caaatctggg gaggtattca gttgagaaag gagccaccag   3780
caccactcag cctgcactgg gagcacagcc aggttccccc agacccctcc tgggcaggca   3840
ggtgcctctc agaggccacc cggcactggc gagcagccac tggccaagcc tcagccccag   3900
tcccagccac atgtcctcca tcaggggtag cgaggttgca ggagctggct ggccctggga   3960
ggacgcaccc ccactgctgt tttcacatcc tttcccttac ccaccttcag gacggttgtc   4020
acttatgaag tcagtgctaa agctggagca gttgcttttt gaaagaacat ggtctgtggt   4080
gctgtggtct tacaatggac agtaaatatg gttcttgcca aaactccttc ttttgtcttt   4140
gattaaatac tagaaattta aaaaaaaaaa aaaa                               4174
```

<210> SEQ ID NO 312
<211> LENGTH: 1072
<212> TYPE: PRT
<213> ORGANISM: Artificial Sequence
<220> FEATURE:
<223> OTHER INFORMATION: Based on Homo sapiens sequence - hRET isoform c (RET9), NP_065681.1

<400> SEQUENCE: 312

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80
```

```
His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495
```

```
Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910
```

```
Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                1005

Met Val  Lys Arg Arg Asp Tyr  Leu Asp Leu Ala Ala  Ser Thr Pro
    1010                1015                1020

Ser Asp  Ser Leu Ile Tyr Asp  Asp Gly Leu Ser Glu  Glu Glu Thr
    1025                1030                1035

Pro Leu  Val Asp Cys Asn Asn  Ala Pro Leu Pro Arg  Ala Leu Pro
    1040                1045                1050

Ser Thr  Trp Ile Glu Asn Lys  Leu Tyr Gly Arg Ile  Ser His Ala
    1055                1060                1065

Phe Thr  Arg Phe
    1070
```

<210> SEQ ID NO 313
<211> LENGTH: 868
<212> TYPE: PRT
<213> ORGANISM: Artificial Sequence
<220> FEATURE:
<223> OTHER INFORMATION: NP_066124.1 hRET extracellular domain (amino acids 1-635)-mouse Fc

<400> SEQUENCE: 313

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175
```

```
Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590
```

-continued

```
Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
    610                 615                 620

Ile Gln Asp Pro Leu Cys Asp Glu Leu Cys Arg Glu Pro Arg Gly Pro
625                 630                 635                 640

Thr Ile Lys Pro Cys Pro Pro Cys Lys Cys Pro Ala Pro Asn Leu Leu
                645                 650                 655

Gly Gly Pro Ser Val Phe Ile Phe Pro Pro Lys Ile Lys Asp Val Leu
            660                 665                 670

Met Ile Ser Leu Ser Pro Ile Val Thr Cys Val Val Val Asp Val Ser
        675                 680                 685

Glu Asp Asp Pro Asp Val Gln Ile Ser Trp Phe Val Asn Asn Val Glu
    690                 695                 700

Val His Thr Ala Gln Thr Gln Thr His Arg Glu Asp Tyr Asn Ser Thr
705                 710                 715                 720

Leu Arg Val Val Ser Ala Leu Pro Ile Gln His Gln Asp Trp Met Ser
                725                 730                 735

Gly Lys Glu Phe Lys Cys Lys Val Asn Asn Lys Asp Leu Pro Ala Pro
            740                 745                 750

Ile Glu Arg Thr Ile Ser Lys Pro Lys Gly Ser Val Arg Ala Pro Gln
        755                 760                 765

Val Tyr Val Leu Pro Pro Pro Glu Glu Glu Met Thr Lys Lys Gln Val
    770                 775                 780

Thr Leu Thr Cys Met Val Thr Asp Phe Met Pro Glu Asp Ile Tyr Val
785                 790                 795                 800

Glu Trp Thr Asn Asn Gly Lys Thr Glu Leu Asn Tyr Lys Asn Thr Glu
                805                 810                 815

Pro Val Leu Asp Ser Asp Gly Ser Tyr Phe Met Tyr Ser Lys Leu Arg
            820                 825                 830

Val Glu Lys Lys Asn Trp Val Glu Arg Asn Ser Tyr Ser Cys Ser Val
        835                 840                 845

Val His Glu Gly Leu His Asn His His Thr Thr Lys Ser Phe Ser Arg
    850                 855                 860

Thr Pro Gly Lys
865
```

HUMAN ANTIBODIES THAT BIND RET AND METHODS OF USE THEREOF

This application is a U.S. National Phase Application filed under 35 U.S.C. § 371 of PCT Application No. PCT/US2020/027554 filed Apr. 9, 2020, which claims priority to U.S. Provisional Application Ser. No. 62/832,218, filed Apr. 10, 2019, each of the applications of which are incorporated by reference in their entireties.

FIELD OF THE INVENTION

The present invention is related to human antibodies and antigen-binding fragments of human antibodies that specifically bind to RET (rearranged during transfection) receptor tyrosine kinase and compositions comprising these antibodies and therapeutic methods of using these antibodies.

SEQUENCE LISTING

An official copy of the sequence listing is submitted concurrently with the specification electronically via EFS-Web as an ASCII formatted sequence listing with a file name of 10582WO01_SeqList_ST25.TXT, a creation date of Apr. 9, 2020, and a size of about 168 kilobytes. The sequence listing contained in this ASCII formatted document is part of the specification and is herein incorporated by reference in its entirety.

STATEMENT OF RELATED ART

The RET (REarranged during Transfection) receptor tyrosine kinase is expressed during development in a variety of tissues, including the peripheral and central nervous systems and the kidney (Arighi, E. et al, (2005), Cytokine Growth Factor Rev 16:441-467; Borrello, M G, et al, (2013), Expert Opin. Ther. Targets, 17(4):403-419; Golden, J P, et al. (1998), J. Comp. Neurol. 398:139-150; Golden, J P, et al. (1999), Exp. Neurol. 158:504-528). It is also expressed in neural crest-derived cells and regulates cell proliferation, migration and survival (Coulpier, M. et al, (2002), J Biol Chem, 277:1991-1999; Golden, J P, et al. (1998), J. Comp. Neurol. 398:139-150; Golden, J P, et al. (1999), Exp. Neurol. 158:504-528). RET knockout mice exhibit renal agenesis and lack enteric neurons in the digestive tract. A very similar phenotype is observed in both GFRα1 and GDNF knockout mice, confirming a major role for GDNF/GFRα1 in the activation of RET signaling during development.

RET is the signaling receptor for ligands of the glial-derived neurotrophic factor (GDNF) family, which comprises GDNF, artemin, neurturin and persephin. GDNF family ligands interact with and activate RET only in the presence of one of four GPI-linked co-receptors, known as GDNF family □receptors GFR1□(1-4) (Baloh, R H, et al. (2000), Curr Opin Neurobiol 10:103-110; Borrello, M G, et al (2013), Expert Opin. Ther. Targets, 17(4):403-419). The primary ligands for the co-receptors GFRα1, GFRα2, GFRα3 and GFRα4 are GDNF, neurturin (NRTN), artemin (ARTN) and persephin (PSPN), respectively, although cross-talk between ligands and co-receptors have been observed in vitro.

The role of RET as a driver of tumorigenesis has been established by the activating mutations that are frequently observed in multiple endocrine neoplasia syndromes MEN2A and MEN2B and in familial medullary thyroid cancer (Mulligan, L M, et al, (1994), Nat. Genet. 6:70-74). Furthermore, a large percentage of sporadic medullary thyroid cancers contain somatic activating mutations in RET (Fusco, A. et al, (1987), Nature 328:170-172; Grieco, M. et al, (1990), Cell 60:557-563). These mutations can occur in the kinase domain or in the extracellular domain, where they result in unpaired cysteines that are thought to promote ligand-independent RET dimerization and activation. Thus, the tumorigenic potential of RET in humans has been clearly established via genetic studies.

In addition to its role in endocrine cancers, recent work has identified RET as a potential therapeutic target in breast cancer. RET and GFRα1 are expressed in breast cancer cell lines and in primary human breast cancer samples. Interestingly, the expression of RET and GFRα1 can be induced by estrogen in vitro. Consistent with this observation, RET and GFRα1 are preferentially expressed in the estrogen receptor-positive subset of breast cancers. Furthermore, GDNF-induced RET signaling promotes anchorage-independent growth of estrogen receptor-positive breast cancer cells and potentiates the effects of estrogen on the growth and survival of these cells, indicating a functional cooperation between these two pathways. Thus, RET signaling appears to be an important driver of the oncogenic phenotype in breast cancer cells (Wang, C. et al (2012), Breast Cancer Res Treat 133(2):487-500; Stine, Z E, et al, (2011), Human Molecular Genetics 20(19):3746-3756).

Activation of RET is initiated by binding of GDNF to GFRα1. The GDNF/GFRα1 complex then binds to RET, resulting in receptor dimerization and activation. There are several small molecules that have the ability to inhibit RET, including an agent (vandetanib) that has exhibited activity in medullary thyroid cancer patients (See Wells, S A et al, (2012), J Clin Oncol 30:134-141; Leboulleux, S. et al, (2012), Lancet Oncol 13:897-905). Other small molecules have been identified that bind to and inhibit RET signaling (Borrello, M G, et al, (2013), Expert Opin. Ther. Targets, 17(4):403-419). Unfortunately, due to their lack of specificity, certain of these compounds have shown adverse events in clinical trials that have precluded further development.

To date, there have been no reports of therapeutic anti-RET monoclonal antibodies for use in a clinical setting to treat tumors expressing RET. The studies reported herein describe the generation of fully human monoclonal antibodies that bind to RET and prevent the interaction of RET with one or more GDNF family members complexed with their corresponding co-receptors.

The domain structure of the RET extracellular region is shown in FIG. 1 and consists of four cadherin-like domains followed by a cysteine-rich domain (See Borrello, M G, et al (2013), Expert Opin. Ther. Targets, 17(4):403-419). While the structure of the active RET signaling complex has not been solved, it appears that the GDNF/GFRα1 complex contacts the RET extracellular domain at multiple sites, including the fourth cadherin-like domain and the cysteine-rich domain. Thus, antibodies directed against multiple domains of RET could potentially inhibit signaling. Antibodies to RET have been described and can be found in U.S. Pat. No. 6,861,509 and US2009/0136502.

However, given the role that RET plays in tumor cell growth and proliferation, and given the fact that there are few agents approved to target this molecule, a need still exists for inhibitors of RET, for example, human antibodies that specifically bind to RET, which are highly potent and which produce no adverse effects that would preclude approval for clinical use.

BRIEF SUMMARY OF THE INVENTION

The invention provides fully human monoclonal antibodies (mAbs) or antigen-binding fragments thereof that bind specifically to RET and inhibit the binding or interaction of RET with one or more GDNF family member ligands (GDNF, neurturin, artemin, and persephin) complexed with their corresponding co-receptors (GFRα1, GFRα2, GFRα3, and GFRα4, respectively). In one embodiment, the human anti-RET antibodies described herein prevent the interaction of RET with the GDNF/GFRα1 complex. In a related embodiment, the human anti-RET antibodies described herein prevent the interaction of RET with the artemin/GFRα3 complex. In a related embodiment, the human anti-RET antibodies described herein prevent the interaction of RET with the neurturin/GFRα2 complex, or the persephin/GFRα4 complex.

The studies described herein have demonstrated that these antibodies are capable of modulating ligand dependent RET signaling. In certain embodiments, antibodies have been identified that antagonize ligand dependent RET signaling.

Given the role that RET plays in the development of multiple endocrine neoplastic syndromes, as well as in other cancers, the antibodies of the invention that antagonize/inhibit the signaling activity of RET may be used in the treatment of these neoplastic syndromes and cancers to inhibit the growth/proliferation of a tumor cell. Examples of cancerous conditions that may be treated using the RET antagonistic antibodies of the invention include, but are not limited to, thyroid tumors, lung tumors, pancreatic tumors, skin cancers, breast cancer and leukemias. A thyroid tumor that may be treatable using an antagonistic anti-RET antibody of the invention may include a papillary thyroid carcinoma (PTC) or a medullary thyroid carcinoma (MTC). The medullary thyroid carcinoma that may be treatable using an antagonistic anti-RET antibody of the invention may include a hereditary MTC selected from the group consisting of MEN2A, MEN2B and familial medullary thyroid carcinoma (FMTC) syndrome, or the medullary thyroid carcinoma may be a sporadic MTC. The antibodies of the invention may also be used to treat pain associated with these cancerous conditions, as well as pain associated with other diseases, disorders, or conditions in which RET activity or signaling may play a role.

The antibodies may be used as stand-alone therapy or may be used in conjunction with a second agent useful for treating a disease or disorder associated with RET expression. In certain embodiments, the antibodies may be given therapeutically in conjunction with a second agent to treat the disease or disorder, or to ameliorate at least one symptom associated with the disease or disorder. If the antibody inhibits RET activity or signaling and is under consideration for use in treating for example, a cancerous condition, the second agent may be a chemotherapeutic agent, or a bone marrow restorative agent, or may be radiation therapy to treat the tumor. If the antibody inhibits RET activity or signaling and is under consideration for treating pain associated with a certain condition, and if the treatment warrants the use of a second pain reducing agent, the second agent may be any agent that is also useful for alleviating pain associated with that condition, such as aspirin or another NSAID, morphine, steroids (e.g., prednisone), a nerve growth factor (NGF) inhibitor (e.g., a small molecule NGF antagonist or an anti-NGF antibody), an anti-$Na_v1.7$ antibody, or small molecule inhibitor of $Na_v1.7$, a $Na_v1.8$ antagonist (e.g., anti-$Na_v1.8$ antibody or small molecule inhibitor of $Na_v1.8$), a $Na_v1.9$ antagonist (e.g., anti-$Na_v1.9$ antibody or small molecule inhibitor of $Na_v1.9$), a cytokine inhibitor (e.g., an interleukin-1 (IL-1) inhibitor (such as rilonacept ("IL-1 trap") or anakinra (KINERET®), a small molecule IL-1 antagonist, or an anti-IL-1 antibody; an IL-18 inhibitor (such as a small molecule IL-18 antagonist or an anti-IL-18 antibody); an IL-6 or IL-6R inhibitor (such as a small molecule IL-6 antagonist, an anti-IL-6 antibody or an anti-IL-6 receptor antibody), inhibitors of caspase-1, p38, IKK1/2, CTLA-4Ig, or an opioid.

The antibodies of the invention can be full-length (for example, an IgG1 or IgG4 antibody) or may comprise only an antigen-binding portion (for example, a Fab, $F(ab')_2$ or scFv fragment), and may be modified to affect functionality, e.g., to eliminate residual effector functions (Reddy et al., (2000), J. Immunol. 164:1925-1933).

Accordingly, in a first aspect, the invention provides an isolated human monoclonal antibody or an antigen-binding fragment thereof that specifically binds to RET (REarranged during Transfection) receptor tyrosine kinase, wherein the antibody has one or more of the following characteristics:

(a) is a fully human antibody;
(b) exhibits a $K_D$ ranging from about $1.0\times10^{-7}$ M to about $1.0\times10^{-12}$ M as measured by Surface Plasmon Resonance;
(c) inhibits or blocks the binding, or interaction of RET with one or more GDNF family member ligands (GDNF, neurturin, artemin, and persephin) complexed with their corresponding co-receptors (GFRα1, GFRα2, GFRα3, and GFRα4, respectively);
(d) inhibits RET signaling mediated by one or more GDNF family member ligands selected from GDNF, neurturin, artemin, and persephin;
(e) enhances RET internalization/degradation following binding of the antibody to the RET receptor;
(f) comprises a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274 and 290; or
(g) comprises a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282 and 298.

In one embodiment, the isolated human monoclonal antibody or antigen-binding fragment thereof that specifically binds to RET blocks the binding of human RET to the GDNF:GFRα1 co-complex with an $IC_{50}$ value ranging from about 100 pM to about 7.0 nM.

In a related embodiment, the isolated human monoclonal antibody or antigen-binding fragment thereof that specifically binds to RET blocks the binding of human RET to the GDNF:GFRα1 co-complex with an $IC_{50}$ value ranging from about 250 pM to about 5.2 nM.

In one embodiment, the isolated human monoclonal antibody or antigen-binding fragment thereof that specifically binds to RET blocks the binding of human RET to the GDNF:GFRα1 co-complex by about 40% to about 100%.

In a related embodiment, the isolated human monoclonal antibody or antigen-binding fragment thereof that specifically binds to RET blocks the binding of human RET to the GDNF:GFRα1 co-complex by about 57% to about 97%.

In one embodiment, the isolated human monoclonal antibody or antigen-binding fragment thereof that specifically binds to RET inhibits GDNF-mediated RET signaling with an $IC_{50}$ value ranging from about 50 pM to greater than 100 nM.

In a related embodiment, the isolated human monoclonal antibody or antigen-binding fragment thereof that specifically binds to RET inhibits GDNF-mediated RET signaling with an $IC_{50}$ value ranging from about 143 pM to greater than 100 nM.

In one embodiment, the isolated human monoclonal antibody or antigen-binding fragment thereof that specifically binds to RET inhibits GDNF-mediated RET signaling by about 40% to about 100%.

In a related embodiment, the isolated human monoclonal antibody or antigen-binding fragment thereof that specifically binds to RET inhibits GDNF-mediated RET signaling by about 60% to about 100%.

In one embodiment, the isolated human monoclonal antibody or antigen-binding fragment thereof that specifically binds to RET inhibits artemin-mediated RET signaling with an $IC_{50}$ value ranging from about 100 pM to about 500 nM.

In a related embodiment, the isolated human monoclonal antibody or antigen-binding fragment thereof that specifically binds to RET inhibits artemin-mediated RET signaling with an $IC_{50}$ value ranging from about 250 pM to about 341 nM.

In one embodiment, the isolated human monoclonal antibody or antigen-binding fragment thereof that specifically binds to RET inhibits artemin-mediated RET signaling by about 57% to about 100%.

In one embodiment, the isolated human monoclonal antibody or antigen-binding fragment thereof that specifically binds to RET, comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274 and 290.

In one embodiment, the isolated human monoclonal antibody or antigen-binding fragment thereof that specifically binds to RET, comprises a light chain variable region (LCVR) having an amino acid sequence selected from the group consisting of SEQ ID NOs 10, 26, 42, 58, 74, 90, 106, 122, 138, 154, 170, 186, 202, 218, 234, 250, 266, 282 and 298.

In one embodiment, the isolated human monoclonal antibody or antigen-binding fragment thereof that specifically binds to RET, comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274 and 290; and a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282 and 298.

In one embodiment, the isolated human monoclonal antibody or antigen-binding fragment thereof that specifically binds to RET comprises a HCVR/LCVR amino acid sequence pair selected from the group consisting of SEQ ID NOs: SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282 and 290/298.

In one embodiment, the isolated human monoclonal antibody or antigen-binding fragment thereof that specifically binds to RET comprises a HCVR comprising the three heavy chain CDRs (HCDR1, HCDR2 and HCDR3) contained within a HCVR amino acid sequence selected from the group consisting of SEQ ID NO: 2, 18, 34, 50, 66, 82, 98, 114, 130, 146, 162, 178, 194, 210, 226, 242, 258, 274 and 290; and a LCVR comprising the three light chain CDRs (LCDR1, LCDR2 and LCDR3) contained within a LCVR amino acid sequence selected from the group consisting of SEQ ID NOs: 10, 26, 42, 58, 74, 90, 106, 122, 138, 154, 170, 186, 202, 218, 234, 250, 266, 282 and 298.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), J. Mol. Biol. 273:927-948; and Martin et al., (1989), Proc. Natl. Acad. Sci. USA 86:9268-9272. Public databases are also available for identifying CDR sequences within an antibody.

In one embodiment, the isolated human monoclonal antibody or antigen-binding fragment thereof that specifically binds to RET comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276 and 292;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278 and 294;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280 and 296;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284 and 300;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286 and 302; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288 and 304.

In one embodiment, the invention provides for an isolated antibody or antigen-binding fragment thereof that specifically binds to RET, which competes for specific binding to RET with an antibody or antigen-binding fragment comprising heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282 and 290/298.

In one embodiment, the invention provides for an isolated antibody or antigen-binding fragment thereof that specifically binds to RET, which binds the same epitope on RET that is recognized by an antibody comprising heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282 and 290/298.

In one embodiment, the invention provides a fully human monoclonal antibody or antigen-binding fragment thereof that specifically binds to RET, wherein the antibody or fragment thereof exhibits one or more of the following characteristics: (i) comprises a HCVR having an amino acid sequence selected from the group consisting of SEQ ID NOs: 2, 18, 34, 50, 66, 82, 98, 114, 130, 146, 162, 178, 194, 210, 226, 242, 258, 274 and 290, or a substantially similar sequence thereof having at least 90%, at least 95%, at least 98% or at least 99% sequence identity; (ii) comprises a LCVR having an amino acid sequence selected from the group consisting of SEQ ID NOs: 10, 26, 42, 58, 74, 90, 106, 122, 138, 154, 170, 186, 202, 218, 234, 250, 266, 282 and 298, or a substantially similar sequence thereof having at least 90%, at least 95%, at least 98% or at least 99% sequence identity; (iii) comprises a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280 and 296, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288 and 304, or a substantially similar sequence thereof having at least 90%, at least 95%, at least 98% or at least 99% sequence identity; (iv) comprises a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276 and 292, or a substantially similar sequence thereof having at least 90%, at least 95%, at least 98% or at least 99% sequence identity; (v) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278 and 294, or a substantially similar sequence thereof having at least 90%, at least 95%, at least 98% or at least 99% sequence identity; (vi) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284 and 300, or a substantially similar sequence thereof having at least 90%, at least 95%, at least 98% or at least 99% sequence identity; (vii) and a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286 and 302, or a substantially similar sequence thereof having at least 90%, at least 95%, at least 98% or at least 99% sequence identity; (viii) exhibits a $K_D$ ranging from about $1\times10^{-7}$ M to about $1\times10^{-12}$M; (ix) is capable of blocking the binding of human RET to the GDNF:GFRα1 co-complex with an $IC_{50}$ value of less than about 5.2 nM; or (x) demonstrates the ability to inhibit ligand dependent RET signaling by about 60 to 100% with an $IC_{50}$ value ranging from about 143 pM to greater than 100 nM.

In a second aspect, the invention provides nucleic acid molecules encoding antibodies or fragments thereof that specifically bind to RET. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273 and 289 or a substantially identical sequence having at least 90%, at least 95%, at least 98%, or at least 99% homology thereof.

In one embodiment, the antibody or fragment thereof further comprises a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281 and 297, or a substantially identical sequence having at least 90%, at least 95%, at least 98%, or at least 99% homology thereof.

In one embodiment, the invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279 and 295, or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287 and 303, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275 and 291, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277 and 293, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283 and 299, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285 and 301, or a substantially similar sequence thereof having at least 90%, at least 95%, at least 98% or at least 99% sequence identity.

In a third aspect, the invention features a human antibody or antigen-binding fragment specific for RET comprising a HCVR encoded by nucleotide sequence segments derived from $V_H$, $D_H$ and $J_H$ germline sequences, and a LCVR encoded by nucleotide sequence segments derived from $V_K$ and $J_K$ germline sequences.

The invention encompasses antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, modification of galactosylation can be made in order to modify complement dependent cytotoxicity (CDC).

In a fourth aspect, the invention provides a pharmaceutical composition comprising at least one isolated fully human monoclonal antibody or antigen-binding fragment thereof that binds to RET and a pharmaceutically acceptable carrier or diluent. In one embodiment, the invention provides a pharmaceutical composition comprising two fully human monoclonal antibodies or antigen-binding fragments thereof, which either bind to the same epitope or bind to two different epitopes on RET and a pharmaceutically acceptable carrier or diluent. It is to be understood that any combination of antibodies as described herein may be used in a pharmaceutical composition to achieve the desired results in the patient population in need of such therapy. For example, two antibodies that recognize and/or bind RET may be used in a composition.

In one embodiment, the composition comprises an antibody that binds RET and has a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282 and 290/298.

In one embodiment, the pharmaceutical composition comprises at least one antibody that binds RET, wherein the antibody comprises the three heavy chain complementarity determining regions (HCDR1, HCDR2 and HCDR3) contained within any one of the heavy chain variable region (HCVR) amino acid sequences selected from the group consisting of SEQ ID NOs: 2, 18, 34, 50, 66, 82, 98, 114, 130, 146, 162, 178, 194, 210, 226, 242, 258, 274 and 290; and the three light chain complementarity determining regions (LCDR1, LCDR2 and LCDR3) contained within any one of the light chain variable region (LCVR) amino acid sequences selected from the group consisting of SEQ ID NOs: 10, 26, 42, 58, 74, 90, 106, 122, 138, 154, 170, 186, 202, 218, 234, 250, 266, 282 and 298.

In one embodiment, the antibodies of the invention, or compositions containing one or more antibodies of the invention may be used to inhibit at least one activity or function associated with RET expressed on a cell. In one embodiment, the cell may be a tumor cell. In one embodiment, the activity may be cell signaling.

In one embodiment, the invention features a composition, which is a combination of an antibody or antigen-binding fragment of an antibody of the invention, and a second therapeutic agent.

The second therapeutic agent may be a small molecule drug, a protein/polypeptide, an antibody, a nucleic acid molecule, such as an anti-sense molecule, or a siRNA. The second therapeutic agent may be synthetic or naturally derived.

The second therapeutic agent may be any agent that is advantageously combined with the antibody or fragment thereof of the invention, for example, if the anti-RET antibody is an inhibitor of RET to be used to treat a cancerous condition, the second agent may be selected from a chemotherapeutic agent, a radionuclide, an siRNA specific for RET, a second antibody specific for RET, a small molecule RET inhibitor, and a bone marrow restorative agent, such as G-CSF, GM-CSF, or M-CSF, or biological agents having colony stimulating, or bone marrow restorative activity. In certain embodiments, the second therapeutic agent may be an agent that helps to counteract or reduce any possible side effect(s) associated with the antibody or antigen-binding fragment of an antibody of the invention, if such side effect(s) should occur. In certain embodiments, the second therapeutic agent may be an agent useful for diminishing pain associated with certain conditions characterized by pain and/or inflammation. Such second agent may include a nerve growth factor (NGF) inhibitor (e.g., a small molecule NGF antagonist or an anti-NGF antibody), aspirin or another NSAID, morphine, steroids (e.g., prednisone), an anti-$Na_v1.7$ antibody, or small molecule inhibitor of $Na_v1.7$, a $Na_v1.8$ antagonist (e.g., anti-$Na_v1.8$ antibody or small molecule inhibitor of $Na_v1.8$), a $Na_v1.9$ antagonist (e.g., anti-$Na_v1.9$ antibody or small molecule inhibitor of $Na_v1.9$), a cytokine inhibitor (e.g., an interleukin-1 (IL-1) inhibitor (such as rilonacept ("IL-1 trap"); Regeneron) or anakinra (KINERET®, Amgen), a small molecule IL-1 antagonist, or an anti-IL-1 antibody; an IL-18 inhibitor (such as a small molecule IL-18 antagonist or an anti-IL-18 antibody); an IL-6 or IL-6R inhibitor (such as a small molecule IL-6 antagonist, an anti-IL-6 antibody or an anti-IL-6 receptor antibody), inhibitors of caspase-1, p38, IKK1/2, CTLA-4Ig, or an opioid.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

If it is contemplated that a small molecule RET inhibitor is to be combined with an antibody of the invention, the small molecule RET inhibitor may be selected from the group consisting of vandetanib, sorafenib, sunitinib, cabozantinib, motesanib, RPI-1, PP-1 and NVP-AST478, cediranib, (AZD2171), gefitinib, erlotinib, SU14813, vatalanib, (BAY43-9006), XL-647, XL-999, AG-013736, BIBF1120, TSU68, GW786034, AEE788, CP-547632, KRN951, CHIR258, CEP-7055, OSI-930, ABT-869, E7080, ZK-304709, BAY57-9352, L-21649, BMS582664, XL-880, XL-184, XL-820, RPI-1, PP-1 and NVP-AST478.

When multiple therapeutics are co-administered, dosages may be adjusted accordingly, as is recognized in the pertinent art.

A fifth aspect of the invention provides a method for treating a disorder or condition associated with expression, activation or signaling of the RET receptor tyrosine kinase gene, or a rearranged form thereof, or the pain associated with the disorder or condition, the method comprising administering an antibody or antigen-binding fragment of any of the anti-RET antibodies described herein together with a pharmaceutically acceptable carrier or diluent to a patient in need thereof.

In one embodiment, the disorder or condition is a cancer selected from the group consisting of thyroid cancer, lung cancer, pancreatic cancer, skin cancer, breast cancer and a blood-borne cancer. In one embodiment, the disorder or condition associated with expression, activation or signaling of the RET receptor tyrosine kinase gene, or a rearranged form thereof is selected from the group consisting of acute pain, chronic pain, neuropathic pain, inflammatory pain, arthritis, osteoarthritis, migraine, cluster headaches, trigeminal neuralgia, herpetic neuralgia, general neuralgias, neurodegenerative disorders, neuroendocrine disorders, visceral pain, acute gout, post-herpetic neuralgia, diabetic neuropathy, sciatica, back pain, head or neck pain, severe or intractable pain, breakthrough pain, post-surgical pain, dental pain, rhinitis, cancer pain, or bladder disorders.

In a related aspect, the invention provides a method for inhibiting tumor growth or tumor cell proliferation, wherein the tumor or tumor cell expresses RET, or a rearranged form thereof, the method comprising administering an antibody or an antigen-binding fragment thereof of the invention to a patient in need thereof.

In one embodiment, the tumor is a solid tumor or a blood-borne tumor.

In one embodiment, the solid tumor is selected from the group consisting of a thyroid tumor, a lung tumor, a pancreatic tumor, a skin tumor and a breast tumor.

In one embodiment, the thyroid tumor is a papillary thyroid carcinoma (PTC) or a medullary thyroid carcinoma (MTC).

In one embodiment, the medullary thyroid carcinoma is a hereditary MTC selected from the group consisting of MEN2A, MEN2B and familial medullary thyroid carcinoma (FMTC) syndrome, or wherein the medullary thyroid carcinoma is a sporadic MTC.

In one embodiment, the lung tumor is a lung adenocarcinoma.

In one embodiment, the lung tumor is a non-small cell lung cancer (NSCLC).

In one embodiment, the skin tumor is a melanoma.

In one embodiment, the blood-borne tumor is a leukemia.

In one embodiment, the leukemia is chronic myelomonocytic leukemia.

In a related aspect, the invention provides a method of down-modulating RET expression and/or function, the method comprising administering an antibody or an antigen-binding fragment thereof of the invention.

In one embodiment, the down-modulating of RET expression and/or function results in down-regulation of a downstream signaling pathway selected from the group consisting of the RAS/RAF/ERK and the PI3K pathways. In certain embodiments, the down-modulating of RET expression and/or function results in down-regulation of a signaling pathway selected from the group consisting of the PKC, SRC and STAT3 pathways.

In one embodiment, an anti-RET antibody of the invention may interfere with, or prevent, the interaction between RET and one or more GDNF family member ligands (GDNF, neurturin, artemin, and persephin) complexed with their corresponding co-receptors (GFRα1, GFRα2, GFRα3, and GFRα4, respectively). In one embodiment, the human anti-RET antibodies described herein may interfere with, or prevent the interaction of RET with the GDNF/GFRα1 complex. In a related embodiment, the human anti-RET antibodies described herein may interfere with, or prevent the interaction of RET with the artemin/GFRα3 complex. In other related embodiments, the human anti-RET antibodies described herein may interfere with, or prevent the interaction of RET with the neurturin/GFRα2, or the persephin/GFRα4 complexes.

Once activated, RET recruits a variety of signaling molecules that mediate biological responses. RET can activate various signaling pathways, such as RAS/RAF/ERK (extracellular signal-regulated kinase), phosphatidylinositol 3-kinase (PI3K)/AKT, PKC and SRC. These signaling pathways are activated via binding of adaptor proteins to intracellular tyrosine residues of RET phosphorylated by its own kinase activity.

Accordingly, in certain aspects of the invention, an anti-RET antibody of the invention may block the biological responses attributed at least in part to activation of other signaling pathways by RET. In certain embodiments, an anti-RET antibody of the invention may interfere with the signal transduction through a pathway comprising RET and RAS. In certain embodiments, an anti-RET antibody may interfere with cell proliferation, migration, or invasion, or the phosphorylation of ERK1/2 (Extracellular Signal-Regulated Kinase 1/2). In some embodiments, an anti-RET antibody may interfere with the signal transduction through a pathway comprising RET and PI3K (phosphatidylinositol-3-Kinase). In certain embodiments, an anti-RET antibody may interfere with cell proliferation, migration, or invasion, or the phosphorylation of Akt (protein kinase B).

The antibody or antigen-binding fragment may be administered to the patient in combination with a second therapeutic agent suitable for treating the disease, disorder or condition. If the disease or condition to be treated by an anti-RET antibody is a cancerous condition, the second therapeutic agent may be selected from the group consisting of a chemotherapeutic agent, a radionuclide (alone, or as part of a drug targeting regimen), an antibody-drug conjugate, a small molecule RET inhibitor, an anti-tumor agent, an siRNA specific for RET, and a second antibody specific for RET. If an anti-RET antibody is envisioned for treating pain associated with the cancerous condition, or for treating pain associated with other conditions that may be attributed at least in part to RET activation or signaling, the second therapeutic agent may be selected from any one or more of the following: a nerve growth factor (NGF) inhibitor (e.g., a small molecule NGF antagonist or an anti-NGF antibody), aspirin or another NSAID, morphine, steroids (e.g., prednisone), an anti-$Na_v1.7$ antibody, or small molecule inhibitor of $Na_v1.7$, a $Na_v1.8$ antagonist (e.g., anti-$Na_v1.8$ antibody or small molecule inhibitor of $Na_v1.8$), a $Na_v1.9$ antagonist (e.g., anti-$Na_v1.9$ antibody or small molecule inhibitor of $Na_v1.9$), a cytokine inhibitor (e.g., an interleukin-1 (IL-1) inhibitor (such as rilonacept ("IL-1 trap"); Regeneron) or anakinra (KINERET®, Amgen), a small molecule IL-1 antagonist, or an anti-IL-1 antibody; an IL-18 inhibitor (such as a small molecule IL-18 antagonist or an anti-IL-18 antibody); an IL-6 or IL-6R inhibitor (such as a small molecule IL-6 antagonist, an anti-IL-6 antibody or an anti-IL-6 receptor antibody), inhibitors of caspase-1, p38, IKK1/2, CTLA-4Ig, or an opioid.

Other embodiments will become apparent from a review of the ensuing detailed description.

BRIEF DESCRIPTION OF THE FIGURES

FIG. 1. A schematic diagram of the human RET receptor.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described. All publications mentioned herein are incorporated herein by reference in their entirety.

Definitions

"REarranged during Transfection", also referred to as "RET" is a receptor tyrosine kinase that is expressed during development in a variety of tissues, including the peripheral and central nervous systems and the kidney. The RET oncogene was identified in 1985 by Takahashi et al., who reported on a novel gene rearrangement with transforming activity in NIH/3T3 cells that were transfected with human lymphoma DNA (See Takahashi, M., et al., (1985) Cell, 42:581-588). RET was later confirmed to be an oncogene, being somatically rearranged in DNA of papillary thyroid carcinoma (PTC) patients and later designated as RET/PTCs. (Fusco, A. et al., (1987), Nature, 328:170-172; Grieco, M. et al., (1990), Cell, 60:557-63). RET protein is composed of three domains: an extracellular ligand-binding domain, a hydrophobic transmembrane domain and a cytoplasmic portion with the tyrosine kinase domain split by an insertion of 27 amino acids (See FIG. 1). There are two main isoforms of RET generated by alternative splicing. The short and long RET isoforms, which differ by 9 and 51 unrelated C-terminal amino acids, are referred to as RET9 and RET51, respectively. They are highly conserved over a broad range of species (Carter, M T, et al. (2001), Cytogenet Cell Genet, 95:169-76). Both isoforms display transforming activity by focus formation assay (Rossel, M. et al. (1997), Oncogene, 14:265-75).

The cDNA sequence and the amino acid sequence of isoform A of RET (also known as RET51) is provided in GenBank as accession numbers NM_020975.4 and NP_066124.1, respectively, and are provided herein as SEQ ID NOs: 309 and 310, respectively.

The cDNA sequence and the amino acid sequence of isoform C of RET (also known as RET9) is provided in GenBank as accession numbers NM_020630.4 and NP_065681.1, respectively, and are provided herein as SEQ ID NOs: 311 and 312, respectively. RET, or immunogenic fragments thereof, may be used in preparing human monoclonal antibodies specific for RET. The RET protein, or fragments thereof may be recombinantly produced using standard methods known in the art. Exemplary fusion proteins containing the ecto-domain of RET are shown as SEQ ID NOs: 305, 306, 307 and 309. These fusion proteins may be used as immunogens, or they may be used to target therapeutic agents to cells or tissues expressing RET.

RET is the signaling receptor for ligands of the "glial-derived neurotrophic factor (GDNF) family", which comprises GDNF (See GenBank accession No. NP_000505.1), artemin (See GenBank accession No. Q5T4W7), neurturin (See GenBank accession No. NM_004558), and persephin (See GenBank accession No. AF040962). GDNF family ligands interact with and activate RET only in the presence of, or complexed with, one of four GPI-linked "co-receptors", known as GDNF family Q receptors GFRα1 (See GenBank accession No. NP_005255.1), GFRα2 (See GenBank accession No. NM_001495.4), GFRα3 (See GenBank accession No. NP_001487.2), and GFRα4 (See GenBank accession No. NM_022139 for GFRα4a and NM_145762.2 for GFRα4b), (Baloh, R H, et al. (2000), Curr Opin Neurobiol 10:103-110; Borrello, M G, et al (2013), Expert Opin. Ther. Targets, 17(4):403-419). The primary ligands for the co-receptors GFRα1, GFRα2, GFRα3 and GFRα4 are GDNF, neurturin (NRTN), artemin (ARTN) and persephin (PSPN), respectively.

The term "$IC_{50}$" refers to the "half maximal inhibitory concentration", which value measures the effectiveness of compound (e.g. anti-RET antibody) inhibition towards a biological or biochemical utility. This quantitative measure indicates the quantity required for a particular inhibitor to inhibit a given biological process by half.

As used herein, the terms "treat," "treatment" and "treating" refer to either the reduction in progression of a disease, disorder, or condition attributed to in part, or associated with RET expression in a cell or tissue in a subject, for example, slowing the rate of tumor cell proliferation in patients bearing a tumor that expresses RET, when administered an antagonistic/inhibitory antibody of the invention, or reduction in the pain associated with a cancerous condition, or pain associated with any other disease or condition which is caused at least in part by RET expression.

As used herein, the terms "prevent," "preventing," and "prevention" refer to the inhibition of the development or onset of a disease, disorder, or condition attributed to in part, or associated with, RET expression in a cell or tissue in a subject, for example, certain cancers, or the inhibition of tissue damage that occurs in a patient after an injury, or the inhibition or amelioration of pain associated with a disease or condition attributed to in part RET expression.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully monoclonal antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to RET. Moreover, multi-specific antibodies that bind to RET protein and one or more additional antigens or a bi-specific that binds to two different regions of RET are nonetheless considered antibodies that "specifically bind", as used herein.

The term "high affinity" antibody refers to those mAbs having a binding affinity to RET, expressed as $K_D$, of at least $10^{-7}$ M, of at least $10^{-8}$ M; preferably $10^{-9}$ M; more preferably $10^{-10}$M, more preferably $10^{-11}$M, more preferably $10^{-12}$M as measured by surface plasmon resonance, e.g., BIACORE™ or solution-affinity ELISA.

By the term "slow off rate", "Koff" or "kd" is meant an antibody that dissociates from RET, with a rate constant of $1\times10^{-3}$ $s^{-1}$ or less, preferably $1\times10^{-4}$ $s^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retains the ability to bind to RET.

The specific embodiments, antibody or antibody fragments of the invention may be conjugated to a therapeutic moiety ("immunoconjugate" or "antibody-drug conjugate"), such as a small molecule RET inhibitor, an anti-tumor agent, a radionuclide, a growth factor, a bone marrow restorative agent or colony stimulating factor, or any other therapeutic moiety useful for treating a disease, disorder, or condition associated with RET expression, such as a cancer, or a damaged tissue.

An "isolated antibody", as used herein, is intended to refer to an antibody that is substantially free of other antibodies (Abs) having different antigenic specificities (e.g., an isolated antibody that specifically binds RET, or a fragment thereof, is substantially free of Abs that specifically bind antigens other than RET.

A "blocking antibody" or a "neutralizing antibody", as used herein (or an "antibody that neutralizes RET activity"), is intended to refer to an antibody whose binding to RET results in inhibition of at least one biological activity of RET, such as cell signaling. For example, an antibody of the invention may aid in blocking the binding of RET to its ligand, or to one of the GFRα co-receptors, or prevent or treat a disease associated with RET expression. Alternatively, an antibody of the invention may demonstrate the ability to ameliorate at least one symptom of the disease or condition associated with RET expression. This inhibition of the biological activity of RET can be assessed by measuring one or more indicators of RET biological activity by one or more of several standard in vitro assays (such as any of the assays as described herein) or in vivo assays known in the art (for example, animal models to look at inhibition of tumor cell growth in vivo) following administration of one or more of the antibodies described herein.

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402, each of which is herein incorporated by reference.

In specific embodiments, the antibody or antibody fragment for use in the method of the invention may be mono-specific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase “therapeutically effective amount” is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

General Description

“REarranged during Transfection”, also referred to as “RET” is a receptor tyrosine kinase that is expressed during development in a variety of tissues, including the peripheral and central nervous systems and the kidney (Arighi, E. et al. (2005), Cytokine Growth Factor Rev 16:441-67; Borrello, M G, et al., (2013), Expert Opin. Ther. Targets, 17(4): 403-419). The RET oncogene was identified in 1985 by Takahashi et al., who reported on a novel gene rearrangement with transforming activity in NIH/3T3 cells that were transfected with human lymphoma DNA (See Takahashi, M., et al., (1985) Cell, 42:581-588). RET was later confirmed to be an oncogene, being somatically rearranged in DNA of papillary thyroid carcinoma (PTC) patients and later designated as RET/PTCs. (Fusco, A. et al., (1987), Nature, 328:170-172; Grieco, M. et al., (1990), Cell, 60:557-63). RET protein is composed of three domains: an extracellular ligand-binding domain, a hydrophobic transmembrane domain and a cytoplasmic portion with the tyrosine kinase domain split by an insertion of 27 amino acids (See FIG. 1). There are two main isoforms of RET generated by alternative splicing. The short and long RET isoforms, which differ by 9 and 51 unrelated C-terminal amino acids, are referred to as RET9 and RET51, respectively. They are highly conserved over a broad range of species (Carter, M T, et al. (2001), Cytogenet Cell Genet, 95:169-76). Both isoforms display transforming activity by focus formation assay (Rossel, M. et al. (1997), Oncogene, 14:265-75).

Genetic alterations of RET have been shown to be involved in the etiology of thyroid cancers and more recent data suggests that RET is also involved in lung adenocarcinomas (Viglietto, G. et al. (1995), Oncogene, 11:1207-10; Fischer, A H, et al., (1998), Am J Pathol. 153:1443-50). Other studies suggest that RET may be involved in additional tumors, including breast, pancreas, leukemias and melanoma (Ballerini, P. et al, (2012), Leukemia, 26:2384-9; Sawai, H. et al. (2005), 65(24):11536-44; Narita, N. et al., (2009), Oncogene, 28:3058-68).

Vandetanib (ZD6474, CAPRELSA®, Astra Zeneca), is an orally available aminoquinazoline compound, which was initially developed as a VEGFR2 inhibitor, but was later found to be active against RET, VEGFR3, EGFR and PDGFR. Vandetanib is currently approved by the FDA and EMA for advanced and metastatic medullary thyroid carcinoma (MTC) (Wells, S A, et al., (2012), J. Clin. Oncol. 30:134-41).

Sorafenib (BAY43-9006, NEXAVAR®, Bayer Pharmaceuticals) is a bisarylurea compound initially developed to target the serine/threonine kinase BRAF, but was subsequently found to be a potent agent against Flt-3, VEGFR1-3, PDGFR, c-kit and RET (Wilhelm, S. et al., (2006), Nat Rev Drug Discov, 5:835-44). Sorafenib was approved by the FDA for advanced liver and kidney cancers.

Sunitinib (SU11248, SUTENT®, Pfizer) is an indolinone compound that targets mainly VEGFR2, PDGFR, c-kit, FLT3 and RET kinases ((Chow, L O, et al., (2007), J. Clin. Oncol. 25:884-96). Sunitinib was approved by the FDA for imatinib-resistant GIST patients, as well as for advanced pancreatic neuroendocrine tumors and renal cell cancer.

Cabozantinib (Cometriq, formerly known as XL-184, Exelixis) is a small-molecule, multikinase inhibitor that targets MET, VEGFR2 and RET. It is currently in clinical trials in a large number of tumor types, including medullary thyroid cancer, prostate cancer, ovarian cancer, non-small cell lung cancer (NSCLC), hepatocellular, renal cell and breast cancer, as well as melanoma and glioblastoma ((Zhang, Y. et al., (2010), IDrugs 13:112-21).

Another RET-targeting agent in clinical development is motesanib (AMG-706, Amgen), which is a multikinase inhibitor that targets VEGFR1-3, Flt3, Kit, PDGFR and RET.

Other RET inhibitors in pre-clinical development are RPI-1, which is an indoline compound; PP-1, which is a pyrazolopyrimidine compound active on RET and Src; and NVP-AST478, which is a biphenyl-urea compound that has potent anti-RET kinase activity in vitro and in vivo (Cuccuru, G. et al. (2004), J Natl Cancer Inst 96:1006-14).

However, one problematic aspect of the above-noted RET inhibitors is that they are not specific for RET, that is, they appear to act through multiple mechanisms and as such, could potentially exert other untoward effects in vivo. For example, certain of the inhibitors noted above induce adverse events such as hypertension and QTc prolongation. Thus, the non-selective profile of these agents may limit the therapeutic window. It would be of benefit to identify agents, such as an anti-RET antibody that selectively binds to RET, which could result in superior clinical efficacy with a more favorable safety profile.

Accordingly, there is still a need for effective therapies against RET-driven tumors, and furthermore, there is a need to identify an agent specific for RET for preventing and treating other diseases, disorders, or conditions associated with RET expression without the adverse side effects associated with the agents described above. Such specificity and efficacy may be achieved through use of an anti-RET antibody, such as those described herein.

In certain embodiments, the antibodies of the invention are obtained from mice immunized with a primary immunogen, such as a whole human RET protein, or with a recombinant form of the protein, or a fragment thereof, or with a fusion protein that contains the extracellular/ecto-domain of human RET. (See GenBank accession number NP_066124.1 (SEQ ID NO: 310) or GenBank accession number NP_065681.1 (SEQ ID NO: 312), or a recombinantly produced RET fusion protein (See SEQ ID NOs: 305, 306, 307 and 313), followed by immunization with a secondary immunogen (purified human RET protein), or with an immunogenically active fragment of the RET protein, such as the ecto-domain of RET.

The immunogen may be DNA encoding the human RET protein (See GenBank accession number NM_020975.4 and SEQ ID NO: 309 for isoform A; or GenBank accession number NM_020630.4 and SEQ ID NO: 311 for isoform C) or an active fragment thereof.

The immunogen may be derived from the extracellular domain of the RET protein, which spans amino acid residues 1-635 of any of SEQ ID NOs: 305, 307, 310, 312, and 313 (including the signal sequence); from amino acid residue 1-636 of SEQ ID NO: 306 (including the signal sequence). An immunogen may be derived from a fragment of any of the above-noted regions of the RET protein.

The full-length amino acid sequence of RET51 is shown as SEQ ID NO: 310 and is also shown in GenBank accession number NP_066124.1. The full-length amino acid sequence of RET9 is shown as SEQ ID NO: 312 and is also shown in GenBank accession number NP_065681.1. Exemplary immunogens may be the recombinant constructs shown in SEQ ID NOs: 307 or 313.

In certain embodiments, antibodies that bind specifically to RET may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of RET specific antibodies. In certain embodiments, any one or more of the above-noted regions of RET, or fragments thereof may be used for preparing monospecific, bispecific, or multispecific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to RET. An antibody fragment may include a Fab fragment, a $F(ab')_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$ and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in noncovalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to RET.

Using VELOCIMMUNE® technology (see, for example, U.S. Pat. No. 6,596,541, Regeneron Pharmaceuticals, VELOCIMMUNE®) or any other known method for generating monoclonal antibodies, high affinity chimeric antibodies to RET are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In certain embodiments, the antibodies of the instant invention possess affinities ($K_D$) ranging from about $1.0\times10^{-7}$ M to about $1.0\times10^{-12}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-RET antibodies and antibody fragments of the present invention encompass proteins having amino acid sequences that vary from those of the described antibodies, but that retain the ability to bind RET. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-RET Antibodies Comprising Fc Variants

According to certain embodiments of the present invention, anti-RET antibodies are provided comprising an Fc domain comprising one or more mutations, which enhance or diminish antibody binding to the FcRn receptor, e.g., at acidic pH as compared to neutral pH. For example, the present invention includes anti-RET antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 2500 and 428L modification (e.g., T2500 and M428L); and a 307 and/or 308 modification (e.g., 308F or 308P).

For example, the present invention includes anti-RET antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies

In general, the antibodies of the present invention may function by binding to RET and in so doing act to block, or prevent RET activation and/or signaling. The antibodies of the present invention may also function by binding to RET and in so doing interfere with, or prevent the interaction, or binding of RET with one or more GDNF family members complexed with their corresponding co-receptors, e.g GDNF/GFRα1, neurturin/GFRα2, artemin/GFRα3, or persephin/GFRα4. Based on the fact that the tumorigenic potential of RET has been established in humans, an antagonistic antibody that specifically binds to RET may prove to have a beneficial effect in inhibiting tumor cell growth in patients suffering from a cancerous condition.

In certain embodiments, the antibodies of the present invention may function by blocking or inhibiting RET activity by binding to any region or fragment of the full length protein, the amino acid sequence of which is shown in SEQ ID NO: 310 (RET51), also shown as GenBank accession number NP_066124.1 and in SEQ ID NO: 312 (RET9), also shown as GenBank accession number NP_065681.1. The antibodies may also bind to any region which is found in SEQ ID NO: 310 or 312, or to a fragment found within SEQ ID NO: 310 or 312.

In one embodiment, the invention provides a fully human monoclonal antibody or antigen-binding fragment thereof that binds to the RET protein, wherein the antibody or fragment thereof exhibits one or more of the following characteristics:

(a) is a fully human antibody;

(b) exhibits a $K_D$ ranging from about $1.0\times10^{-7}$ M to about $1.0\times10^{-12}$ M as measured by Surface Plasmon Resonance;

(c) inhibits or blocks the binding, or interaction of RET with one or more GDNF family member ligands (GDNF, neurturin, artemin, and persephin) complexed with their corresponding co-receptors (GFRα1, GFRα2, GFRα3, and GFRα4, respectively);

(d) inhibits RET signaling mediated by one or more GDNF family member ligands selected from GDNF, neurturin, artemin, and persephin;

(e) enhances RET internalization/degradation following binding of the antibody to the RET receptor;

(f) comprises a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274 and 290; or (g) comprises a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282 and 298.

Certain anti-RET antibodies of the present invention are able to bind to the RET protein and inhibit the activation and/or signaling associated with RET. In so doing, the antibodies may function to inhibit the growth of tumors that depend on activation of RET signaling for growth. Such antagonistic anti-RET antibodies may be used alone to treat a cancerous condition, or may be used as adjunct therapy with any other anti-cancer agent, such as a chemotherapeutic small molecule, or radiation therapy, or with a bone marrow restorative agent.

In certain embodiments, the anti-RET antibodies may be capable of inhibiting multiple signaling pathways, including RAS/RAF pathway, which leads to activation of the mitogen activated protein kinases (MAPK) ERK1 and ERK2 (Trupp, M. et al., (1999), J Biol. Chem. 274:20885-94; Santoro, M. et al., (1994), Mol. Cell Biol. 14:663-75; van Weering, D H J, et al. (1995), 11:2207-14; Worby, C A, et al., (1996), J Biol Chem, 271:23619-22), phosphatidylinositol 3-kinase (PI3K), resulting in activation of the serine/threonine kinase Akt (Trupp, M. et al., (1999), J Biol. Chem. 274:20885-94; van Weering, D H J, (1997), J Biol Chem 272:249-54; Segouffin-Cariou, C., et al, (2000), 275:3568-76; Maeda, K. et al, (2004), 323: 345-54).

Non-limiting, exemplary in vitro assays for measuring the ability of the anti-RET antibodies of the invention to block the binding of RET to the GFRα1/GDNF co-complex and in vitro assays to measure the effect of the antibodies on RET signaling, activation, or internalization are illustrated in Examples 4 and 5, respectively. In Example 3, the binding affinities and kinetic constants of human anti-RET antibodies were determined by surface plasmon resonance and the measurements were conducted on a Biacore 4000 or T200 instrument. In Example 4, the ability of the antibodies to block the binding of RET to the GFRα1/GDNF co-complex was tested using a competition sandwich ELISA assay. Example 5 demonstrates the ability of the antibodies of the invention to inhibit ligand dependent RET signaling in a serum-response factor (SRE)-luciferase reporter assay. More particularly, the data presented in Example 5 show that the anti-RET antibodies of the invention display a range of inhibitory activity on RET signaling in the presence of the glial family ligands, GDNF and artemin.

Epitope Mapping and Related Technologies

Various techniques known to persons of ordinary skill in the art can be used to determine whether an antibody "interacts with one or more amino acids" within a polypeptide or protein. Exemplary techniques include, for example, a routine cross-blocking assay such as that described Antibodies, Harlow and Lane (Cold Spring Harbor Press, Cold Spring Harb., NY) can be performed. Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues that correspond to the specific amino acids with which the antibody interacts. See, e.g., Ehring (1999) *Analytical Biochemistry* 267(2):252-259; Engen and Smith (2001) *Anal. Chem.* 73:256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

The present invention includes anti-RET antibodies that bind to the same epitope as any of the specific exemplary antibodies described herein in Table 1. Likewise, the present invention also includes anti-RET antibodies that compete for binding to RET or a fragment thereof with any of the specific exemplary antibodies described herein in Table 1.

One can easily determine whether an antibody binds to the same epitope as, or competes for binding with, a reference anti-RET antibody by using routine methods known in the art. For example, to determine if a test antibody binds to the same epitope as a reference RET antibody of the invention, the reference antibody is allowed to bind to a RET protein or peptide under saturating conditions. Next, the ability of a test antibody to bind to the RET molecule is assessed. If the test antibody is able to bind to RET following saturation binding with the reference anti-RET antibody, it can be concluded that the test antibody binds to a different epitope than the reference anti-RET antibody. On the other hand, if the test antibody is not able to bind to the RET molecule following saturation binding with the reference anti-RET antibody, then the test antibody may bind to the same epitope as the epitope bound by the reference anti-RET antibody of the invention.

To determine if an antibody competes for binding with a reference anti-RET antibody, the above-described binding methodology is performed in two orientations: In a first orientation, the reference antibody is allowed to bind to a RET molecule under saturating conditions followed by assessment of binding of the test antibody to the RET molecule. In a second orientation, the test antibody is allowed to bind to a RET molecule under saturating conditions followed by assessment of binding of the reference antibody to the RET molecule. If, in both orientations, only the first (saturating) antibody is capable of binding to the RET molecule, then it is concluded that the test antibody and the reference antibody compete for binding to RET. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human RET monoclonal antibody conjugated to a therapeutic moiety ("immunoconjugate"), such as an agent that is capable of inhibiting the proliferation of tumor cells, or to ameliorate at least one symptom associated with a RET associated condition, such as a cancerous condition. Such an agent may be a second different antibody to RET, or an anti-tumor chemotherapeutic agent, or may be a radionuclide that when targeted to a tumor cell expressing RET acts to kill the tumor cell. The type of therapeutic moiety that may be conjugated to the anti-RET antibody and will take into account the condition to be treated and the desired therapeutic effect to be achieved. Alternatively, if the desired therapeutic effect is to treat the sequelae or symptoms associated with expression of RET by certain tissues, or any other condition resulting from RET expression, such as, but not limited to, cancer, it may be advantageous to conjugate an agent appropriate to treat the sequelae or symptoms of the condition, or to alleviate any side effects of the antibodies of the invention. Examples of suitable agents for forming immunoconjugates are known in the art, see for example, WO 05/103081.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity.

An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise a Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Administration and Formulations

The invention provides therapeutic compositions comprising the anti-RET antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of each of the antibodies of the invention may vary depending upon the age and the size of a subject to be administered, target disease, conditions, route of administration, and the like. When the antibodies of the present invention are used for treating a RET associated disease, or condition in a patient, or for treating one or more symptoms associated with a condition that depends on RET activation or signaling, such as certain tumors expressing RET in a patient, or for lessening the severity of the disease, it is advantageous to administer each of the antibodies of the present invention intravenously or subcutaneously normally at a single dose of about 0.01 to about 30 mg/kg body weight, more preferably about 0.1 to about 20 mg/kg body weight, or about 0.1 to about 15 mg/kg body weight, or about 0.02 to about 7 mg/kg body weight, about 0.03 to about 5 mg/kg body weight, or about 0.05 to about 3 mg/kg body weight, or about 1 mg/kg body weight, or about 3.0 mg/kg body weight, or about 10 mg/kg body weight, or about 20 mg/kg body weight. Multiple doses may be administered as necessary. Depending on the severity of the condition, the frequency and the duration of the treatment can be adjusted. In certain embodiments, the antibodies or antigen-binding fragments thereof of the invention can be administered as an initial dose of at least about 0.1 mg to about 800 mg, about 1 to about 600 mg, about 5 to about 300 mg, or about 10 to about 150 mg, to about 100 mg, or to about 50 mg. In certain embodiments, the initial dose may be followed by administration of a second or a plurality of subsequent doses of the antibodies or antigen-binding fragments thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432).

Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, nasal mucosa, rectal and intestinal mucosa, etc.) and may be administered together with other biologically active agents. Administration can be systemic or local. It may be delivered as an aerosolized formulation (See US2011/0311515 and US2012/0128669). The delivery of agents useful for treating respiratory diseases by inhalation is becoming more widely accepted (See A. J. Bitonti and J. A. Dumont, (2006), Adv. Drug Deliv. Rev, 58:1106-1118). In addition to being effective at treating local pulmonary disease, such a delivery mechanism may also be useful for systemic delivery of antibodies (See Maillet et al. (2008), Pharmaceutical Research, Vol. 25, No. 6, 2008).

The pharmaceutical composition can be also delivered in a vesicle, in particular a liposome (see, for example, Langer (1990) Science 249:1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousands Oaks, CA), the PENLET™ (Haselmeier, Stuttgart, Germany), the EPIPEN (Dey, L. P.) and the HUMIRA™ Pen (Abbott Labs, Abbott Park, IL), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Administration Regimens

According to certain embodiments of the present invention, multiple doses of an antibody to RET may be administered to a subject over a defined time course. The methods according to this aspect of the invention comprise sequentially administering to a subject multiple doses of an antibody to RET. As used herein, "sequentially administering" means that each dose of antibody to RET is administered to the subject at a different point in time, e.g., on different days separated by a predetermined interval (e.g., hours, days, weeks or months). The present invention includes methods which comprise sequentially administering to the patient a single initial dose of an antibody to RET, followed by one or more secondary doses of the antibody to RET and optionally followed by one or more tertiary doses of the antibody to RET.

The terms "initial dose," "secondary doses," and "tertiary doses," refer to the temporal sequence of administration of the antibody to RET. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of antibody to RET, but generally may differ from one another in terms of frequency of administration. In certain embodiments, however, the amount of antibody to RET contained in the initial, secondary and/or tertiary doses vary from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antibody to RET which is administered to a patient prior to the administration of the very next dose in the sequence with no intervening doses.

The methods according to this aspect of the invention may comprise administering to a patient any number of secondary and/or tertiary doses of an antibody to RET. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Therapeutic Uses of the Antibodies

Due to their binding to/interaction with the RET protein expressed on certain cells and tissues, the present antibodies are useful for preventing the interaction of the RET protein with one or more ligand/co-receptor complexes e.g. GDNF/GFRα1, artemin/GFRα3, neurturin/GFRα2, or persephin/GFRα4. Given the ability of the anti-RET antibodies of the invention to prevent or inhibit this interaction, the antagonistic antibodies of the present invention may prove useful for inhibition of tumor cell growth when the tumor cell depends on RET signaling for growth, or they may prove useful for inhibiting pain associated with the cancerous condition, as well as pain associated with other diseases or disorders in which RET activation or signaling plays a role. The antibodies of the present invention may be used to slow the growth, and/or metastasis of tumors in a subject with a RET expressing tumor, or to treat the pain associated with the cancerous condition, when administered alone or in conjunction with another anti-tumor agent or therapeutic regimen, or with one or more agents used to further ameliorate the pain associated with the condition. Alternatively, the antibodies of the present invention may be useful for ameliorating at least one symptom associated with the cancerous condition.

It is contemplated that the antibodies of the invention may be used alone, or in conjunction with a second agent, or third agent for treating a RET associated disease or condition, or for alleviating at least one symptom or complication associated with the RET associated disease or condition. A “RET associated disease or condition” is any disease or condition whereby RET is known to be expressed in cells or tissues affected by the disease or condition, and which responds favorably to treatment with either a small molecule therapeutic known to inhibit activation and/or signaling of RET, or which responds favorably to treatment with an anti-RET antibody of the present invention. The second or third agents may be delivered concurrently with the antibodies of the invention, or they may be administered separately, either before or after the antibodies of the invention. The second or third agent may be a small organic molecule, or a biological agent, such as a protein or polypeptide. The second or third agent may be synthetic, or naturally derived. The second or third agent may be an anti-tumor agent, such as a chemotherapeutic drug, or radiation therapy, or a bone-marrow restorative agent, or other agents to reduce fever or pain, another second but different antibody that specifically binds RET, an agent (e.g. an antibody) that binds to a RET ligand, e.g. GDNF, neurturin, artemin, or persephin, or that binds to the co-receptor for RET, such as GFRα1, GFRα2, GFRα3, or GFRα4, or an siRNA specific for the RET molecule.

In yet a further embodiment of the invention the present antibodies are used for the preparation of a pharmaceutical composition for treating patients suffering from a RET associated disease or condition. In yet another embodiment of the invention the present antibodies are used for the preparation of a pharmaceutical composition for reducing the proliferation of tumor cells, or reducing the tumor burden in a patient that has a tumor that depends for growth on RET signaling. In a further embodiment of the invention the present antibodies are used as adjunct therapy with any other agent useful for treating a RET associated disease or condition, including a chemotherapeutic agent, radiation therapy, a bone marrow restorative agent, a second RET antibody, or any other antibody specific for a RET antigen, or an antibody specific for GDNF or GFRα1, or any other palliative therapy known to those skilled in the art.

The antibodies of the invention are useful for the treatment, prevention and/or amelioration of any disease, disorder, or condition associated with RET activity, or for ameliorating at least one symptom associated with the disease, disorder, or condition, or for alleviating the pain associated with such disease, disorder, or condition. Exemplary conditions, diseases and/or disorders, and/or the pain associated with such conditions, diseases, or disorders, that can be treated with the anti-RET antibodies of the present invention include acute or chronic pain, including, but not limited to, neuropathic pain, inflammatory pain, arthritis, migraine, cluster headaches, trigeminal neuralgia, herpetic neuralgia, general neuralgias, irritable bowel syndrome, inflammatory bowel syndrome, visceral pain including abdominal pain, osteoarthritis pain, gout, post-herpetic neuralgia, diabetic neuropathy, radicular pain, sciatica, back pain, head or neck pain, breakthrough pain, post-surgical pain, bone pain, cancer pain. Other conditions treatable by the antibodies and therapeutic methods of the invention included thyroid cancers, familial medullary thyroid carcinoma (FMTC) syndrome, sporadic medullary carcinoma (MTC), multiple endocrine neoplasia syndromes MEN2A and MEN2B, prostate cancer, breast cancer, cervical cancer, colon cancer, or bladder cancer and the pain associated with these conditions. The cancers treatable by the antibodies of the invention may be solid tumors or they may be blood-borne tumors, such as a leukemia. The antibodies of the invention or antigen-binding fragments thereof may also be used to treat the following conditions: non-malignant acute, chronic, or fracture bone pain; rheumatoid arthritis, spinal stenosis; neuropathic low back pain; myofascial pain syndrome; fibromyalgia; temporomandibular joint pain; pancreatic pain; chronic headache pain; tension headache; HIV-associated neuropathy; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; musculoskeletal pain; joint pain; acute gout pain; mechanical low back pain; neck pain; tendonitis; injury/exercise pain; pyelonephritis; appendicitis; cholecystitis; intestinal obstruction; hernias; chest pain, including, cardiac pain; pelvic pain, renal colic pain, acute obstetric pain, including, labor pain; cesarean section pain; burn and trauma pain; endometriosis; herpes zoster pain; sickle cell anemia; acute pancreatitis; orofacial pain including sinusitis pain, dental pain; multiple sclerosis pain; leprosy pain; Behcet's disease pain; adiposis dolorosa; phlebitic pain; Guillain-Barre pain; painful legs and moving toes; Haglund syndrome; Fabry's disease pain; bladder and urogenital disease; hyperactivity bladder; painful bladder syndrome; interstitial cystitis; or prostatitis.

Combination Therapies

As noted above, the methods of the present invention, according to certain embodiments, comprise administering to the subject one or more additional therapeutic agents in combination with an antibody to RET. As used herein, the expression "in combination with" means that the additional therapeutic agents are administered before, after, or concurrent with the pharmaceutical composition comprising the anti-RET antibody. The term "in combination with" also includes sequential or concomitant administration of the anti-RET antibody and a second therapeutic agent.

For example, when administered "before" the pharmaceutical composition comprising the anti-RET antibody, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-RET antibody. When administered "after" the pharmaceutical composition comprising the anti-RET antibody, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the anti-RET antibodies. Administration "concurrent" or with the pharmaceutical composition comprising the anti-RET antibody means that the additional therapeutic agent is administered to the subject in a separate dosage form within less than 5 minutes (before, after, or at the same time) of administration of the pharmaceutical composition comprising the anti-RET antibody, or administered to the subject as a single combined dosage formulation comprising both the additional therapeutic agent and the anti-RET antibody.

Combination therapies may include an anti-RET antibody of the invention and any additional therapeutic agent that may be advantageously combined with an antibody of the invention, or with a biologically active fragment of an antibody of the invention. For example, a second or third therapeutic agent may be employed to aid in reducing the tumor burden in the patient, such as a chemotherapeutic agent, or radiation therapy useful in inhibiting the proliferation of tumor cells in a subject. Alternatively, the antibodies may be used as adjunct therapy after surgical removal of the tumor and may be used alone, or in conjunction with a chemotherapeutic agent, with radiation therapy or with a bone marrow restorative agent. The antibodies may also be used in conjunction with other therapies, as noted above, including a second antibody specific for RET, or an antibody specific for a RET ligand, or with an antibody, or fusion molecule that binds GFRα1 (See SEQ ID NO: 308).

Diagnostic Uses of the Antibodies

The anti-RET antibodies of the present invention may also be used to detect and/or measure RET in a sample, e.g., for diagnostic purposes. It is envisioned that confirmation of a disease or condition thought to be associated with RET may be made by measuring the presence of RET in, for example, a biopsy sample from a tumor (i.e. tumor cells) that depends on growth through RET signaling. Exemplary diagnostic assays for RET may comprise, e.g., contacting a sample, obtained from a patient, with an anti-RET antibody of the invention, wherein the anti-RET antibody is labeled with a detectable label or reporter molecule or used as a capture ligand to selectively isolate a cell expressing the RET protein from patient samples. Alternatively, an unlabeled anti-RET antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure RET containing the F protein in a sample include enzyme-linked immunosorbent assay (ELISA), radioimmunoassay (RIA), and fluorescence-activated cell sorting (FACS).

Samples that can be used in RET diagnostic assays according to the present invention include any tissue or fluid sample obtainable from a patient, which contains detectable quantities of RET protein, or fragments thereof, under normal or pathological conditions. Generally, levels of RET in a particular sample obtained from a healthy patient (e.g., a patient not afflicted with a disease or condition associated with the presence of RET) will be measured to initially establish a baseline, or standard, level of the RET protein. This baseline level of RET can then be compared against the levels of RET measured in samples obtained from individuals suspected of having a disease or condition associated with RET, or symptoms associated with such conditions.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to RET Protein

An immunogen comprising any one of the following can be used to generate antibodies to RET. In certain embodiments, the antibodies of the invention are obtained from mice immunized with a primary immunogen, such as a full length RET protein (See for example, SEQ ID NO: 310 for the human RET51 isoform, also found in ATCC accession number NP_066124.1; and SEQ ID NO: 312 for the human RET9 isoform, also found in ATCC accession number NP_065681.1, both having signal sequences from residue numbers 1-28). The mice may be given one or more booster shots containing either the same molecule, or they may be boosted with immunogenic fragments thereof, such as with the human RET extracellular domain, which ranges from amino acids 1-635 of SEQ ID NO: 313, also found in ATCC accession number NP_066124.1 with signal sequence ranging from amino acid residues 1-28). In certain embodiments, the mice are injected with the full length RET protein, followed by boosting with any of the constructs shown as SEQ ID NOs: 305, 306, 307 and 313 or with a recombinantly prepared molecule.

In certain embodiments, the antibodies of the invention are obtained from mice immunized with a primary immunogen, such as a biologically active RET molecule, or an immunogenic fragment of the RET protein, or DNA encoding the full length protein or the active fragment thereof. The immunogen may be delivered to the animal via any route including but not limited to intramuscularly, subcutaneously, intravenously or intranasally.

In certain embodiments, the full length RET protein or fragments thereof may be used for preparing monospecific, bispecific, or multispecific antibodies.

The full length protein, or a fragment thereof, that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a RET immunoassay. When a desired immune response was achieved, splenocytes were harvested and fused with mouse myeloma cells to preserve their viability and form hybridoma cell lines. The hybridoma cell lines were screened and selected to identify cell lines that produce RET-specific antibodies. Using this technique, and the various immunogens described above, several chimeric antibodies (i.e., antibodies possessing human variable domains and mouse constant domains) were obtained; certain exemplary antibodies generated in this manner were designated as, for example, H2M7086N.

Anti-RET antibodies were also isolated directly from antigen-positive B cells without fusion to myeloma cells, as described in U.S. 2007/0280945A1, herein specifically incorporated by reference in its entirety. Using this method, several fully human anti-RET antibodies (i.e., antibodies possessing human variable domains and human constant domains) were obtained; exemplary antibodies generated in this manner were designated as follows: H4H8044P, H4H8045P, H4H8046P, H4H8048P, H4H8056P, H4H8058P, H4H8060P, H4H8062P, H4H8066P, H4H8067P, H4H8071P, H4H8076P, H4H8079P, H4H8080P, H4H8083P, H4H8084P, H4H8085P and H4H8087P.

The biological properties of the exemplary antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs of selected antibodies specific for RET protein and their corresponding antibody identifiers. Antibodies are typically referred to herein according to the following nomenclature: Fc prefix (e.g. "H4H", "H1M, "H2M"), followed by a numerical identifier (e.g. "7086" as shown in Table 1), followed by a "P" or "N" suffix. Thus, according to this nomenclature, an antibody may be referred to as, e.g. "H2M7086N". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

TABLE 1

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H2M7086N | 2 | 4 | 6 | 8 | 10 | 12 | 14 | 16 |
| H4H8044P | 18 | 20 | 22 | 24 | 26 | 28 | 30 | 32 |
| H4H8045P | 34 | 36 | 38 | 40 | 42 | 44 | 46 | 48 |
| H4H8046P | 50 | 52 | 54 | 56 | 58 | 60 | 62 | 64 |
| H4H8048P | 66 | 68 | 70 | 72 | 74 | 76 | 78 | 80 |
| H4H8056P | 82 | 84 | 86 | 88 | 90 | 92 | 94 | 96 |
| H4H8058P | 98 | 100 | 102 | 104 | 106 | 108 | 110 | 112 |
| H4H8060P | 114 | 116 | 118 | 120 | 122 | 124 | 126 | 128 |
| H4H8062P | 130 | 132 | 134 | 136 | 138 | 140 | 142 | 144 |
| H4H8066P | 146 | 148 | 150 | 152 | 154 | 156 | 158 | 160 |
| H4H8067P | 162 | 164 | 166 | 168 | 170 | 172 | 174 | 176 |
| H4H8071P | 178 | 180 | 182 | 184 | 186 | 188 | 190 | 192 |
| H4H8076P | 194 | 196 | 198 | 200 | 202 | 204 | 206 | 208 |
| H4H8079P | 210 | 212 | 214 | 216 | 218 | 220 | 222 | 224 |
| H4H8080P | 226 | 228 | 230 | 232 | 234 | 236 | 238 | 240 |
| H4H8083P | 242 | 244 | 246 | 248 | 250 | 252 | 254 | 256 |
| H4H8084P | 258 | 260 | 262 | 264 | 266 | 268 | 270 | 272 |
| H4H8085P | 274 | 276 | 278 | 280 | 282 | 284 | 286 | 288 |
| H4H8087P | 290 | 292 | 294 | 296 | 298 | 300 | 302 | 304 |

Example 3. Surface Plasmon Resonance Derived Binding Affinities & Kinetic Constants of Human Monoclonal Anti-RET Antibodies Binding affinities and kinetic constants of human anti-RET antibodies were determined by surface plasmon resonance (Biacore T200) at 25° C. & 37° C. (Tables 2-3). Antibodies, expressed as human IgG4 Fc (i.e., "H4H" designations), were captured onto an anti-human Fc sensor surface (mAb-capture format), and soluble monomeric (hRET.mmh; SEQ ID NO: 305, *Macaca fascicularis* (mf) RET.mmh; SEQ ID NO: 306) or dimeric (hRET.mFc SEQ ID NO: 307) RET protein was injected over the sensor surface. Binding equilibrium dissociation constants ($K_D$) and dissociative half-lives ($t_{1/2}$) were calculated from the kinetic rate constants as: $K_D$ [M]=$k_d/k_a$; and $t_{1/2}$ (min)=(ln2/(60*$k_d$). Calculations were performed using BiacoreT200 evaluation software v1.0.

Several antibodies of the invention displayed sub-nanomolar affinities to human and monkey RET protein (Tables 2-3).

TABLE 2

Biacore binding affinities of human Fc mAbs at 25° C.

| | Binding at 25° C./ Mab Capture Format | | | | |
|---|---|---|---|---|---|
| AbPID | Analyte | ka ($Ms^{-1}$) | Kd ($s^{-1}$) | $K_D$ (Molar) | t½ (min) |
| H4H7086N | hRET.mmh | TBD | TBD | TBD | TBD |
| | hRET.mFc | TBD | TBD | TBD | TBD |
| | mfRET.mmh | TBD | TBD | TBD | TBD |
| H4H8066P | hRET.mmh | 1.27E+05 | 2.57E−04 | 2.02E−09 | 45 |
| | hRET.mFc | 2.07E+05 | 1.20E−04 | 5.80E−10 | 96 |
| | mfRET.mmh | 6.43E+04 | 8.82E−04 | 1.37E−08 | 13 |
| H4H8067P | hRET.mmh | 1.11E+05 | 2.35E−04 | 2.12E−09 | 49 |
| | hRET.mFc | 1.68E+05 | 1.58E−04 | 9.40E−10 | 73 |
| | mfRET.mmh | 1.08E+05 | 4.15E−02 | 3.85E−07 | 0.3 |
| H4H8071P | hRET.mmh | 1.56E+05 | 2.19E−04 | 1.41E−09 | 53 |
| | hRET.mFc | 2.00E+05 | 1.79E−04 | 8.90E−10 | 65 |
| | mfRET.mmh | 1.17E+05 | 2.72E−04 | 2.32E−09 | 43 |
| H4H8076P | hRET.mmh | 2.24E+05 | 3.38E−04 | 1.51E−09 | 34 |
| | hRET.mFc | 2.50E+05 | 1.71E−04 | 6.86E−10 | 68 |
| | mfRET.mmh | 2.12E+05 | 3.27E−04 | 1.54E−09 | 35 |
| H4H8079P | hRET.mmh | 1.43E+05 | 3.84E−04 | 2.68E−09 | 30 |
| | hRET.mFc | 2.09E+05 | 1.51E−04 | 7.20E−10 | 77 |
| | mfRET.mmh | 1.17E+05 | 4.35E−04 | 3.73E−09 | 27 |
| H4H8044P | hRET.mmh | 8.88E+04 | 4.88E−04 | 5.49E−09 | 24 |
| | hRET.mFc | 1.07E+05 | 2.11E−04 | 1.97E−09 | 55 |
| | mfRET.mmh | 9.20E+04 | 1.35E−03 | 1.47E−08 | 9 |
| H4H8045P | hRET.mmh | 2.79E+05 | 2.46E−04 | 8.83E−10 | 47 |
| | hRET.mFc | 3.81E+05 | 8.71E−05 | 2.29E−10 | 133 |
| | mfRET.mmh | 1.92E+05 | 2.80E−03 | 1.46E−08 | 4 |
| H4H8046P | hRET.mmh | 3.06E+05 | 3.01E−04 | 9.84E−10 | 38 |
| | hRET.mFc | 2.80E+05 | 1.81E−04 | 6.45E−10 | 64 |
| | mfRET.mmh | 2.78E+05 | 3.15E−04 | 1.13E−09 | 37 |
| H4H8048P | hRET.mmh | 2.54E+05 | 4.93E−04 | 1.94E−09 | 23 |
| | hRET.mFc | 2.31E+05 | 2.67E−04 | 1.16E−09 | 43 |
| | mfRET.mmh | 2.30E+05 | 5.35E−04 | 2.33E−09 | 22 |
| H4H8080P | hRET.mmh | 2.11E+05 | 5.02E−04 | 2.38E−09 | 23 |
| | hRET.mFc | 1.83E+05 | 2.42E−04 | 1.32E−09 | 48 |
| | mfRET.mmh | NB | NB | NB | NB |
| H4H8083P | hRET.mmh | 1.92E+05 | 4.84E−04 | 2.52E−09 | 24 |
| | hRET.mFc | 1.97E+05 | 2.24E−04 | 1.14E−09 | 52 |
| | mfRET.mmh | 2.07E+05 | 7.11E−04 | 3.44E−09 | 16 |
| H4H8084P | hRET.mmh | 7.23E+05 | 3.75E−04 | 5.18E−10 | 31 |
| | hRET.mFc | 7.20E+05 | 2.04E−04 | 2.84E−10 | 57 |
| | mfRET.mmh | 6.95E+05 | 3.93E−04 | 5.65E−10 | 29 |
| H4H8085P | hRET.mmh | 8.01E+04 | 1.87E−04 | 2.34E−09 | 62 |
| | hRET.mFc | 9.40E+04 | 1.25E−04 | 1.33E−09 | 92 |
| | mfRET.mmh | 6.60E+04 | 2.25E−04 | 3.40E−09 | 51 |
| H4H8087P | hRET.mmh | 8.96E+05 | 2.42E−04 | 2.70E−10 | 48 |
| | hRET.mFc | 1.22E+06 | 1.07E−04 | 8.70E−11 | 108 |
| | mfRET.mmh | 6.41E+05 | 2.72E−04 | 4.24E−10 | 42 |
| H4H8056P | hRET.mmh | 2.11E+05 | 5.39E−04 | 2.56E−09 | 21 |
| | hRET.mFc | 1.85E+05 | 2.72E−04 | 1.47E−09 | 42 |
| | mfRET.mmh | 2.16E+05 | 5.83E−04 | 2.69E−09 | 20 |
| H4H8058P | hRET.mmh | 2.48E+05 | 5.18E−04 | 2.09E−09 | 22 |
| | hRET.mFc | 2.36E+05 | 2.59E−04 | 1.10E−09 | 45 |
| | mfRET.mmh | 2.30E+05 | 5.40E−04 | 2.35E−09 | 21 |
| H4H8060P | hRET.mmh | 7.61E+05 | 3.11E−04 | 4.09E−10 | 37 |
| | hRET.mFc | 8.27E+05 | 1.49E−04 | 1.79E−10 | 78 |
| | mfRET.mmh | 7.51E+05 | 3.93E−04 | 5.23E−10 | 29 |
| H4H8062P | hRET.mmh | 5.05E+05 | 3.70E−04 | 7.33E−10 | 31 |
| | hRET.mFc | 4.00E+05 | 2.20E−04 | 4.90E−10 | 53 |
| | mfRET.mmh | 5.01E+05 | 7.33E−04 | 1.46E−09 | 16 |

NB: No binding observed under conditions used

TABLE 3

| Biacore binding affinities of human Fc mAbs at 37° C. | | | | | |
|---|---|---|---|---|---|
| | Binding at 37° C./ Mab Capture Format | | | | |
| AbPID | Analyte | ka ($Ms^{-1}$) | Kd ($s^{-1}$) | $K_D$ (Molar) | t½ (min) |
| H4H7086N | hRET.mmh | TBD | TBD | TBD | TBD |
| | hRET.mFc | TBD | TBD | TBD | TBD |
| | mfRET.mmh | TBD | TBD | TBD | TBD |
| H4H8066P | hRET.mmh | 1.95E+05 | 1.06E−03 | 5.43E−09 | 11 |
| | hRET.mFc | 2.62E+05 | 3.35E−04 | 1.28E−09 | 34 |
| | mfRET.mmh | 8.19E+04 | 3.23E−03 | 3.94E−08 | 4 |
| H4H8067P | hRET.mmh | 1.59E+05 | 1.16E−03 | 7.31E−09 | 10 |
| | hRET.mFc | 2.04E+05 | 4.58E−04 | 2.24E−09 | 25 |
| | mfRET.mmh | 3.07E+05 | 6.03E−02 | 1.96E−07 | 0.2 |
| H4H8071P | hRET.mmh | 2.36E+05 | 8.96E−04 | 3.79E−09 | 13 |
| | hRET.mFc | 3.00E+05 | 3.12E−04 | 1.04E−09 | 37 |
| | mfRET.mmh | 1.61E+05 | 1.14E−03 | 7.04E−09 | 10 |
| H4H8076P | hRET.mmh | 3.15E+05 | 1.36E−03 | 4.31E−09 | 9 |
| | hRET.mFc | 3.14E+05 | 6.75E−04 | 2.15E−09 | 17 |
| | mfRET.mmh | 2.89E+05 | 1.40E−03 | 4.84E−09 | 8 |
| H4H8079P | hRET.mmh | 2.07E+05 | 1.89E−03 | 9.10E−09 | 6 |
| | hRET.mFc | 2.61E+05 | 5.23E−04 | 2.00E−09 | 22 |
| | mfRET.mmh | 1.54E+05 | 2.05E−03 | 1.33E−08 | 6 |
| H4H8044P | hRET.mmh | 1.51E+05 | 2.81E−03 | 1.86E−08 | 4 |
| | hRET.mFc | 1.37E+05 | 8.50E−04 | 6.21E−09 | 14 |
| | mfRET.mmh | 1.08E+05 | 5.21E−03 | 4.85E−08 | 2 |
| H4H8045P | hRET.mmh | 3.95E+05 | 1.27E−03 | 3.22E−09 | 9 |
| | hRET.mFc | 4.59E+05 | 3.82E−04 | 8.34E−10 | 30 |
| | mfRET.mmh | 2.61E+05 | 1.31E−02 | 5.03E−08 | 1 |
| H4H8046P | hRET.mmh | 7.18E+05 | 1.30E−03 | 1.81E−09 | 9 |
| | hRET.mFc | 3.38E+05 | 6.94E−04 | 2.05E−09 | 17 |
| | mfRET.mmh | 7.04E+05 | 1.35E−03 | 1.92E−09 | 9 |
| H4H8048P | hRET.mmh | 3.39E+05 | 2.42E−03 | 7.14E−09 | 5 |
| | hRET.mFc | 2.80E+05 | 1.09E−03 | 3.89E−09 | 11 |
| | mfRET.mmh | 2.95E+05 | 2.54E−03 | 8.60E−09 | 5 |
| H4H8080P | hRET.mmh | 2.85E+05 | 2.67E−03 | 9.35E−09 | 4 |
| | hRET.mFc | 2.69E+05 | 1.07E−03 | 3.98E−09 | 11 |
| | mfRET.mmh | NB | NB | NB | NB |
| H4H8083P | hRET.mmh | 2.82E+05 | 2.55E−03 | 9.04E−09 | 5 |
| | hRET.mFc | 2.64E+05 | 8.00E−04 | 3.02E−09 | 14 |
| | mfRET.mmh | 2.83E+05 | 4.00E−03 | 1.42E−08 | 3 |
| H4H8084P | hRET.mmh | 1.06E+06 | 1.65E−03 | 1.56E−09 | 7 |
| | hRET.mFc | 1.05E+06 | 8.50E−04 | 8.09E−10 | 14 |
| | mfRET.mmh | 1.01E+06 | 1.78E−03 | 1.76E−09 | 6 |
| H4H8085P | hRET.mmh | 1.44E+05 | 8.97E−04 | 6.23E−09 | 13 |
| | hRET.mFc | 9.90E+04 | 5.50E−04 | 5.50E−09 | 21 |
| | mfRET.mmh | 1.52E+05 | 1.26E−03 | 8.30E−09 | 9 |
| H4H8087P | hRET.mmh | 1.27E+06 | 1.23E−03 | 9.68E−10 | 9 |
| | hRET.mFc | 1.26E+06 | 4.41E−04 | 3.49E−10 | 26 |
| | mfRET.mmh | 8.36E+05 | 1.31E−03 | 1.57E−09 | 9 |
| H4H8056P | hRET.mmh | 3.26E+05 | 2.89E−03 | 8.88E−09 | 4 |
| | hRET.mFc | 2.27E+05 | 1.28E−03 | 5.62E−09 | 9 |
| | mfRET.mmh | 3.03E+05 | 3.13E−03 | 1.03E−08 | 4 |
| H4H8058P | hRET.mmh | 5.28E+05 | 2.21E−03 | 4.18E−09 | 5 |
| | hRET.mFc | 5.52E+05 | 1.21E−03 | 2.18E−09 | 10 |
| | mfRET.mmh | 5.43E+05 | 2.26E−03 | 4.16E−09 | 5 |
| H4H8060P | hRET.mmh | 1.11E+06 | 1.57E−03 | 1.41E−09 | 7 |
| | hRET.mFc | 1.06E+06 | 5.92E−04 | 5.58E−10 | 19 |
| | mfRET.mmh | 1.12E+06 | 2.09E−03 | 1.88E−09 | 6 |
| H4H8062P | hRET.mmh | 6.82E+05 | 1.81E−03 | 2.65E−09 | 6 |
| | hRET.mFc | 3.66E+05 | 8.80E−04 | 2.40E−09 | 13 |
| | mfRET.mmh | 6.78E+05 | 4.28E−03 | 6.31E−09 | 3 |

NB: No binding observed under conditions used

Example 4. Anti-RET Antibodies Potently Block the Binding of Human RET to the GFRα1/GDNF Co-Complex The ability of anti-RET antibodies to block the binding of human RET to pre-complexed plate bound GDNF:GFRα1 was assessed using a competition sandwich ELISA. The majority of RET antibodies potently blocked the binding of RET to plate bound GDNF/GFRα1 co-complex (Table 4). $IC_{50}$ values ranged from 5.2 nM to below the theoretical bottom of the assay (250 pM), with maximum blocking ranging from 72-96%.

Detailed Methods

Recombinant human dimeric GDNF (R&D systems) and human GFRα1.mFc (SEQ ID: 308) were mixed at a 1:1 molar ratio in PBS to obtain a final co-complex concentration of ~2.0 ug/ml. The GDNF-GFRα1 co-complex was incubated for 1 hr at room temp (RT) before coating 96-well microtiter plates overnight at 4° C. Nonspecific binding sites were blocked with BSA.

Separately, 1 nM of biotinylated monomeric RET protein (biot-hRET.mmh; SEQ ID: 305) was titrated with varying amounts of serially diluted antibodies ranging between 0-120 nM. Antibody-RET mixtures were incubated for 1 hour at RT and then transferred to microtiter plates previously coated with the hGDNF/hGFRα1 co-complex. Binding was allowed to proceed for 1 hr at RT followed by extensive washing. Plate-bound biot-hRET.mmh was detected with HRP-conjugated streptavidin and developed with TMB. Plates were read at 450 nm and data analysis used a sigmoidal dose-response model within Prism™ software.

$IC_{50}$ values, calculated as the concentration of antibody required to block 50% of hRET binding to hGDNF/hGFRα1, was used as an indicator of blocking potency. Maximum blocking values represent the ability of anti-RET antibodies to block hRET binding relative to baseline. Baseline values were calculated as the absorbance measured at the constant amount of hRET on the dose curve (0% blocking) and the absorbance measured with no added hRET (100% blocking). The absorbance values of the wells containing the highest concentration for each antibody were used to determine the blocking percent at maximum concentration antibody tested. A summary of $IC_{50}$'s and percent maximum blocking are shown in Table 4.

TABLE 4

$IC_{50}$ values for anti-RET antibodies blocking plate coated pre-complexed GDNF/GFRα1

| AbPID | Blocking 1 nM Biot-hRET.mmh against plate coated Pre-complexed GDNF/GFRα1 IC50, [M] | % Max Blocking |
|---|---|---|
| H2M7086N | 3.3E−10 | 96 |
| H4H7086N | 3.9E−10 | 97 |
| H4H8044P | 5.2E−09 | 91 |
| H4H8045P | 3.4E−10 | 75 |
| H4H8046P | <2.5E−10 # | 95 |
| H4H8048P | <2.5E−10 # | 96 |
| H4H8056P | IC | 73 |
| H4H8058P | 2.5E−10 | 93 |
| H4H8060P | <2.5E−10 # | 95 |
| H4H8062P | <2.5E−10 # | 97 |
| H4H8066P | 4.1E−10 | 57 |
| H4H8067P | <2.5E−10 # | 95 |
| H4H8071P | 3.6E−10 | 72 |
| H4H8076P | <2.5E−10 # | 95 |
| H4H8079P | <2.5E−10 # | 93 |
| H4H8080P | <2.5E−10 # | 82 |
| H4H8083P | <2.5E−10 # | 95 |
| H4H8084P | <2.5E−10 # | 96 |
| H4H8085P | <2.5E−10 # | 96 |
| H4H8087P | <2.5E−10 # | 92 |

Below assay theoretical bottom of < 2.5E−10M; IC—inconclusive

Example 5. Anti-RET Antibodies Inhibit Ligand Dependent RET Signaling in an SRE-Luciferase Reporter Assay & Display Strong Internalization In this example, the effect of anti-RET antibodies on RET signaling and internalization was examined using MCF7 and hRET engineered reporter cell lines.

The glial family ligands GDNF and Artemin trigger the activation of RET through the formation of a high affinity co-complex with GFRα1 or 3, respectively, bringing together two RET molecules and initiating the phosphorylation of specific tyrosine residues. Trans-phosphorylation of RET activates several downstream intracellular cascades, and the upregulation of RET signaling has been implicated in several disease pathologies, including cancer (Borrello, M G, et al., (2013), Expert. Opin. Ther. Targets 17(4): 403-419).

To test the ability of RET antibodies to block GDNF mediated signaling, the human breast adenocarcinoma cell line MCF7, which expresses RET and GFRα1, was transduced with a serum response factor (SRE)-regulated luciferase reporter gene to create a MCF7/SRE-Luc line. Antibodies of this invention displayed potent inhibition of GDNF stimulated RET signaling, with $IC_{50}$ values ranging from 143 pM to >100 nM (Table 5). The percent of inhibition ranged from 60-100%. Several non-blocking antibodies were also identified; H4H8085P stimulated luciferase activity to 50% of the levels observed with GDNF, while H4H8044P, H4H8076P and H4H8046P were weaker activators of luciferase response (2-5% activation).

To determine if the antibodies that blocked GDNF mediated RET signaling would also be efficacious against artemin triggered activity engineered HEK293/hGFRα3/hRET SRE-Luc cell lines were constructed. Most GDNF-dependent blockers of RET-signaling were also blockers of artemin dependent signaling activity in this cell line (Table 5; column 5-6). Interestingly H4H8048P was identified to be a more potent blocker against artemin-dependent signaling compared to GDNF-dependent signaling, perhaps reflecting different epitopes bound by the GDNF-GFRα1 and artemin-GFRα3 co-complexes on the RET receptor.

Lastly, to understand if the blocking activity observed might also be due to degradation of the RET receptor upon antibody binding, several antibodies were tested in an internalization assay (Table 6). Among the seven antibodies tested, H4H8087P was identified as the strongest internalizer, with H4H8079P and H4H7086P also demonstrating potent internalization.

In conclusion, this example illustrates that the anti-RET antibodies of this invention display a range of activating and inhibitory activity on RET signaling in the presence of the glial family ligands, GDNF and artemin.

TABLE 5

$IC_{50}$ and $EC_{50}$ values of anti-RET antibodies in SRE-Luciferase ligand-dependent RET signaling assay

| mAb | MCF7/SRE-luc Avg. $IC_{50}$ (nM) | MCF7/SRE-Luc Avg % Blocking | MCF7/SRE-Luc % Activation | 293/hGFRα3/hRET/SRE-Luc $IC_{50}$ (nM) | 293/hGFRα3/hRET SRE-luc % Blocking |
|---|---|---|---|---|---|
| H2M7086N | 2.6 | 100 | 0 | 4 | 98 |
| H4H8044P | 2.1 | 85 | 2 | 1.6 | 77 |
| H4H8045P | 0.14 | 69 | 0 | 0.42 | 96 |
| H4H8046P | 44 | 78 | 5 | 11.8 | 91 |
| H4H8048P | >100 | 82 | 0 | 8.3 | 99 |
| H4H8056P | 2 | 73 | 0 | ND | ND |
| H4H8058P | 5.4 | 85 | 0 | ND | ND |

TABLE 5-continued

IC50 and EC50 values of anti-RET antibodies in SRE-Luciferase ligand-dependent RET signaling assay

| mAb | MCF7/SRE-luc Avg. $IC_{50}$ (nM) | MCF7/SRE-Luc Avg % Blocking | MCF7/SRE-Luc % Activation | 293/hGFRα3/hRET/SRE-Luc $IC_{50}$ (nM) | 293/hGFRα3/hRET SRE-luc % Blocking |
|---|---|---|---|---|---|
| H4H8060P | >100 | 87 | 0 | ND | ND |
| H4H8062P | 5.2 | 100 | 0 | ND | ND |
| H4H8066P | 0.39 | 60 | 0 | 1.5 | 93 |
| H4H8067P | 3.8 | 91 | 0 | 4.8 | 99 |
| H4H8071P | 0.45 | 84 | 0 | ND | ND |
| H4H8076P | 55.7 | 74 | 3 | ND | ND |
| H4H8079P | 0.15 | 90 | 0 | 0.8 | 96 |
| H4H8080P | >100 | 41 | 0 | 341 | 57 |
| H4H8083P | >100 | 68 | 0 | 57 | 81 |
| H4H8084P | 10.4 | 100 | 0 | 2.1 | 94 |
| H4H8085P | NB | 0 | 47 | 127 | 72 |
| H4H8087P | 0.25 | 100 | 0 | 0.25 | 100 |

TABLE 6

Percent internalization of anti-RET antibodies at 37° C. relative to H4H8087P

| PID | Internalization (% H4H8087P) |
|---|---|
| H4H7086N | 59.03 |
| H4H8058P | 42.02 |
| H4H8062P | 44.94 |
| H4H8067P | 58.20 |
| H4H8079P | 62.78 |
| H4H8048P | 35.37 |
| H4H8087P | 100.00 |

Detailed Methods

Generation of the MCF7/SRE-Luciferase Stable Cell Lines

MCF7 cells naturally express RET and GFRα1. Production of MCF7/SRELuc cells utilized a stably incorporated SRE-Luciferase generated via transduction of MCF7 with the Cignal Lenti SRE Reporter kit (SABiosciences) and a two-week selection in puromycin. The lentivirus expresses the firefly luciferase gene under the control of a minimal CMV promoter and tandem repeats of the serum response element (SRE).

Generation of HEk293/hGFRa1 (or 3)/hRET/SRE-Luciferase Stable Cell Lines

Human GFRα (1 or 3) and hRET were stably introduced into HEK293 cells via sequential rounds of Lipofectamine2000-mediated transfection, and selected for at least two weeks in 500 ug/ml G418 (hGFRa1 or 3) and 100 ug/ml hygromycin B (hRET). The HEK293 double stable lines expressing hGFRa1/hRET or hGFRa3/hRET were then transduced with the Cignal Lenti SRE Reporter kit, as described above, to generate the HEK293/hGFRa1/hRET/SRE-Luc cell line and the artemin-responsive HEK293/GFRa3/hRET/SRE-Luc cell line.

Inhibition of GDNF-Stimulated Luciferase Activity in MCF7/SRE-Luciferase Engineered Cell Lines Twenty thousand MCF7-SRE-luc cells were seeded in PDL coated 96 well plates in Optimem+0.5% FBS and grown overnight at 37° C., 5% $CO_2$. For inhibition curves, cells were incubated for 1 hr with serially diluted anti hRET mAbs ranging from 1.6 pM to 1 uM. A constant dose of human GDNF (4-10 pM) was then added and cells were incubated for an additional 6 hr.

To assess activating properties of anti-RET mAbs, MCF7-SRE-Luc cells were incubated for 6 hr with serially diluted anti hRET mAbs ranging from 1.6 pM to 1 uM in the absence of ligand.

GDNF dose response curves were measured using serially diluted GDNF, ranging from 0.05 pM to 10 nM, added to wells without antibodies and incubated for 6 hr at 37° C. Luciferase activity was measured with ONE GLO™ reagent (Promega) and relative light units (RLUs) were measured on a Victor luminometer (Perkin Elmer).

Inhibition of Artemin-Stimulated Luciferase Activity in HEK293/hGFRa3/hRET Engineered Cell Lines Inhibition of Artemin-stimulated luciferase activity in HEK293/hGFRa3/hRET/SRE-Luc cell lines was assessed using anti-RET antibodies via the method described for MCF7/SRE-Luc cells. To generate inhibition curves, cells were incubated for 1 hr with serially diluted anti hRET antibodies ranging from 1.6 pM to 1 uM. Cells were then stimulated with a constant dose of hArtemin (100 pM) for 6 hr. Artemin dose response curves were generated by adding serially diluted hArtemin (0.17 pM-10 nM) to cells for 6 hr at 37° C. without the addition of antibody. Luciferase activity measurements and curve fitting was performed as described for GDNF stimulated luciferase activity.

Calculation of $EC_{50}/IC_{50}$ Values $EC_{50}/IC_{50}$ values were determined from a four-parameter logistic equation over a 12-point response curve using GraphPad Prism. Percent blocking is reported for the highest antibody dose and data is reported as average±standard deviation (SD).

Quantitative Analysis of Internalization Properties of Anti-RET Antibodies

To test anti hRET mAbs for internalization, HEK293/hGFRa1/hRET/SRE-Luc cells were incubated with antibodies (10 ug/ml) for 30 minutes on ice, followed by one wash. Cells were then incubated with alexa488 conjugated anti-hFc Fab secondary antibodies for 30 minutes followed by a second wash. Antibodies were allowed to internalize for 4 hr at 37° C. or remain at 4° C. to prevent internalization. Cells were fixed in 4% formaldehyde and cell surface alexa488 was quenched by incubation with an anti alexa488-quenching antibody for 1 hr at 4° C. Nuclei were stained with Hoechst stain and images were acquired on the ImageXpress micro XL (Molecular Devices).

Total alexa488 intensity in the intracellular vesicles at 37° C. in the quenched samples was quantitated via Columbus image analysis software (Perkin Elmer). The total internalized mAb intensity is expressed as a percentage of the strongest internalizing mAb.

Example 6. Generation of a Bi-Specific Antibody

Various bi-specific antibodies are generated for use in practicing the methods of the invention. For example, RET specific antibodies are generated in a bi-specific format (a "bi-specific") in which variable regions binding to distinct domains of the RET protein are linked together to confer dual-domain specificity within a single binding molecule. Appropriately designed bi-specifics may enhance overall RET neutralization efficacy through increasing both specificity and binding avidity. Variable regions with specificity for individual domains are paired on a structural scaffold that allows each region to bind simultaneously to separate epitopes, or to different regions within one domain. In one example for a bi-specific, heavy chain variable regions ($V_H$) from a binder with specificity for one domain are recombined with light chain variable regions ($V_L$) from a series of binders with specificity for a second domain to identify non-cognate $V_L$ partners that can be paired with an original $V_H$ without disrupting the original specificity for that $V_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind RET and a second target, such as, but not limited to, for example, a a tumor antigen, may be prepared in a bi-specific format using techniques described herein, or other techniques known to those skilled in the art. Antibody variable regions binding to distinct regions may be linked together with variable regions that bind to relevant sites on, for example, a different antigen to confer dual-antigen specificity within a single binding molecule. Appropriately designed bi-specifics of this nature serve a dual function. For example, in the case of a bi-specific antibody that binds ie. RET and one of its ligands, one may be able to better inhibitor tumor cell growth, without the need for administration of a composition containing two separate antibodies. Variable regions with specificity for RET, are combined with a variable region with specificity for one of its ligands and are paired on a structural scaffold that allows each variable region to bind to the separate antigens.

The bi-specific binders are tested for binding and functional blocking of the target antigen, for example, RET, in any of the assays described above for antibodies. For example, standard methods to measure soluble protein binding are used to assess the bispecific interaction, such as Biacore, ELISA, size exclusion chromatography, multi-angle laser light scattering, direct scanning calorimetry, and other methods. Binding of bi-specific antibodies to both RET and one of its ligands is determined through use of an ELISA binding assay in which synthetic peptides representing the different antigens are coated onto the wells of microtiter plates, and binding of a bi-specific is determined through use of a secondary detection antibody. Binding experiments can also be conducted using surface plasmon resonance experiments, in which real-time binding interaction of peptide to antibody is measured by flowing a peptide or bi-specific across a sensor surface on which bi-specific or peptide, respectively, is captured. Functional in vitro blocking of both RET and one of its ligands by a bi-specific is determined using any bioassay such as the assays described herein, or by in vivo protection studies in appropriate animal models, such as tumor bearing animal models.

What is claimed is:

1. An isolated human monoclonal antibody or antigen-binding fragment thereof that specifically binds to REarranged During Transfection (RET), wherein the antibody comprises three heavy chain CDRs (HCDR1, HCDR2 and HCDR3) and three light chain CDRs (LCDR1, LCDR2 and LCDR3) contained within a heavy chain variable region/light chain variable region (HCVR/LCVR) amino acid sequence pair of SEQ ID NOS: 210/218.

2. The isolated human monoclonal antibody or antigen-binding fragment thereof of claim 1, comprising a HCDR1 having the amino acid sequence of SEQ ID NO:212, a HCDR2 having the amino acid sequence of SEQ ID NO:214, a HCDR3 having the amino acid sequence of SEQ ID NO:216, a LCDR1 having the amino acid sequence of SEQ ID NO:220, a LCDR2 having the amino acid sequence of SEQ ID NO:222, and a LCDR3 having the amino acid sequence of SEQ ID NO:224.

3. The isolated antibody or antigen-binding fragment thereof of claim 1, wherein the antibody or antigen binding fragment thereof comprises an HCVR having the amino acid sequence of SEQ ID NO:210 and an LCVR having the amino acid sequence of SEQ ID NO:218.

4. An isolated nucleic acid molecule encoding the antibody or antigen-binding fragment thereof of claim 1.

5. An expression vector comprising the nucleic acid molecule of claim 4.

6. A pharmaceutical composition comprising the human monoclonal antibody or antigen-binding fragment thereof of claim 1 and a pharmaceutically acceptable carrier or diluent.

7. A method of treating a disorder or condition associated with expression, activation, or signaling of the RET receptor tyrosine kinase gene, or the pain associated with the disorder or condition, the method comprising administering the human monoclonal antibody or antigen-binding fragment thereof of claim 1 to a patient in need thereof.

8. The method of claim 7, wherein the disorder or condition associated with expression, activation, or signaling of the RET receptor tyrosine kinase gene is a cancer and wherein the cancer is selected form the group consisting of thyroid cancer, lung cancer, pancreatic cancer, skin cancer, breast cancer, and a blood-borne cancer.

9. The method of claim 7, wherein the disorder or condition associated with expression, activation, or signaling of the RET receptor tyrosine kinase gene is selected from the group consisting of acute pain, chronic pain, neuropathic pain, inflammatory pain, arthritis, osteoarthritis, migraine, cluster headaches, trigeminal neuralgia, herpetic neuralgia, general neuralgias, neurodegenerative disorders, neuroendocrine disorders, visceral pain, acute gout, post-herpetic neuralgia, diabetic neuropathy, sciatica, back pain, head or neck pain, severe or intractable pain, breakthrough pain, post-surgical pain, dental pain, rhinitis, cancer pain, and bladder disorders.

10. A method for inhibiting tumor growth or tumor cell proliferation, wherein the tumor or tumor cell expresses RET, the method comprising administering the human monoclonal antibody or antigen-binding fragment thereof of claim 1 to a patient in need thereof.

11. The method of claim 10, wherein the tumor is a solid tumor or a blood-borne tumor.

12. The method of claim 11, wherein the solid tumor is selected from the group consisting of a thyroid tumor, a lung tumor, a pancreatic tumor, a skin tumor, and a breast tumor.

13. The method of claim 12, wherein the thyroid tumor is a papillary thyroid carcinoma (PTC) or a medullary thyroid carcinoma (MTC).

14. The method of claim 13, wherein the medullary thyroid carcinoma is a hereditary MTC selected from the group consisting of multiple endocrine neoplasia type 2 or 3 (MEN2A, MEN2B) and familial medullary thyroid carcinoma (FMTC) syndrome, or wherein the medullary thyroid carcinoma is a sporadic MTC.

15. The method of claim 12, wherein the lung tumor is a lung adenocarcinoma.

16. The method of claim 12, wherein the lung tumor is a non-small cell lung cancer (NSCLC).

17. The method of claim 12, wherein the skin tumor is a melanoma.

18. The method of claim 11, wherein the blood-borne tumor is a leukemia.

19. The method of claim 18, wherein the leukemia is chronic myelomonocytic leukemia.

20. A method of down-modulating RET expression and/or function, the method comprising administering the human monoclonal antibody or antigen-binding fragment thereof of claim 1 to a patient in need thereof.

21. The method of claim 20, wherein the down-modulating of RET expression and/or function results in down-regulation of a downstream signaling pathway selected from the group consisting of the RAS/RAF pathway and the PI3K pathway.

22. The method of claim 10, wherein the antibody or antigen-binding fragment is administered to the patient in combination with a second therapeutic agent.

23. The method of claim 22, wherein the second therapeutic agent is selected from the group consisting of a small molecule tyrosine kinase inhibitor, an anti-tumor agent, an siRNA specific for RET, a second antibody specific for RET, and a pain-reducing agent.

24. The method of claim 23, wherein the small molecule tyrosine kinase inhibitor is selected from the group consisting of vandetanib, cediranib, (AZD2171), gefitinib, erlotinib, SU14813, vatalanib, sorafenib, sorafenib (BAY43-9006), sunitinib, cabozantinib, motesanib, XL-647, XL-999, AG-013736, BIBF1120, TSU68, GW786034, AEE788, CP-547632, KRN951, CHIR258, CEP-7055, OSI-930, ABT-869, E7080, ZK-304709, BAY57-9352, L-21649, BMS582664, XL-880, XL-184, XL-820, RPI-1, PP-1, and NVP-AST478.

25. The method of claim 23, wherein the anti-tumor agent is selected from the group consisting of a chemotherapeutic agent, a radionuclide, and an antibody-drug conjugate.

26. The method of claim 23, wherein the pain-reducing agent is selected from the group consisting of a nerve growth factor (NGF) inhibitor, aspirin or another NSAID, morphine, steroids, an anti-$Na_v1.7$ antibody, a small molecule inhibitor of $Na_v1.7$, a $Na_v1.8$ antagonist, a $Na_v1.9$ antagonist, a cytokine inhibitor, inhibitors of caspase-1, p38, inhibitors of IKK1/2, inhibitors of CTLA-4Ig, and an opioid.

27. The method of claim 26, wherein the nerve growth factor (NGF) inhibitor is a small molecule NGF antagonist or an anti-NGF antibody, the steroids is prednisone, the $Na_v1.8$ antagonist is an anti-$Na_v1.8$ antibody or a small molecule inhibitor of $Na_v1.8$, the $Na_v1.9$ antagonist is an anti-$Na_v1.9$ antibody or a small molecule inhibitor of $Na_v1.9$, and/or the cytokine inhibitor is an interleukin-1 (IL-1) inhibitor, an IL-18 inhibitor, or an IL-6 or IL-6R inhibitor.

28. The method of claim 27, wherein the IL-1 inhibitor is rilonacept or IL-1 trap, anakinra, a small molecule IL-1 antagonist, or an anti-IL-1 antibody;

the IL-18 inhibitor is a small molecule IL-18 antagonist or an anti-IL-18 antibody; and/or the IL-6 or IL-6R inhibitor is a small molecule IL-6 antagonist, an anti-IL-6 antibody or an anti-IL-6 receptor antibody.

* * * * *